US012723249B2

(12) United States Patent
Gao et al.

(10) Patent No.: US 12,723,249 B2
(45) Date of Patent: Sep. 1, 2026

(54) AAV PRODUCTION STRATEGY USING A CELL LINE EXPRESSING AN INDUCIBLE REP GENE

(71) Applicant: University of Massachusetts, Westborough, MA (US)

(72) Inventors: Guangping Gao, Worcester, MA (US); Dan Wang, Worcester, MA (US); Jote Bulcha, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 1053 days.

(21) Appl. No.: 17/767,962

(22) PCT Filed: Oct. 14, 2020

(86) PCT No.: PCT/US2020/055593

§ 371 (c)(1),
(2) Date: Apr. 11, 2022

(87) PCT Pub. No.: WO2021/076634

PCT Pub. Date: Apr. 22, 2021

(65) Prior Publication Data

US 2023/0183711 A1 Jun. 15, 2023

Related U.S. Application Data

(60) Provisional application No. 62/915,560, filed on Oct. 15, 2019, provisional application No. 63/010,719, filed on Apr. 16, 2020.

(51) Int. Cl.
*C12N 15/52* (2006.01)
*C07K 14/005* (2006.01)

(52) U.S. Cl.
CPC ............ *C12N 15/52* (2013.01); *C07K 14/005* (2013.01); *C12N 2750/14122* (2013.01); *C12N 2750/14143* (2013.01); *C12N 2750/14152* (2013.01)

(58) Field of Classification Search
CPC .......... C12N 15/52; C12N 2750/14122; C12N 2750/14143; C12N 2750/14152; C12N 15/86; C07K 14/005
See application file for complete search history.

(56) References Cited

U.S. PATENT DOCUMENTS

2005/0148076 A1 7/2005 Allen
2013/0023034 A1 1/2013 Noordman et al.

FOREIGN PATENT DOCUMENTS

WO WO 92/01070 A1 1/1992
WO WO 2009/061369 A2 5/2009
WO WO 2011/112089 A2 9/2011

OTHER PUBLICATIONS

Swart et al. Genetic codes with no dedicated stop codon: context-dependent translation termination. Cell (2016), 166, 691-702. (Year: 2016).*
Invitation to Pay Additional Fees for Application No. PCT/US2020/055593, mailed Jan. 11, 2021.
International Search Report and Written Opinion for Application No. PCT/US2020/055593, mailed Mar. 11, 2021.
International Preliminary Report on Patentability for Application No. PCT/US2020/055593, mailed Apr. 28, 2022.
PCT/US2020/055593, Jan. 11, 2021, Invitation to Pay Additional Fees.
PCT/US2020/055593, Mar. 11, 2021, International Search Report and Written Opinion.
PCT/US2020/055593, Apr. 28, 2022, International Preliminary Report on Patentability.
Extended European Search Report for Application No. 20875985.2, mailed Oct. 26, 2023.
Kelemen, New tools at the intersection of genetic code expansion, virus engineering, and directed evolution. Doctoral thesis, Boston College. Apr. 2019. 345 pages.

* cited by examiner

*Primary Examiner* — Iqbal H Chowdhury
(74) *Attorney, Agent, or Firm* — Wolf, Greenfield & Sacks, P.C.

(57) ABSTRACT

Aspects of the disclosure relate to manufacturing AAV using a stable cell line that expresses the rep gene by engineering tRNA to suppress a mutation introduced to a rep integrated into the genome of the cell line.

3 Claims, 20 Drawing Sheets

Specification includes a Sequence Listing.

Infection (fluorescence imaging)

HEK293 cells

Infection (fluorescence imaging)

AAV PRODUCTION STRATEGY USING A CELL LINE EXPRESSING AN INDUCIBLE REP GENE

RELATED APPLICATIONS

This application is a national stage filing under 35 U.S.C. § 371 of international PCT application PCT/US2020/055593, filed Oct. 14, 2020, which claims priority under 35 U.S.C. § 119(e) to U.S. provisional patent application Ser. No. 63/010,719, filed Apr. 16, 2020, and U.S. provisional patent application Ser. No. 62/915,560, filed Oct. 15, 2019, the entire contents of each of which are incorporated herein by reference.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Apr. 8, 2022, is named U012070132US02-SEQ-KZM and is 98,413 bytes in size.

BACKGROUND OF INVENTION

Adeno-associated virus (AAV) technology has been widely used for gene therapy because of its ability to deliver a genetic payload to a target tissue. For example, there have been a significant number of clinical trials involving AAV vectors, as well as commercialized gene therapy products. However, the adenoviral early gene (E1) mediated activation of AAV rep gene is cytotoxic and genotoxic.

SUMMARY OF INVENTION

Aspects of the disclosure relate to manufacturing AAV using a cell line (e.g., a stable cell line) that expresses the AAV rep gene by engineering tRNA to suppress a mutation introduced to a rep gene integrated into the genome of the cell line.

Accordingly, in some aspects, the disclosure relates to a nucleic acid encoding an adeno-associated virus (AAV) rep gene that comprises one or more mutations that prematurely stops the translation of at least one of the AAV rep proteins.

In some embodiments, the mutation is a nonsense mutation, for example, a nonsense mutation encoding a UAG, UAA, or UGA codon. In other embodiments, the nonsense mutation encodes a UAG codon replacing a codon for serine downstream of the p19 promotor of the AAV rep gene. In some embodiments, the mutation is a frameshift mutation. In some embodiments, the nucleic acid further comprises a promoter operably linked to the AAV rep gene. In some embodiments, the promoter is a P5 promoter or a P19 promoter. In some embodiments, the nuclei acid further comprises a stuffer sequence. In some embodiments, the stuffer sequence is placed between the promoter and the AAV rep gene. In some embodiments, the nucleic acid further comprises one or more insulator sequence. In some embodiments, the AAV rep gene is flanked by a pair of insulator sequences.

In some aspects, the disclosure relates to cells with a nucleic acids encoding an adeno-associated virus (AAV) rep gene integrated in its genome, wherein the nucleic acid comprises a mutation that prematurely stops the translation of at least one of the AAV rep proteins. In some embodiments, the mutation is a nonsense mutation, for example, a nonsense mutation encoding a UAG, UAA, or UGA codon. In other embodiments, the nonsense mutation encodes a UAG codon replacing a codon for serine downstream of the p19 promotor of the AAV rep gene. In some embodiments, the mutation is a frameshift mutation.

In some embodiments, the cell is a mammalian cell, for example, a HEK293, HEK293T, HeLa, A549, or Chinese hamster ovary (CHO) cell. In some embodiments, the cell is a HEK293 cell.

In some embodiments, the nucleic acid further comprises a promoter operably linked to the AAV rep gene. In some embodiments, the promoter is a P5 promoter or a P19 promoter. In some embodiments, the nuclei acid further comprises a stuffer sequence. In some embodiments, the stuffer sequence is placed between the promoter and the AAV rep gene. In some embodiments, the nucleic acid further comprises one or more insulator sequence. In some embodiments, the AAV rep gene is flanked by a pair of insulator sequences.

In other embodiments, the cell further comprises one or more orthogonal aminoacyl-tRNA synthetases (aaRS). In yet other embodiments, the cell further comprises one or more non-canonical amino acids (ncAAs), wherein the one or more ncAAs bind to the one or more orthogonal aaRSs.

In some embodiments, the cell comprises one or more rAAV vectors. In other embodiments, the cell further comprises one or more AAV helper genes.

In some aspects, the disclosure relates to methods of expressing an adeno-associated virus (AAV) rep protein from an AAV rep gene, wherein the rep gene comprises a mutation that prematurely stops the translation of the AAV rep protein, the method comprising the step of delivering a vector to the cell encoding a synthetic suppressor transfer RNA (tRNA), wherein the synthetic suppressor tRNA comprises an anticodon region configured to recognize the mutation that prematurely stops the translation of the AAV rep proteins. In some embodiments, the AAV rep gene is integrated into the genome of a cell. In other embodiments, the anticodon region recognizes a UAG, UAA, or UGA codon. In yet other embodiments, the anticodon region recognizes a UAG codon replacing a codon for serine downstream of the p19 promotor of the AAV rep gene. In some embodiments, the anticodon region recognizes a frameshift mutation. In other embodiments, the synthetic suppressor tRNA comprises a four-base anticodon.

In some embodiments, the synthetic suppressor tRNA is charged with an amino acid selected from the group consisting of Serine, Lysine, Glutamic acid, Glutamine, Tryptophan, Leucine, and Tyrosine. In other embodiments, the synthetic suppressor tRNA is charged with a ncAA.

In some embodiments, the vector is an Ad vector. In some embodiments, the step further comprises delivering to the cell an AAV cap gene. In other embodiments, the AAV cap gene is integrated into the host cell. In yet other embodiments, the AAV cap gene is encoded on vector that is delivered to the cell, which can be the same vector in which the suppressor tRNA are encoded. In some embodiments, the method further comprises adding a rAVV vector. In other embodiments, the method further comprises isolating rAVV particles produced by the cell.

In some aspects, the disclosure relates to methods of expressing an adeno-associated virus (AAV) rep protein from an AAV rep gene, and wherein the cell expresses an orthogonal aminoacyl-tRNA synthetase-tRNA pair, the method comprising the step of delivering to the cell the cognate non canonical amino acid (ncAA). In some embodiments, the AAV rep gene is integrated into the genome of a cell. In some embodiments, the ncAA is Ne-2-azidoethyl-oxycarbonyl-L-lysine (NAEK). In other embodiments, the orthogonal tRNA recognizes a UAG, UAA, or UGA codon. In yet other embodiments, the orthogonal tRNA recognizes a UAG codon replacing a codon for serine downstream of the p19 promotor of the AAV rep gene. In some embodiments, the orthogonal tRNA recognizes a frameshift mutation. In other embodiments, the orthogonal tRNA comprises a four-base anticodon.

In some embodiments, the method further comprises the step of delivering an AAV cap gene to the cell. In some embodiments, the AAV cap gene is integrated into the host cell. In other embodiments, the AAV cap gene is encoded on a vector that is delivered to the cell. In some embodiments, the vector is an Ad vector. In some embodiments, the method further comprises adding a rAVV vector. In other embodiments, the method further comprises isolating rAVV particles produced by the cell.

In some aspects, the present disclosure provides a method of producing recombinant adeno-associated virus (rAAV), the method comprising delivering to a cell of a synthetic suppressor transfer RNA (tRNA) or a cognate non canonical amino acid (ncAA). In some embodiments, the method further comprises delivering to the cell one or more AAV helper genes. In some embodiments, the method further comprises delivering to the cell an AAV vector encoding a transgene.

BRIEF DESCRIPTION OF DRAWINGS

FIG. 2A shows one embodiment of a rep gene structure. FIG. 2B shows an experimental flowchart for HEK293 cells.

FIG. 3A is a graph of the AAV titer in crude lysate (ddPCR) showing the average GC/mL for HEK293 cells. FIG. 3B shows the fluorescence imaging of the infection.

FIG. 3C is a graph of the flow cytometry of the infection showing the percent of cells (EGFP) for Cis plas. (EGFP), Adv helper gene, AAV2 rep/cap, AAV2 rep*(mut)/cap, $tRNA^{tyr}$ (UAG), $tRNA^{ser}$ (UAG), $tRNA^{gln}$ (UAG), and $tRNA^{lys}$ (UAG).

FIG. 4A shows the fluorescence imaging of the infection. FIG. 4B is a graph of the flow cytometry of the infection showing the percent of cells (EGFP) for pEGFP (cis), pHelper, pAAV2-rep/cap, pAAV2-rep*(mut)/cap, pPylRS/$tRNA^{Pyl}$(UAG), NAEK, $ptRNA^{ser}$ (UAG).

FIG. 5A shows a schematic depicting a piggybac transposon construct used to create a rep*/cap cell line. The two primer pairs used for genotyping PCR are shown by the arrows. FIG. 5B shows an image of genotyping PCR of agarose gel electrophoresis. Six putative cell lines were genotyped. Cell line #2 marked by dotted rectangle is used in the next experiments. FIG. 5C shows a flowchart showing the experimental layout. FIG. 5D shows representative GFP and bright-field images of cells two days after co-infection with crude lysate and adenovirus.

FIG. 6A shows a flowchart depicting the experimental layout. FIG. 6B shows representative GFP and bright-field images of cells two days after co-infection with crude lysate and adenovirus.

FIG. 7A shows a schematic depicting rep gene structure with amber mutations at different locations. The mutation position on the left and right side of the rep gene structure corresponds to the Met starting position for the large (REP78 and REP68) and small (REP52 and REP40) protein driven by p5 and p19, respectively. FIG. 7B shows representative GFP images of cells two days after co-infection of HRK293 cells with crude lysate and adenovirus. NAEK is added to a final concentration of 1 mM.

FIG. 8A shows a cartoon of a cell line containing Rep*(C714A)/Cap and orthogonal Pyrrolysyl-tRNA synthetase/pyltRNA pair, which is developed by using a piggybac transposon system. FIG. 8B shows a schematics illustration of the experimental procedure using the cell line in FIG. 8A. The HEK293 cell harboring orthogonal pyrrolysyl-tRNA system was transfected by a plasmid expressing either wild type or mutant EGFP (Y39X) as a read through reporter. NAEK was supplemented to the media to a final concentration of 1 mM, 2 mM and 4 mM, 24 hours post-transfection. GFP expression was evaluated 72 hours post-transfection. FIG. 8C shows the representative GFP images of transfected cells two days post NAEK supplementation. FIG. 8D shows a schematic illustration of experimental procedure of rAAV production using the HEK293 cells harboring the orthogonal pyrrolysyl-tRNA system. The HEK cells were sequentially infected with Adv5 and hybrid AdV-AAV-EGFP 24 hours apart, after treating cells with NAEK to a final concentration of 1 mM. Crude lysate was harvested 72 hours post initial infection and heat treated at 56° C. for 30 min. 1/10th of the crude lysate was used to infect new HEK293 cells. FIG. 8E shows representative GFP images of HEK293 cells infected with heat treated crude lysate, 48 hours post infection.

FIG. 9A shows a schematic illustration of the experimental procedure. HEK293 cells were transfected by a plasmid expressing either wild type or mutant EGFP (Y39X) and a plasmid containing orthogonal Pyrrolysyl-tRNA synthetase/pyltRNA pair. Either NAEK, or CpK was supplemented to the media to a final concentration of 1 mM, 0.2 mM and 0.5 mM, respectively, 24 hours post transfection. FIG. 9B shows representative GFP images of transfected HEK293 cells 24-hours post non-canonical amino acid (ncAA) supplementation. FIG. 9C shows schematic representation of experimental procedures in ncAA as an inducer for AAV production. HEK cells shown in FIG. 8A were sequentially infected with Adv5 and hybrid AdV-AAV-EGFP 24 hours apart, after treating cells with ncAA at the indicated final concentrations. Crude lysate was harvested 72 hours post initial infection and heat treated at 56° C. for 30 min. 1/10th of the crude lysate was used to infect new HEK293 cells. FIG. 9D shows representative GFP images of HEK293 cells infected with heat treated crude lysate, 48-hours post-infection.

FIG. 10A shows a cartoon of the modified Rep*/Cap constructs used to make cell lines. construct (a) and (b) contain 600 bp stuffer sequence at the p5 promoter but not construct (c) and (d). Construct (a) and (c) have the core insulator sequence flanking the expression cassette but not construct (b) and (d). FIG. 10B shows a schematic illustration of experimental procedure. Cell line that carries construct (c) was sequentially infected with Adv5 and hybrid AdV-AAV-EGFP, after transfecting the cells with suppressor tRNA (tRNAser(UAG)). Crude lysate was harvested 72 hours post-transfection and heat treated at 56° C. for 30 min. 1/10th of the crude lysate was used to infect new HEK293 cells. FIG. 10C shows representative GFP images of HEK293 cells infected with heat treated crude lysate, 48-hours post-infection.

DETAILED DESCRIPTION OF INVENTION

Figure 1:
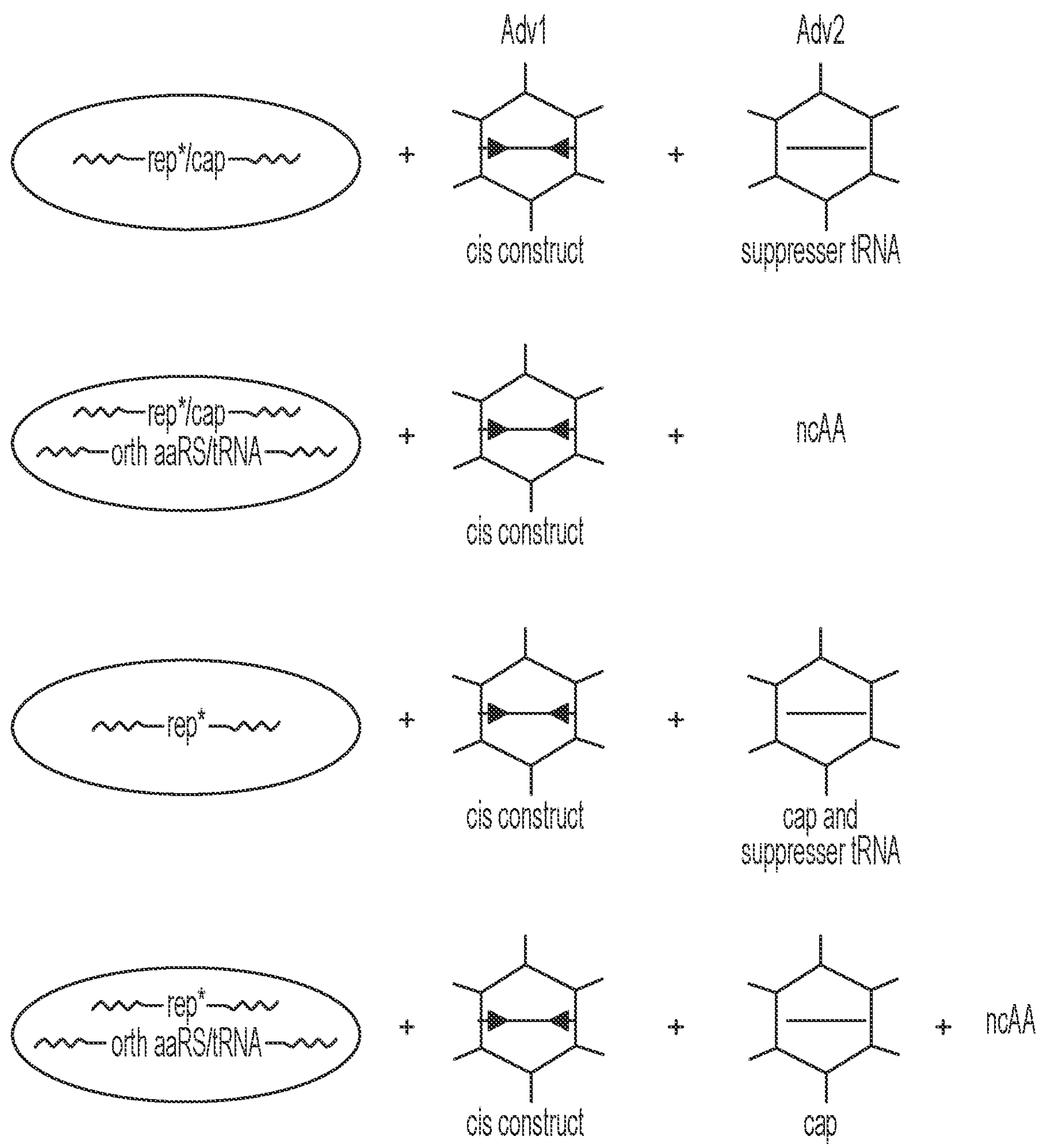
FIG. 1 is a schematic showing AAV production schemes.

In some aspects, the disclosure relates to methods and systems for production of recombinant adeno-associated virus (rAAV) particles. The disclosure is based, in part, on compositions comprising the adeno-associated virus (AAV) rep gene containing one or more mutations that prematurely stop the translation of at least one of the AAV rep proteins encoded therein. In some embodiments, single or multiple amber mutations are coupled with or without frameshift mutations to completely knock out the rep gene. In some embodiments, the rep gene is stably integrated into the genome of a cell line.

The disclosure is also based, in part, on inducing the AAV production cell line platform in different ways. For example, in some embodiments, one or more synthetic suppressor transfer RNAs (tRNAs) are configured to read-through certain stop codons (e.g., premature termination codons, "PTC"). In some embodiments, the one or more synthetic suppressor tRNAs are encoded by a vector, for example a viral vector (e.g., rAAV vector, lentiviral vector, etc.). The disclosure is also based, in part, on the use of one or more orthogonal aminoacyl-tRNA synthetase-tRNA pairs that are capable of inducing AAV production when non-canonical amino acids (ncAAs), such as but not limited to Ne-2-azidoethyloxycarbonyl-L-lysine (NAEK), are provided to the cells. In some embodiments, the orthogonal aminoacyl-tRNA synthetase-tRNA pair is stably integrated in the cell, for example the same cell containing the mutated rep gene. In some embodiments, a four-base codon/anticodon strategy is used to rescue a strong stop and frame shift mutation introduced to a rep gene.

As described further in the Examples section, the use of anticodon engineered synthetic suppressor tRNAs or orthogonal aminoacyl-tRNA synthetase-tRNA pairs with supplied ncAAs resulted in the suppression of the mutation in the AAV rep gene, thereby allowing the rep gene to be functionally expressed.

Mutant Rep Gene

Aspects of the disclosure relate to transgenes encoding an adeno-associated virus (AAV) rep gene containing one or more mutations that prematurely stop the translation of at least one of the AAV rep proteins encoded therein. In some embodiments, single or multiple mutations (e.g., amber mutations) are coupled with or without frameshift mutations to reduce activity or function of the rep gene. In some embodiments, the rep gene is stably integrated into the genome of a cell line.

The genome of AAV comprises Inverted Terminal Repeats (ITRs) flank the unique coding nucleotide sequences for the non-structural replication (Rep) proteins and the structural (VP) proteins. Following wild type AAV infection in mammalian cells, the Rep genes (e.g., Rep78, Rep52, etc.) are expressed from the P5 promoter and the P19 promotor, respectively and both Rep proteins have a function in the replication of the viral genome. A splicing event in the Rep open reading frame (ORF) results in the expression of four Rep proteins (e.g., Rep78, Rep68, Rep52 and Rep40). However, it has been observed that the un-spliced mRNA, encoding Rep78 and Rep52 proteins, in some embodiments, is sufficient for AAV vector packaging in mammalian cells. In some embodiments, expression of Rep78 and Rep52 proteins is sufficient for production of rAAVs in insect cells.

An exemplary nucleotide sequence encoding wild type Rep protein is set forth in SEQ ID NO: 1:

(SEQ ID NO: 1)

ATGCCGGGGTTTTACGAGATTGTGATTAAGGTCCCCAGCGACCTTGACGAGCATCTGCCCGGCA

TTTCTGACAGCTTTGTGAACTGGGTGGCCGAGAAGGAATGGGAGTTGCCGCCAGATTCTGACAT

GGATCTGAATCTGATTGAGCAGGCACCCCTGACCGTGGCCGAGAAGCTGCAGCGCGACTTTCTG

ACGGAATGGCGCCGTGTGAGTAAGGCCCCGGAGGCTCTTTTCTTTGTGCAATTTGAGAAGGGAG

AGAGCTACTTCCACATGCACGTGCTCGTGGAAACCACCGGGGTGAAATCCATGGTTTTGGGACG

TTTCCTGAGTCAGATTCGCGAAAAACTGATTCAGAGAATTTACCAGCGGGATCGAGCCGACTTT

GCCAAACTGGTTCGCGGTCACAAAGACCAGAAATGGCGCCGGAGGCGGGAACAAGGTGGTGGAT

GAGTGCTACATCCCCAATTACTTGCTCCCCAAAACCCAGCCTGAGCTCCAGTGGGCGTGGACTA

ATATGGAACAGTATTTAAGCGCCTGTTTGAATCTCACGGAGCGTAAACGGTTGGTGGCGCAGCA

TCTGACGCACGTGTCGCAGACGCAGGAGCAGAACAAAGAGAATCAGAATCCCAATTCTGATGCG

CCGGTGATCAGATCAAAAACTTCAGCCAGGTACATGGAGCTGGTCGGGTGGCTCGTGGACAAGG

GGATTACCTCGGAGAAGCAGTGGATCCAGGAGGACCAGGCCTCATACATCTCCTTCAATGCGGC

CTCCAACTCGCGGTCCCAAATCAAGGCTGCCTTGGACAATGCGGGAAAGATTATGAGCCTGACT

AAAACCGCCCCCGACTACCTGGTGGGCCAGCAGCCCGTGGAGGACATTTCCAGCAATCGGATTT

ATAAAATTTTGGAACTAAACGGGTACGATCCCCAATATGCGGCTTCCGTCTTTCTGGGATGGGC

CACGAAAAAGTTCGGCAAGAGGAACACCATCTGGCTGTTTGGGCCTGCAACTACCGGGAAGACC

-continued

```
AACATCGCGGAGGCCATAGCCCACACTGTGCCCTTCTACGGGTGCGTAAACTGGACCAATGAGA

ACTTTCCCTTCAACGACTGTGTCGACAAGATGGTGATCTGGTGGGAGGAGGGGAAGATGACCGC

CAAGGTCGTGGAGTCGGCCAAAGCCATTCTCGGAGGAAGCAAGGTGCGCGTGGACCAGAAATGC

AAGTCCTCGGCCCAGATAGACCCGACTCCCGTGATCGTCACCTCCAACACCAACATGTGCGCCG

TGATTGACGGGAACTCAACGACCTTCGAACACCAGCAGCCGTTGCAAGACCGGATGTTCAAATT

TGAACTCACCCGCCGTCTGGATCATGACTTTGGGAAGGTCACCAAGCAGGAAGTCAAAGACTTT

TTCCGGTGGGCAAAGGATCACGTGGTTGAGGTGGAGCATGAATTCTACGTCAAAAAGGGTGGAG

CCAAGAAAAGACCCGCCCCCAGTGACGCAGATATAAGTGAGCCCAAACGGGTGCGCGAGTCAGT

TGCGCAGCCATCGACGTCAGACGCGGAAGCTTCGATCAACTACGCAGACAGGTACCAAAACAAA

TGTTCTCGTCACGTGGGCATGAATCTGATGCTGTTTCCCTGCAGACAATGCGAGAGAATGAATC

AGAATTCAAATATCTGCTTCACTCACGGACAGAAAGACTGTTTAGAGTGCTTTCCCGTGTCAGA

ATCTCAACCCGTTTCTGTCGTCAAAAAGGCGTATCAGAAACTGTGCTACATTCATCATATCATG

GGAAAGGTGCCAGACGCTTGCACTGCCTGCGATCTGGTCAATGTGGATTTGGATGACTGCATCT

TTGAACAATAA
```

An exemplary amino acid sequence for wild type Rep protein is set forth in SEQ ID NO: 2:

```
                                                 (SEQ ID NO: 2)
MPGFYEIVIKVPSDLDEHLPGISDSFVNWVAEKEWELPPDSDMDLNLIEQAPLTVAEKLQRDFL

TEWRRVSKAPEALFFVQFEKGESYFHMHVLVETTGVKSMVLGRFLSQIREKLIQRIYRGIEPTL

PNWFAVTKTRNGAGGGNKVVDECYIPNYLLPKTQPELQWAWTNMEQYLSACLNLTERKRLVAQH

LTHVSQTQEQNKENQNPNSDAPVIRSKTSARYMELVGWLVDKGITSEKQWIQEDQASYISFNAA

SNSRSQIKAALDNAGKIMSLTKTAPDYLVGQQPVEDISSNRIYKILELNGYDPQYAASVFLGWA

TKKFGKRNTIWLFGPATTGKTNIAEAIAHTVPFYGCVNWTNENFPFNDCVDKMVIWWEEGKMTA

KVVESAKAILGGSKVRVDQKCKSSAQIDPTPVIVTSNTNMCAVIDGNSTTFEHQQPLQDRMFKF

ELTRRLDHDFGKVTKQEVKDFFRWAKDHVVEVEHEFYVKKGGAKKRPAPSDADISEPKRVRESV

AQPSTSDAEASINYADRYQNKCSRHVGMNLMLFPCRQCERMNQNSNICFTHGQKDCLECFPVSE

SQPVSVVKKAYQKLCYIHHIMGKVPDACTACDLVNVDLDDCIFEQ*
```

In some embodiments, the disclosure provides a nucleic acid encoding an adeno-associated virus (AAV) rep gene that comprises one or more mutations that prematurely stops the translation of at least one AAV rep protein. In some embodiments, at least one of the mutations is a nonsense mutation. In some embodiments, the mutation is a frameshift mutation. In some embodiments, the nonsense mutation encodes a UAG, UAA, or UGA codon.

In some embodiments, the nonsense mutation encodes a UAG codon replacing a codon for serine downstream of the p19 promotor of the AAV rep gene.

In some embodiments, the nonsense mutation encodes a UAG codon replacing a codon for serine at position 238 (S238X) of SEQ ID NO: 2. In some embodiments, the nucleotide sequence encoding the mutant Rep protein S238X comprises a C714A mutation compared to the wild type Rep gene (SEQ ID NO: 1).

An exemplary nucleotide sequence comprises C714A mutation for encoding a mutant Rep protein is set forth in SEQ ID NO: 3 (mutation site underlined in boldface):

(SEQ ID NO: 3)

ATGCCGGGGTTTTACGAGATTGTGATTAAGGTCCCCAGCGACCTTGACGAGCATCTGCCCGGCA

TTTCTGACAGCTTTGTGAACTGGGTGGCCGAGAAGGAATGGGAGTTGCCGCCAGATTCTGACAT

GGATCTGAATCTGATTGAGCAGGCACCCCTGACCGTGGCCGAGAAGCTGCAGCGCGACTTTCTG

ACGGAATGGCGCCGTGTGAGTAAGGCCCCGGAGGCTCTTTTCTTTGTGCAATTTGAGAAGGGAG

AGAGCTACTTCCACATGCACGTGCTCGTGGAAACCACCGGGGTGAAATCCATGGTTTTGGGACG

TTTCCTGAGTCAGATTCGCGAAAAACTGATTCAGAGAATTTACCAGCGGGATCGAGCCGACTTT

GCCAAACTGGTTCGCGGTCACAAAGACCAGAAATGGCGCCGGAGGCGGGAACAAGGTGGTGGAT

GAGTGCTACATCCCCAATTACTTGCTCCCCAAAACCCAGCCTGAGCTCCAGTGGGCGTGGACTA

ATATGGAACAGTATTTAAGCGCCTGTTTGAATCTCACGGAGCGTAAACGGTTGGTGGCGCAGCA

TCTGACGCACGTGTCGCAGACGCAGGAGCAGAACAAAGAGAATCAGAATCCCAATTCTGATGCG

CCGGTGATCAGATCAAAAACTTCAGCCAGGTACATGGAGCTGGTCGGGTGGCTCGTGGACAAGG

GGATTACCTAGGAGAAGCAGTGGATCCAGGAGGACCAGGCCTCATACATCTCCTTCAATGCGGC

CTCCAACTCGCGGTCCCAAATCAAGGCTGCCTTGGACAATGCGGGAAAGATTATGAGCCTGACT

AAAACCGCCCCCGACTACCTGGTGGGCCAGCAGCCCGTGGAGGACATTTCCAGCAATCGGATTT

ATAAAATTTTGGAACTAAACGGGTACGATCCCCAATATGCGGCTTCCGTCTTTCTGGGATGGGC

CACGAAAAAGTTCGGCAAGAGGAACACCATCTGGCTGTTTGGGCCTGCAACTACCGGGAAGACC

AACATCGCGGAGGCCATAGCCCACACTGTGCCCTTCTACGGGTGCGTAAACTGGACCAATGAGA

ACTTTCCCTTCAACGACTGTGTCGACAAGATGGTGATCTGGTGGGAGGAGGGGAAGATGACCGC

CAAGGTCGTGGAGTCGGCCAAAGCCATTCTCGGAGGAAGCAAGGTGCGCGTGGACCAGAAATGC

AAGTCCTCGGCCCAGATAGACCCGACTCCCGTGATCGTCACCTCCAACACCAACATGTGCGCCG

TGATTGACGGGAACTCAACGACCTTCGAACACCAGCAGCCGTTGCAAGACCGGATGTTCAAATT

TGAACTCACCCGCCGTCTGGATCATGACTTTGGGAAGGTCACCAAGCAGGAAGTCAAAGACTTT

TTCCGGTGGGCAAAGGATCACGTGGTTGAGGTGGAGCATGAATTCTACGTCAAAAAGGGTGGAG

CCAAGAAAAGACCCGCCCCCAGTGACGCAGATATAAGTGAGCCCAAACGGGTGCGCGAGTCAGT

TGCGCAGCCATCGACGTCAGACGCGGAAGCTTCGATCAACTACGCAGACAGGTACCAAAACAAA

TGTTCTCGTCACGTGGGCATGAATCTGATGCTGTTTCCCTGCAGACAATGCGAGAGAATGAATC

AGAATTCAAATATCTGCTTCACTCACGGACAGAAAGACTGTTTAGAGTGCTTTCCCGTGTCAGA

ATCTCAACCCGTTTCTGTCGTCAAAAAGGCGTATCAGAAACTGTGCTACATTCATCATATCATG

GGAAAGGTGCCAGACGCTTGCACTGCCTGCGATCTGGTCAATGTGGATTTGGATGACTGCATCT

TTGAACAATAA

An exemplary amino acid sequence comprises S238X mutation is set forth in SEQ ID NO: 4 (mutation site underlined in boldface):

(SEQ ID NO: 4)

MPGFYEIVIKVPSDLDEHLPGISDSFVNWVAEKEWELPPDSDMDLNLIE

QAPLTVAEKLQRDFLTEWRRVSKAPEALFFVQFEKGESYFHMHVLVETT

GVKSMVLGRFLSQIREKLIQRIYRGIEPTLPNWFAVTKTRNGAGGGNKV

VDECYIPNYLLPKTQPELQWAWTNMEQYLSACLNLTERKRLVAQHLTHV

SQTQEQNKENQNPNSDAPVIRSKTSARYMELVGWLVDKGIT*EKQWIQE

DQASYISFNAASNSRSQIKAALDNAGKIMSLTKTAPDYLVGQQPVEDIS

SNRIYKILELNGYDPQYAASVFLGWATKKFGKRNTIWLFGPATTGKTNI

-continued

AEAIAHTVPFYGCVNWTNENFPFNDCVDKMVIWWEEGKMTAKVVESAKA

ILGGSKVRVDQKCKSSAQIDPTPVIVTSNTNMCAVIDGNSTTFEHQQPL

QDRMFKFELTRRLDHDFGKVTKQEVKDFFRWAKDHVVEVEHEFYVKKGG

AKKRPAPSDADISEPKRVRESVAQPSTSDAEASINYADRYQNKCSRHVG

MNLMLFPCRQCERMNQNSNICFTHGQKDCLECFPVSESQPVSVVKKAYQ

KLCYIHHIMGKVPDACTACDLVNVDLDDCIFEQ*

In some embodiments, the nonsense mutation encodes more than one UAG codon replacing more than one codon for serine residues in a wild type Rep protein. In some embodiments, the mutant Rep protein comprises a stop codon at position 13 (S13X) and position 238 (S238X) of SEQ ID NO: 2. In some embodiments, the nucleotide sequence encoding the mutant Rep protein S13X-S238X comprises a AGC(37,38,39) TAG and a C714A mutation compared to the wild type Rep gene (SEQ ID NO: 1).

An exemplary nucleotide sequence comprises AGC (37, 38,39) TAG and a C714A mutation for encoding a mutant Rep protein is set forth in SEQ ID NO: 5 (mutation site underlined in boldface):

(SEQ ID NO: 5)

ATGCCGGGGTTTTACGAGATTGTGATTAAGGTCCCCTAGGACCTTGACGAGCATCTGCCCGGCA

TTTCTGACAGCTTTGTGAACTGGGTGGCCGAGAAGGAATGGGAGTTGCCGCCAGATTCTGACAT

GGATCTGAATCTGATTGAGCAGGCACCCCTGACCGTGGCCGAGAAGCTGCAGCGCGACTTTCTG

ACGGAATGGCGCCGTGTGAGTAAGGCCCCGGAGGCTCTTTTCTTTGTGCAATTTGAGAAGGGAG

AGAGCTACTTCCACATGCACGTGCTCGTGGAAACCACCGGGGTGAAATCCATGGTTTTGGGACG

TTTCCTGAGTCAGATTCGCGAAAAACTGATTCAGAGAATTTACCAGCGGGATCGAGCCGACTTT

GCCAAACTGGTTCGCGGTCACAAAGACCAGAAATGGCGCCGGAGGCGGGAACAAGGTGGTGGAT

GAGTGCTACATCCCCAATTACTTGCTCCCCAAAACCCAGCCTGAGCTCCAGTGGGCGTGGACTA

ATATGGAACAGTATTTAAGCGCCTGTTTGAATCTCACGGAGCGTAAACGGTTGGTGGCGCAGCA

TCTGACGCACGTGTCGCAGACGCAGGAGCAGAACAAAGAGAATCAGAATCCCAATTCTGATGCG

CCGGTGATCAGATCAAAAACTTCAGCCAGGTACATGGAGCTGGTCGGGTGGCTCGTGGACAAGG

GGATTACCTAGGAGAAGCAGTGGATCCAGGAGGACCAGGCCTCATACATCTCCTTCAATGCGGC

CTCCAACTCGCGGTCCCAAATCAAGGCTGCCTTGGACAATGCGGGAAAGATTATGAGCCTGACT

AAAACCGCCCCCGACTACCTGGTGGGCCAGCAGCCCGTGGAGGACATTTCCAGCAATCGGATTT

ATAAAATTTTGGAACTAAACGGGTACGATCCCCAATATGCGGCTTCCGTCTTTCTGGGATGGGC

CACGAAAAAGTTCGGCAAGAGGAACACCATCTGGCTGTTTGGGCCTGCAACTACCGGGAAGACC

AACATCGCGGAGGCCATAGCCCACACTGTGCCCTTCTACGGGTGCGTAAACTGGACCAATGAGA

ACTTTCCCTTCAACGACTGTGTCGACAAGATGGTGATCTGGTGGGAGGAGGGGAAGATGACCGC

CAAGGTCGTGGAGTCGGCCAAAGCCATTCTCGGAGGAAGCAAGGTGCGCGTGGACCAGAAATGC

AAGTCCTCGGCCCAGATAGACCCGACTCCCGTGATCGTCACCTCCAACACCAACATGTGCGCCG

TGATTGACGGGAACTCAACGACCTTCGAACACCAGCAGCCGTTGCAAGACCGGATGTTCAAATT

TGAACTCACCCGCCGTCTGGATCATGACTTTGGGAAGGTCACCAAGCAGGAAGTCAAAGACTTT

TTCCGGTGGGCAAAGGATCACGTGGTTGAGGTGGAGCATGAATTCTACGTCAAAAAGGGTGGAG

CCAAGAAAAGACCCGCCCCCAGTGACGCAGATATAAGTGAGCCCAAACGGGTGCGCGAGTCAGT

TGCGCAGCCATCGACGTCAGACGCGGAAGCTTCGATCAACTACGCAGACAGGTACCAAAACAAA

TGTTCTCGTCACGTGGGCATGAATCTGATGCTGTTTCCCTGCAGACAATGCGAGAGAATGAATC

AGAATTCAAATATCTGCTTCACTCACGGACAGAAAGACTGTTTAGAGTGCTTTCCCGTGTCAGA

ATCTCAACCCGTTTCTGTCGTCAAAAAGGCGTATCAGAAACTGTGCTACATTCATCATATCATG

GGAAAGGTGCCAGACGCTTGCACTGCCTGCGATCTGGTCAATGTGGATTTGGATGACTGCATCT

TTGAACAATAA

An exemplary amino acid sequence comprises S13X-S238X mutation is set forth in SEQ ID NO: 6 (mutation site underlined in boldface):

```
                                                        (SEQ ID NO: 6)
MPGFYEIVIKVP*DLDEHLPGISDSFVNWVAEKEWELPPDSDMDLNLIEQAPLTVAEKLQRDFL

TEWRRVSKAPEALFFVQFEKGESYFHMHVLVETTGVKSMVLGRFLSQIREKLIQRIYRGIEPTL

PNWFAVTKTRNGAGGGNKVVDECYIPNYLLPKTQPELQWAWTNMEQYLSACLNLTERKRLVAQH

LTHVSQTQEQNKENQNPNSDAPVIRSKTSARYMELVGWLVDKGIT*EKQWIQEDQASYISFNAA

SNSRSQIKAALDNAGKIMSLTKTAPDYLVGQQPVEDISSNRIYKILELNGYDPQYAASVFLGWA

TKKFGKRNTIWLFGPATTGKTNIAEAIAHTVPFYGCVNWTNENFPFNDCVDKMVIWWEEGKMTA

KVVESAKAILGGSKVRVDQKCKSSAQIDPTPVIVTSNTNMCAVIDGNSTTFEHQQPLQDRMFKF

ELTRRLDHDFGKVTKQEVKDFFRWAKDHVVEVEHEFYVKKGGAKKRPAPSDADISEPKRVRESV

AQPSTSDAEASINYADRYQNKCSRHVGMNLMLFPCRQCERMNQNSNICFTHGQKDCLECFPVSE

SQPVSVVKKAYQKLCYIHHIMGKVPDACTACDLVNVDLDDCIFEQ*
```

In some embodiments, the nonsense mutation encodes a UAG codon replacing a codon for lysine downstream of the p19 promotor of the AAV rep gene.

In some embodiments, the nonsense mutation encodes a UAG codon replacing a codon for lysine at position 240 (K240X) of SEQ ID NO: 2. In some embodiments, the nucleotide sequence encoding the mutant Rep protein K240Stop comprises a A719T mutation compared to the wild type Rep gene.

An exemplary nucleotide sequence comprises A719T mutation for encoding a mutant Rep protein is set forth in SEQ ID NO: 7 (mutation site underlined in boldface):

```
                                                        (SEQ ID NO: 7)
ATGCCGGGGTTTTACGAGATTGTGATTAAGGTCCCCAGCGACCTTGACGAGCATCTGCCCGGCA

TTTCTGACAGCTTTGTGAACTGGGTGGCCGAGAAGGAATGGGAGTTGCCGCCAGATTCTGACAT

GGATCTGAATCTGATTGAGCAGGCACCCCTGACCGTGGCCGAGAAGCTGCAGCGCGACTTTCTG

ACGGAATGGCGCCGTGTGAGTAAGGCCCCGGAGGCTCTTTTCTTTGTGCAATTTGAGAAGGGAG

AGAGCTACTTCCACATGCACGTGCTCGTGGAAACCACCGGGGTGAAATCCATGGTTTTGGGACG

TTTCCTGAGTCAGATTCGCGAAAAACTGATTCAGAGAATTTACCAGCGGGATCGAGCCGACTTT

GCCAAACTGGTTCGCGGTCACAAAGACCAGAAATGGCGCCGGAGGCGGGAACAAGGTGGTGGAT

GAGTGCTACATCCCCAATTACTTGCTCCCCAAAACCCAGCCTGAGCTCCAGTGGGCGTGGACTA

ATATGGAACAGTATTTAAGCGCCTGTTTGAATCTCACGGAGCGTAAACGGTTGGTGGCGCAGCA

TCTGACGCACGTGTCGCAGACGCAGGAGCAGAACAAAGAGAATCAGAATCCCAATTCTGATGCG

CCGGTGATCAGATCAAAAACTTCAGCCAGGTACATGGAGCTGGTCGGGTGGCTCGTGGACAAGG

GGATTACCTCGGAGTAGCAGTGGATCCAGGAGGACCAGGCCTCATACATCTCCTTCAATGCGGC

CTCCAACTCGCGGTCCCAAATCAAGGCTGCCTTGGACAATGCGGGAAAGATTATGAGCCTGACT

AAAACCGCCCCCGACTACCTGGTGGGCCAGCAGCCCGTGGAGGACATTTCCAGCAATCGGATTT

ATAAAATTTTGGAACTAAACGGGTACGATCCCCAATATGCGGCTTCCGTCTTTCTGGGATGGGC

CACGAAAAAGTTCGGCAAGAGGAACACCATCTGGCTGTTTGGGCCTGCAACTACCGGGAAGACC

AACATCGCGGAGGCCATAGCCCACACTGTGCCCTTCTACGGGTGCGTAAACTGGACCAATGAGA

ACTTTCCCTTCAACGACTGTGTCGACAAGATGGTGATCTGGTGGGAGGAGGGGAAGATGACCGC

CAAGGTCGTGGAGTCGGCCAAAGCCATTCTCGGAGGAAGCAAGGTGCGCGTGGACCAGAAATGC

AAGTCCTCGGCCCAGATAGACCCGACTCCCGTGATCGTCACCTCCAACACCAACATGTGCGCCG

TGATTGACGGGAACTCAACGACCTTCGAACACCAGCAGCCGTTGCAAGACCGGATGTTCAAATT

TGAACTCACCCGCCGTCTGGATCATGACTTTGGGAAGGTCACCAAGCAGGAAGTCAAAGACTTT
```

-continued

```
TTCCGGTGGGCAAAGGATCACGTGGTTGAGGTGGAGCATGAATTCTACGTCAAAAAGGGTGGAG
CCAAGAAAAGACCCGCCCCCAGTGACGCAGATATAAGTGAGCCCAAACGGGTGCGCGAGTCAGT
TGCGCAGCCATCGACGTCAGACGCGGAAGCTTCGATCAACTACGCAGACAGGTACCAAAACAAA
TGTTCTCGTCACGTGGGCATGAATCTGATGCTGTTTCCCTGCAGACAATGCGAGAGAATGAATC
AGAATTCAAATATCTGCTTCACTCACGGACAGAAAGACTGTTTAGAGTGCTTTCCCGTGTCAGA
ATCTCAACCCGTTTCTGTCGTCAAAAAGGCGTATCAGAAACTGTGCTACATTCATCATATCATG
GGAAAGGTGCCAGACGCTTGCACTGCCTGCGATCTGGTCAATGTGGATTTGGATGACTGCATCT
TTGAACAATAA
```

An exemplary amino acid sequence comprises K240X mutation is set forth in SEQ ID NO: 8 (mutation site underlined in boldface):

```
                                                    (SEQ ID NO: 8)
MPGFYEIVIKVPSDLDEHLPGISDSFVNWVAEKEWELPPDSDMDLNLIEQAPLTVAEKLQRDFL
TEWRRVSKAPEALFFVQFEKGESYFHMHVLVETTGVKSMVLGRFLSQIREKLIQRIYRGIEPTL
PNWFAVTKTRNGAGGGNKVVDECYIPNYLLPKTQPELQWAWTNMEQYLSACLNLTERKRLVAQH
LTHVSQTQEQNKENQNPNSDAPVIRSKTSARYMELVGWLVDKGITSE*QWIQEDQASYISFNAA
SNSRSQIKAALDNAGKIMSLTKTAPDYLVGQQPVEDISSNRIYKILELNGYDPQYAASVFLGWA
TKKFGKRNTIWLFGPATTGKTNIAEAIAHTVPFYGCVNWTNENFPFNDCVDKMVIWWEEGKMTA
KVVESAKAILGGSKVRVDQKCKSSAQIDPTPVIVTSNTNMCAVIDGNSTTFEHQQPLQDRMFKF
ELTRRLDHDFGKVTKQEVKDFFRWAKDHVVEVEHEFYVKKGGAKKRPAPSDADISEPKRVRESV
AQPSTSDAEASINYADRYQNKCSRHVGMNLMLFPCRQCERMNQNSNICFTHGQKDCLECFPVSE
SQPVSVVKKAYQKLCYIHHIMGKVPDACTACDLVNVDLDDCIFEQ*
```

In some embodiments, the nonsense mutation encodes more than one UAG codon replacing more than one codon for lysine residues in a wild type Rep protein. In some embodiments, the mutant Rep protein comprises a stop codon at position 10 (K10X) and position 240 (K240X) of SEQ ID NO: 2. In some embodiments, the nucleotide sequence encoding the mutant Rep protein K10X-K240X comprises a A28T and a A719T mutation compared to the wild type Rep gene (SEQ ID NO: 1).

An exemplary nucleotide sequence comprises A28T and a A719T mutation for encoding a mutant Rep protein is set forth in SEQ ID NO: 9 (mutation site underlined in boldface):

```
                                                    (SEQ ID NO: 9)
ATGCCGGGGTTTTACGAGATTGTGATTTAGGTCCCCAGCGACCTTGACGAGCATCTGCCCGGCA
TTTCTGACAGCTTTGTGAACTGGGTGGCCGAGAAGGAATGGGAGTTGCCGCCAGATTCTGACAT
GGATCTGAATCTGATTGAGCAGGCACCCCTGACCGTGGCCGAGAAGCTGCAGCGCGACTTTCTG
ACGGAATGGCGCCGTGTGAGTAAGGCCCCGGAGGCTCTTTTCTTTGTGCAATTTGAGAAGGGAG
AGAGCTACTTCCACATGCACGTGCTCGTGGAAACCACCGGGGTGAAATCCATGGTTTTGGGACG
TTTCCTGAGTCAGATTCGCGAAAAACTGATTCAGAGAATTTACCAGCGGGATCGAGCCGACTTT
GCCAAACTGGTTCGCGGTCACAAAGACCAGAAATGGCGCCGGAGGCGGGAACAAGGTGGTGGAT
GAGTGCTACATCCCCAATTACTTGCTCCCCAAAACCCAGCCTGAGCTCCAGTGGGCGTGGACTA
ATATGGAACAGTATTTAAGCGCCTGTTTGAATCTCACGGAGCGTAAACGGTTGGTGGCGCAGCA
TCTGACGCACGTGTCGCAGACGCAGGAGCAGAACAAAGAGAATCAGAATCCCAATTCTGATGCG
CCGGTGATCAGATCAAAAACTTCAGCCAGGTACATGGAGCTGGTCGGGTGGCTCGTGGACAAGG
GGATTACCTCGGAGTAGCAGTGGATCCAGGAGGACCAGGCCTCATACATCTCCTTCAATGCGGC
CTCCAACTCGCGGTCCCAAATCAAGGCTGCCTTGGACAATGCGGGAAAGATTATGAGCCTGACT
```

-continued

```
AAAACCGCCCCCGACTACCTGGTGGGCCAGCAGCCCGTGGAGGACATTTCCAGCAATCGGATTT

ATAAAATTTTGGAACTAAACGGGTACGATCCCCAATATGCGGCTTCCGTCTTTCTGGGATGGGC

CACGAAAAAGTTCGGCAAGAGGAACACCATCTGGCTGTTTGGGCCTGCAACTACCGGGAAGACC

AACATCGCGGAGGCCATAGCCCACACTGTGCCCTTCTACGGGTGCGTAAACTGGACCAATGAGA

ACTTTCCCTTCAACGACTGTGTCGACAAGATGGTGATCTGGTGGGAGGAGGGGAAGATGACCGC

CAAGGTCGTGGAGTCGGCCAAAGCCATTCTCGGAGGAAGCAAGGTGCGCGTGGACCAGAAATGC

AAGTCCTCGGCCCAGATAGACCCGACTCCCGTGATCGTCACCTCCAACACCAACATGTGCGCCG

TGATTGACGGGAACTCAACGACCTTCGAACACCAGCAGCCGTTGCAAGACCGGATGTTCAAATT

TGAACTCACCCGCCGTCTGGATCATGACTTTGGGAAGGTCACCAAGCAGGAAGTCAAAGACTTT

TTCCGGTGGGCAAAGGATCACGTGGTTGAGGTGGAGCATGAATTCTACGTCAAAAAGGGTGGAG

CCAAGAAAAGACCCGCCCCCAGTGACGCAGATATAAGTGAGCCCAAACGGGTGCGCGAGTCAGT

TGCGCAGCCATCGACGTCAGACGCGGAAGCTTCGATCAACTACGCAGACAGGTACCAAAACAAA

TGTTCTCGTCACGTGGGCATGAATCTGATGCTGTTTCCCTGCAGACAATGCGAGAGAATGAATC

AGAATTCAAATATCTGCTTCACTCACGGACAGAAAGACTGTTTAGAGTGCTTTCCCGTGTCAGA

ATCTCAACCCGTTTCTGTCGTCAAAAAGGCGTATCAGAAACTGTGCTACATTCATCATATCATG

GGAAAGGTGCCAGACGCTTGCACTGCCTGCGATCTGGTCAATGTGGATTTGGATGACTGCATCT

TTGAACAATAA
```

An exemplary amino acid sequence comprises K10X-K240X mutation is set forth in SEQ ID NO: 10 (mutation site underlined in boldface):

```
                                                       (SEQ ID NO: 10)
MPGFYEIVI*VPSDLDEHLPGISDSFVNWVAEKEWELPPDSDMDLNLIEQAPLTVAEKLQRDFL

TEWRRVSKAPEALFFVQFEKGESYFHMHVLVETTGVKSMVLGRFLSQIREKLIQRIYRGIEPTL

PNWFAVTKTRNGAGGGNKVVDECYIPNYLLPKTQPELQWAWTNMEQYLSACLNLTERKRLVAQH

LTHVSQTQEQNKENQNPNSDAPVIRSKTSARYMELVGWLVDKGITSE*QWIQEDQASYISFNAA

SNSRSQIKAALDNAGKIMSLTKTAPDYLVGQQPVEDISSNRIYKILELNGYDPQYAASVFLGWA

TKKFGKRNTIWLFGPATTGKTNIAEAIAHTVPFYGCVNWTNENFPFNDCVDKMVIWWEEGKMTA

KVVESAKAILGGSKVRVDQKCKSSAQIDPTPVIVTSNTNMCAVIDGNSTTFEHQQPLQDRMFKF

ELTRRLDHDFGKVTKQEVKDFFRWAKDHVVEVEHEFYVKKGGAKKRPAPSDADISEPKRVRESV

AQPSTSDAEASINYADRYQNKCSRHVGMNLMLFPCRQCERMNQNSNICFTHGQKDCLECFPVSE

SQPVSVVKKAYQKLCYIHHIMGKVPDACTACDLVNVDLDDCIFEQ*
```

In some embodiments, the nonsense mutation encodes a UAG codon replacing a codon for lysine and a codon of serine downstream of the p19 promotor of the AAV rep gene.

In some embodiments, the nonsense mutation encodes a codon for serine residues and a UAG codon replacing a codon for lysine in a wild type Rep protein. In some embodiments, the mutant Rep protein comprises a stop codon at position 13 (S13X) and position 240 (K240X) of SEQ ID NO: 2. In some embodiments, the nucleotide sequence encoding the mutant Rep protein S13X-K240X comprises a AGC (37,38,39) TAG and a A719T mutation compared to the wild type Rep gene.

An exemplary nucleotide sequence comprises AGC (37,38,39) TAG and a A719T mutation for encoding a mutant Rep protein is set forth in SEQ ID NO: 11 (mutation site underlined in boldface):

(SEQ ID NO: 11)
ATGCCGGGGTTTTACGAGATTGTGATTAAGGTCCCCTAGGACCTTGACGAGCATCTGCCCGGCA

TTTCTGACAGCTTTGTGAACTGGGTGGCCGAGAAGGAATGGGAGTTGCCGCCAGATTCTGACAT

GGATCTGAATCTGATTGAGCAGGCACCCCTGACCGTGGCCGAGAAGCTGCAGCGCGACTTTCTG

ACGGAATGGCGCCGTGTGAGTAAGGCCCCGGAGGCTCTTTTCTTTGTGCAATTTGAGAAGGGAG

AGAGCTACTTCCACATGCACGTGCTCGTGGAAACCACCGGGGTGAAATCCATGGTTTTGGGACG

TTTCCTGAGTCAGATTCGCGAAAAACTGATTCAGAGAATTTACCAGCGGGATCGAGCCGACTTT

GCCAAACTGGTTCGCGGTCACAAAGACCAGAAATGGCGCCGGAGGCGGGAACAAGGTGGTGGAT

GAGTGCTACATCCCCAATTACTTGCTCCCCAAAACCCAGCCTGAGCTCCAGTGGGCGTGGACTA

ATATGGAACAGTATTTAAGCGCCTGTTTGAATCTCACGGAGCGTAAACGGTTGGTGGCGCAGCA

TCTGACGCACGTGTCGCAGACGCAGGAGCAGAACAAAGAGAATCAGAATCCCAATTCTGATGCG

CCGGTGATCAGATCAAAAACTTCAGCCAGGTACATGGAGCTGGTCGGGTGGCTCGTGGACAAGG

GGATTACCTCGGAGTAGCAGTGGATCCAGGAGGACCAGGCCTCATACATCTCCTTCAATGCGGC

CTCCAACTCGCGGTCCCAAATCAAGGCTGCCTTGGACAATGCGGGAAAGATTATGAGCCTGACT

AAAACCGCCCCCGACTACCTGGTGGGCCAGCAGCCCGTGGAGGACATTTCCAGCAATCGGATTT

ATAAAATTTTGGAACTAAACGGGTACGATCCCCAATATGCGGCTTCCGTCTTTCTGGGATGGGC

CACGAAAAAGTTCGGCAAGAGGAACACCATCTGGCTGTTTGGGCCTGCAACTACCGGGAAGACC

AACATCGCGGAGGCCATAGCCCACACTGTGCCCTTCTACGGGTGCGTAAACTGGACCAATGAGA

ACTTTCCCTTCAACGACTGTGTCGACAAGATGGTGATCTGGTGGGAGGAGGGGAAGATGACCGC

CAAGGTCGTGGAGTCGGCCAAAGCCATTCTCGGAGGAAGCAAGGTGCGCGTGGACCAGAAATGC

AAGTCCTCGGCCCAGATAGACCCGACTCCCGTGATCGTCACCTCCAACACCAACATGTGCGCCG

TGATTGACGGGAACTCAACGACCTTCGAACACCAGCAGCCGTTGCAAGACCGGATGTTCAAATT

TGAACTCACCCGCCGTCTGGATCATGACTTTGGGAAGGTCACCAAGCAGGAAGTCAAAGACTTT

TTCCGGTGGGCAAAGGATCACGTGGTTGAGGTGGAGCATGAATTCTACGTCAAAAAGGGTGGAG

CCAAGAAAAGACCCGCCCCCAGTGACGCAGATATAAGTGAGCCCAAACGGGTGCGCGAGTCAGT

TGCGCAGCCATCGACGTCAGACGCGGAAGCTTCGATCAACTACGCAGACAGGTACCAAAACAAA

TGTTCTCGTCACGTGGGCATGAATCTGATGCTGTTTCCCTGCAGACAATGCGAGAGAATGAATC

AGAATTCAAATATCTGCTTCACTCACGGACAGAAAGACTGTTTAGAGTGCTTTCCCGTGTCAGA

ATCTCAACCCGTTTCTGTCGTCAAAAAGGCGTATCAGAAACTGTGCTACATTCATCATATCATG

GGAAAGGTGCCAGACGCTTGCACTGCCTGCGATCTGGTCAATGTGGATTTGGATGACTGCATCT

TTGAACAATAA

An exemplary amino acid sequence comprises S13X-K240X mutation is set forth in SEQ ID NO: 12 (mutation site underlined in boldface):

(SEQ ID NO: 12)
MPGFYEIVIKVP*****DLDEHLPGISDSFVNWVAEKEWELPPDSDMDLNLIEQAPLTVAEKLQRDFL

TEWRRVSKAPEALFFVQFEKGESYFHMHVLVETTGVKSMVLGRFLSQIREKLIQRIYRGIEPTL

PNWFAVTKTRNGAGGGNKVVDECYIPNYLLPKTQPELQWAWTNMEQYLSACLNLTERKRLVAQH

LTHVSQTQEQNKENQNPNSDAPVIRSKTSARYMELVGWLVDKGITSE*****QWIQEDQASYISFNAA

SNSRSQIKAALDNAGKIMSLTKTAPDYLVGQQPVEDISSNRIYKILELNGYDPQYAASVFLGWA

TKKFGKRNTIWLFGPATTGKTNIAEAIAHTVPFYGCVNWTNENFPFNDCVDKMVIWWEEGKMTA

-continued

KVVESAKAILGGSKVRVDQKCKSSAQIDPTPVIVTSNTNMCAVIDGNSTTFEHQQPLQDRMFKF

ELTRRLDHDFGKVTKQEVKDFFRWAKDHVVEVEHEFYVKKGGAKKRPAPSDADISEPKRVRESV

AQPSTSDAEASINYADRYQNKCSRHVGMNLMLFPCRQCERMNQNSNICFTHGQKDCLECFPVSE

SQPVSVVKKAYQKLCYIHHIMGKVPDACTACDLVNVDLDDCIFEQ*

In some embodiments, the mutant Rep protein comprises a stop codon at position 10 (K10X) and position 238 (S238X) of SEQ ID NO: 2. In some embodiments, the nucleotide sequence encoding the mutant Rep protein K10X-S238X comprises a A28T and a C714A mutation compared to the wild type Rep gene.

An exemplary nucleotide sequence comprises A28T and a C714A mutation for encoding a mutant Rep protein is set forth in SEQ ID NO: 13 (mutation site underlined in boldface):

(SEQ ID NO: 13)

ATGCCGGGGTTTTACGAGATTGTGATTTAGGTCCCCAGCGACCTTGACGAGCATCTGCCCGGCA

TTTCTGACAGCTTTGTGAACTGGGTGGCCGAGAAGGAATGGGAGTTGCCGCCAGATTCTGACAT

GGATCTGAATCTGATTGAGCAGGCACCCCTGACCGTGGCCGAGAAGCTGCAGCGCGACTTTCTG

ACGGAATGGCGCCGTGTGAGTAAGGCCCCGGAGGCTCTTTTCTTTGTGCAATTTGAGAAGGGAG

AGAGCTACTTCCACATGCACGTGCTCGTGGAAACCACCGGGGTGAAATCCATGGTTTTGGGACG

TTTCCTGAGTCAGATTCGCGAAAAACTGATTCAGAGAATTTACCAGCGGGATCGAGCCGACTTT

GCCAAACTGGTTCGCGGTCACAAAGACCAGAAATGGCGCCGGAGGCGGGAACAAGGTGGTGGAT

GAGTGCTACATCCCCAATTACTTGCTCCCCAAAACCCAGCCTGAGCTCCAGTGGGCGTGGACTA

ATATGGAACAGTATTTAAGCGCCTGTTTGAATCTCACGGAGCGTAAACGGTTGGTGGCGCAGCA

TCTGACGCACGTGTCGCAGACGCAGGAGCAGAACAAAGAGAATCAGAATCCCAATTCTGATGCG

CCGGTGATCAGATCAAAAACTTCAGCCAGGTACATGGAGCTGGTCGGGTGGCTCGTGGACAAGG

GGATTACCTAGGAGAAGCAGTGGATCCAGGAGGACCAGGCCTCATACATCTCCTTCAATGCGGC

CTCCAACTCGCGGTCCCAAATCAAGGCTGCCTTGGACAATGCGGGAAAGATTATGAGCCTGACT

AAAACCGCCCCCGACTACCTGGTGGGCCAGCAGCCCGTGGAGGACATTTCCAGCAATCGGATTT

ATAAAATTTTGGAACTAAACGGGTACGATCCCCAATATGCGGCTTCCGTCTTTCTGGGATGGGC

CACGAAAAAGTTCGGCAAGAGGAACACCATCTGGCTGTTTGGGCCTGCAACTACCGGGAAGACC

AACATCGCGGAGGCCATAGCCCACACTGTGCCCTTCTACGGGTGCGTAAACTGGACCAATGAGA

ACTTTCCCTTCAACGACTGTGTCGACAAGATGGTGATCTGGTGGGAGGAGGGGAAGATGACCGC

CAAGGTCGTGGAGTCGGCCAAAGCCATTCTCGGAGGAAGCAAGGTGCGCGTGGACCAGAAATGC

AAGTCCTCGGCCCAGATAGACCCGACTCCCGTGATCGTCACCTCCAACACCAACATGTGCGCCG

TGATTGACGGGAACTCAACGACCTTCGAACACCAGCAGCCGTTGCAAGACCGGATGTTCAAATT

TGAACTCACCCGCCGTCTGGATCATGACTTTGGGAAGGTCACCAAGCAGGAAGTCAAAGACTTT

TTCCGGTGGGCAAAGGATCACGTGGTTGAGGTGGAGCATGAATTCTACGTCAAAAAGGGTGGAG

CCAAGAAAAGACCCGCCCCCAGTGACGCAGATATAAGTGAGCCCAAACGGGTGCGCGAGTCAGT

TGCGCAGCCATCGACGTCAGACGCGGAAGCTTCGATCAACTACGCAGACAGGTACCAAAACAAA

TGTTCTCGTCACGTGGGCATGAATCTGATGCTGTTTCCCTGCAGACAATGCGAGAGAATGAATC

-continued

```
AGAATTCAAATATCTGCTTCACTCACGGACAGAAAGACTGTTTAGAGTGCTTTCCCGTGTCAGA

ATCTCAACCCGTTTCTGTCGTCAAAAAGGCGTATCAGAAACTGTGCTACATTCATCATATCATG

GGAAAGGTGCCAGACGCTTGCACTGCCTGCGATCTGGTCAATGTGGATTTGGATGACTGCATCT

TTGAACAATAA
```

An exemplary amino acid sequence comprises K10X-S238X mutation is set forth in SEQ ID NO: 14 (mutation site underlined in boldface):

```
                                                    (SEQ ID NO: 14)
MPGFYEIVI*VPSDLDEHLPGISDSFVNWVAEKEWELPPDSDMDLNLIEQAPLTVAEKLQRDFL

TEWRRVSKAPEALFFVQFEKGESYFHMHVLVETTGVKSMVLGRFLSQIREKLIQRIYRGIEPTL

PNWFAVTKTRNGAGGGNKVVDECYIPNYLLPKTQPELQWAWTNMEQYLSACLNLTERKRLVAQH

LTHVSQTQEQNKENQNPNSDAPVIRSKTSARYMELVGWLVDKGIT*EKQWIQEDQASYISFNAA

SNSRSQIKAALDNAGKIMSLTKTAPDYLVGQQPVEDISSNRIYKILELNGYDPQYAASVFLGWA

TKKFGKRNTIWLFGPATTGKTNIAEAIAHTVPFYGCVNWTNENFPFNDCVDKMVIWWEEGKMTA

KVVESAKAILGGSKVRVDQKCKSSAQIDPTPVIVTSNTNMCAVIDGNSTTFEHQQPLQDRMFKF

ELTRRLDHDFGKVTKQEVKDFFRWAKDHVVEVEHEFYVKKGGAKKRPAPSDADISEPKRVRESV

AQPSTSDAEASINYADRYQNKCSRHVGMNLMLFPCRQCERMNQNSNICFTHGQKDCLECFPVSE

SQPVSVVKKAYQKLCYIHHIMGKVPDACTACDLVNVDLDDCIFEQ*
```

It is also within the scope of the present disclosure that other permutations of mutant rep gene can be adopted to the method of AAV production described herein. In some embodiments, when the synthetic suppressor tRNA or read through small molecule are not present in the host cell for rAAV production, the translation of the Rep protein would be stopped at the premature stop codon, thus producing no functional Rep protein. In some embodiments, when the synthetic suppressor tRNA described herein are not present in the host cell for rAAV production, the translation of the Rep protein would be stopped at the premature stop codon, thus producing no functional Rep gene. In other embodiments, when the synthetic suppressor tRNA or read through small molecule are present in the host cell for rAAV production, the translation of the Rep protein would read through the premature stop codon, thus producing a functional Rep protein.

Synthetic Suppressor tRNAs

Aspects of the disclosure relate to transfer RNAs (tRNAs). A "transfer RNA (tRNA)" is a oligoribonucleotide that is between about 70 and 90 nucleotides in length, binds to a messenger RNA (mRNA), and in doing so carries an amino acid to a ribosome whereupon the amino acid is added to a polypeptide chain. The cloverleaf structure of tRNAs typically comprises a 5' terminal phosphate group, a 7-9 base pair acceptor stem (which contains a CCA-3'-terminal group to which the amino acid is attached), a "D loop" comprising a 4-6 base pair stem ending in a loop, a "T-loop" comprising a 4-5 base pair stem that includes a pseudouridine, and an anticodon arm comprising a 5 base pair stem ending in a loop containing an anticodon (a three nucleotide sequence that binds to a codon of mRNA). The structure of tRNAs is known and described, for example by Sharp et al. *Crit. Rev. Biochem.* 19:107 144 (1985).

In some embodiments, a transfer RNA is a synthetic suppressor tRNA. As used herein, a "synthetic suppressor tRNA" refers to a transfer RNA that has been configured (e.g., modified) to bind to a termination codon. Without wishing to be bound by any particular theory, in some embodiments, synthetic suppressor tRNAs described herein are configured to allow for "read-through" of a premature termination codon, thus allowing production of a functional or partially functional protein from the gene containing the mutation causing the premature termination codon.

A synthetic suppressor tRNA can bind any termination codon, for example an amber codon (UAG), an ochre codon (UAA), or an opal codon (UGA). In some embodiments, a synthetic suppressor tRNA comprises an anticodon that binds to a termination codon (e.g., UAG, UAA, UGA). In some embodiments, a synthetic suppressor tRNA comprises an anticodon region configured to recognize a nonsense mutation in a gene (e.g., a nonsense mutation that results in the gene having a premature termination codon). In some embodiments, a synthetic suppressor tRNA preferentially binds to a premature termination codon relative to a normal stop codon (e.g., a stop codon upstream of a polyA tail of an mRNA). Methods of producing and testing synthetic suppressor tRNAs are known, for example as described by Lueck et al. *Nature Communications* 10:822 2019.

An anticodon (e.g., an anticodon of a synthetic suppressor tRNA) that binds to a termination codon may be a cognate anticodon (e.g., the anticodon forms three base pairs with the termination codon) or a near-cognate anticodon (e.g., the anticodon forms two base pairs with the termination codon). Examples of near-cognate tRNAs are shown below in Table 1.

TABLE 1

Near-cognate tRNAs and their charged amino acid

| Near Cognate tRNAs | | |
|---|---|---|
| UAA | UAG | UGA |
| AAA - Lys | AAG - Lys | AGA - Arg |
| CAA - Gln | CAG - Gln | CGA - Arg |

TABLE 1-continued

| Near-cognate tRNAs and their charged amino acid Near Cognate tRNAs | | |
|---|---|---|
| UAA | UAG | UGA |
| GAA - Glu | GAG - Glu | GGA - Gly |
| UCA - Ser | UCG - Ser | UCA - Ser |
| UUA - Leu | UGG - Trp | UUA - Leu |
| UAC - Tyr | UUG - Leu | UGC - Cys |
| UAU - Tyr | UAC - Tyr | UGG - Trp |
| | UAU - Tyr | UGU - Cys |

A synthetic suppressor tRNA may be charged with any amino acid. As used herein, a "charged" tRNA refers to a tRNA that has been chemically bonded to its cognate amino acid. In some embodiments, a tRNA is charged with a natural amino acid (e.g., Ala, Arg, Asn, Asp, Cys, Gln, Glu, Gly, His, Ile, Leu, Lys, Met, Phe, Pro, Ser, Thr, Trp, Tyr, Val). In some embodiments, a tRNA is charged with an unnatural amino acid (e.g., a non-alpha amino acid, a D-amino acid, a dehydroamino acid, selenol amino acids, etc.). In some embodiments, a tRNA is charged with non-canonical amino acid (ncAA), such as, for example, $N^{\varepsilon}$-2-azidoethyloxycarbonyl-L-lysine (NAEK).

In some embodiments, binding of a synthetic suppressor tRNA described by the disclosure to a premature termination codon of an mRNA causes "read-through" of the premature stop codon by a ribosome and results in production of a full-length or functional protein. In some embodiments, "read-through" of an mRNA causes an increase in protein level or activity in a cell or subject that ranges from about 0.1% to about 100% (e.g., an increase of about 0.1%, 0.5%, 1.0%, 2%, 5%, 10%, 25%, 50%, 75%, or 100%) relative to protein expression or activity of an mRNA that has not been contacted with the synthetic suppressor tRNA. In some embodiments, "read-through" of an mRNA causes an increase in protein level or activity of more than 100% (e.g., 200%, 500%, 1000%, etc.) in a cell or subject.

In some embodiments, an orthogonal aminoacyl-tRNA synthetase is provided to a host cell. In some embodiments, "orthogonal" refers to functional molecules that function poorly or not at all with endogenous components of a cell, when compared to a corresponding molecule that is endogenous to the cell. For example, an "orthogonal aminoacyl-tRNA synthetase (aaRS)" is an enzyme that preferentially aminoacylates a corresponding tRNA with a non-canonical amino acid (ncAA) that is supplied to the host cell.

In some embodiments, non-canonical amino acids are used with aaRSs. See for example, S. Hunt, The Non-Protein Amino Acids: In Chemistry and Biochemistry of the Amino Acids, edited by G. C. Barrett, Chapman and Hall, 1985. Some examples of non-canonical amino acids are Ne-2-azidoethyloxycarbonyl-L-lysine (NAEK), cyclopropene-L-lysine (CpK), Boc-lysine, 4-hydroxyproline, desmosine, gamma-aminobutyric acid, beta-cyanoalanine, norvaline, 4-(E)-butenyl-4 (R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)$C_6H_5$; —$CF_3$; —CN; -halo; —$NO_2$; $CH_3$), disubstituted phenylalanines, substituted tyrosines (e.g., further substituted with —C(=O)$C_6H_5$; —$CF_3$; —CN; -halo; —$NO_2$; $CH_3$), or statine. Additionally, the amino acids suitable for use in the present invention may be derivatized to include amino acid residues that are hydroxylated, phosphorylated, sulfonated, acylated, and glycosylated, to name a few. Examples of non-canonical amino acids can be found in S. Hunt, The Non-Protein Amino Acids: In Chemistry and Biochemistry of the Amino Acids, edited by G. C. Barrett, Chapman and Hall, 1985.

Read-Through Small Molecules

Aspects of the disclosure relate to small molecules capable of facilitating the "read-through" of a premature termination codon of an mRNA. A "small molecule", as used herein, refers to molecules, whether naturally-occurring or artificially created (e.g., via chemical synthesis) that have a relatively low molecular weight. Typically, a small molecule is an organic compound (e.g., it contains carbon). The small molecule may contain multiple carbon-carbon bonds, stereocenters, and other functional groups (e.g., amines, hydroxyl, carbonyls, and heterocyclic rings, etc.). In certain aspects, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain aspects, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain aspects, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. In certain aspects, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In some embodiments, a small molecule is an aminoglycoside (e.g., G418), pthalimide derivative (e.g., CDX5-1), etc.

In some embodiments, the small molecules described herein are compounds that potentiate read-through at multiple nonsense codons. In some embodiments, the small molecules described herein are compounds that potentiate read-through at premature stop codons. In some embodiments, the small molecules described herein are compounds that potentiate read-through UAG, UAA, or UGA codons. Small molecules capable of potentiate read-through of nonsense codons have been previously described. (see e.g., Baradaran-Heravi et al., Novel small molecules potentiate premature termination codon readthrough by aminoglycosides, *Nucleic Acids Res.* 2016 Aug. 19; 44 (14): 6583-98; Du el al., A new series of small molecular weight compounds induce read through of all three types of nonsense mutations in the ATM gene, *Mol Ther.* 2013 September; 21 (9): 1653-60; Dabrowski et al., Advances in therapeutic use of a drug-stimulated translational readthrough of premature termination codons, *Molecular Medicine* volume 24, Article number: 25 (2018), etc.).

rAAV Production Systems

The disclosure relates, in some embodiments, to isolated nucleic acids (e.g., vectors comprising one or more isolated nucleic acids) that are useful for replication and packaging of rAAVs.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein. Furthermore, nucleic acids can be tailored for optimal gene expression based on optimization of nucleotide sequence to reflect the codon bias of a host cell. The skilled artisan appreciates that gene expression may be improved if codon usage is biased towards those codons favored by the host.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

In some aspects, the disclosure provides a recombinant adeno-virus (rAAV) production system comprising a first vector comprising one or more nucleic acids encoding: a non-beta-lactam antibiotic resistance gene, an inducible eukaryotic promoter (e.g., a steroid-inducible eukaryotic promoter), an adeno-associated virus (AAV) capsid protein, wherein the nucleic acid encoding the capsid protein is flanked by one or more restriction enzyme recognition sites, and one or more viral helper elements, for example one or more Adenovirus helper elements selected from Ad-VA, Ad-E2a, Ad-E2b, and Ad-E4.

In some embodiments, a vector as described by the disclosure comprises a nucleic acid sequence encoding one or more antibiotic-resistance genes. An "antibiotic-resistance gene" refers to a nucleic acid that encodes a gene product that enables a cell (e.g., a bacterial cell, a mammalian cell, etc.) to survive in the presence of an antibiotic agent that would otherwise kill the cell and/or kills cells that do not express the antibiotic resistance gene. Examples of antibiotic agents include but are not limited to cytotoxic agents (e.g., antibiotic agents affecting mammalian cells), antifungal agents, antiviral agents, and antibacterial (e.g., bacteriostatic and bactericidal agents). In some embodiments, an antibiotic-resistance gene confers resistance of a cell to an antibacterial agent. Examples of antibacterial agents include but are not limited to kanamycin, spectinomycin, streptomycin, ampicillin, carbenicillin, bleomycin, erythromycin, polymixin B, tetracycline, and chloramphenicol. In some embodiments, an antibiotic agent is a beta-lactam antibiotic (e.g., antibiotic agent having a beta-lactam ring).

Examples of beta-lactam antibiotics include but are not limited to penicillin derivatives (penams, such as benzathine penicillin, benzylpenicillin (penicillin G), phenoxymethylpenicillin (penicillin V), cloxacillin, dicloxacillin, flucloxacillin, methicillin, nafcillin, oxacillin, temocillin, etc.), cephalosporins (cephems, such as cefazolin, cephalexin, cephalosporin C, cephalothin, cefixime, cefotaxime, cefpodoxime, ceftazidime, ceftriaxone, cefepime, cefpirome, etc.), monobactams, carbapenems, ampicillin, amoxicillin, etc. In some embodiments, an antibiotic-resistance gene is not an ampicillin antibiotic resistance gene (e.g., AmpR). In some embodiments, a vector as described by the disclosure comprises a nucleic acid encoding an antibiotic-resistance gene selected from kanR, bsd (Blasticidin resistance gene), neo (G418/Geneticin resistance gene), hygB (Hygromycin resistance gene), pac (Puromycin resistance gene), and sh bla (Zeocin resistance gene).

In some embodiments, a vector as described by the disclosure comprises a nucleic acid encoding a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. A promoter may be a constitutive promoter, inducible promoter, or a tissue-specific promoter. In some embodiments, the promoter is an AAV p19 promoter. In some embodiments, the promoter is an AAV p5 promoter.

In some embodiments, the promoter is an inducible promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter (e.g., MMTV Long Terminal Repeat (MMTV LTR) promoter), the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268: 1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)).

In some embodiments the promoter is a steroid-inducible promoter, for example a promoter comprising a hormone binding domain (HBD) of a glucocorticoid receptor (GR), for example a MMTV LTR promoter. In some embodiments, a steroid-inducible promoter allows for increased expression of AAV Cap proteins relative to AAV Rep proteins (e.g., Rep 78/68 and Rep 52/40).

Still other types of inducible promoters which may be useful in this context are those which are regulated by a specific physiological state, e.g., temperature, acute phase, a particular differentiation state of the cell, or in replicating cells only.

In some embodiments, a vector as described by the disclosure comprises a nucleic acid encoding an adeno-associated virus (AAV) capsid protein. The AAV capsid is an important element in determining tissue-specific targeting capabilities of an rAAV. Thus, an rAAV having a capsid appropriate for the tissue being targeted can be selected. Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins. However, in some embodiments, the rep gene is not functional when it is introduced to the host cell because it contains one or more stop-mutations or frameshift mutations that suppresses expression of one or more of the rep genes. In such systems, in some embodiments, the use of anticodon engineered synthetic suppressor tRNAs or orthogonal aminoacyl-tRNA synthetase-tRNA pairs with supplied ncAAs allows for the functional expression of the rep gene. In some embodiments, the use of a read-through small molecule allows for the functional expression of the rep gene. In some embodiments the capsid protein is of a serotype selected from: AAV1, AAV2, AAV3, AAV3B, AAV4, AAV5, AAV6, AAV7, AAV8, AAV9, AAV10, AAV11, AAV12, AAV.rh.10 and variants of any one of them. Generally, AAV capsid proteins (e.g., VP1, VP2 and VP3 capsid proteins) are encoded by a single Cap gene.

In some aspects, the disclosure relates to vector systems that are configured to allow the capsid protein encoded by the vector to be changed easily (e.g., vectors described by the disclosure allow for a nucleic acid encoding a particular serotype capsid protein to be easily swapped for a nucleic acid sequence encoding a capsid protein having a different serotype). Accordingly, in some embodiments, the nucleic acid encoding the capsid protein is flanked by one or more (e.g., 2, 3, 4, 5, 6, 7, 8, 9, 10, or more) restriction enzyme recognition sites. Examples of restriction enzymes and their recognition sites include SwaI (5'ATTTAAAT3'), ClaI (5'ATCGAT3'), EcoRI (5'GAATTC3'), BamHI (5'GGATCC3'), NotI (5'GCGGCCGC3'), etc.

Further examples of restriction enzymes and their cognate recognition sites are described, for example, by neb.com/tools-and-resources/selection-charts/alphabetized-list-of-recognition-specificities, the entire contents of which are incorporated herein by reference.

In some embodiments, restriction enzyme recognition sites flanking the nucleic acid sequence encoding the capsid protein are cleaved by the same restriction enzyme. In some embodiments, restriction enzyme recognition sites flanking the nucleic acid sequence encoding the capsid protein are cleaved by different (e.g., 2 or more) restriction enzymes.

In some embodiments, a nucleic acid encoding an AAV capsid protein is flanked by two SwaI restriction sites, two ClaI restriction sites, or an SwaI restriction site and a ClaI restriction site. The skilled artisan will recognize that the orientation of the SwaI and ClaI restriction sites may vary with respect to the nucleic acid sequence encoding the capsid protein. For example, in some embodiments, a ClaI restriction site is located 5' to a nucleic acid encoding a capsid protein and a SwaI restriction site is located 3' to the nucleic acid encoding the capsid protein. In some embodiments, an SwaI restriction site is located 5' to a nucleic acid encoding a capsid protein and a ClaI restriction site is located 3' to the nucleic acid encoding the capsid protein.

In some embodiments, the nucleic acid described herein further comprises regulatory sequences that regulates the activity of the promoter, thereby regulating the expression level of the rep/cap gene. In some embodiments, the regulatory sequence is a stuffer sequence. A stuffer sequence, as used herein, refers to a nucleic acid sequence capable of regulating the expression level of the rep/cap protein in the host cell by regulating the activity of the promoter (e.g., the P5 promoter).

In some embodiments, the nucleic acid encoding the rep and/or cap gene can be flanked by a pair of insulator sequences. The insulator sequence is used to prevent the activation of the nearby genes where the nucleic acid is integrated in the genome.

In some embodiments, the nucleic acid described herein is integrated into the genome of the host cell. Any suitable known method in the art can be used to integrating the nucleic acid into the genome of the host cell. In some embodiments, the integration is achieved by piggybac transposon system.

In some embodiments, the nucleic acid described herein comprises a nucleic acid sequence at least 60%, at least 70%, at least 80%, at least 85%, at least 90%, at least 91%, at least 92%, at least 93%, at least 94%, at least 95%, at least 96%, at least 97%, at least 98%, at least 99%, or 100% identical to nucleic acid sequences as set forth in SEQ ID NOs: 15-18.

An exemplary nucleic acid sequence encoding a mutant rep (C714A, bold and underlined)/Cap gene with the stuffer sequence (underlined) and insulator sequence (bold) is set forth in SEQ ID NO: 15:

CCCTAGAAAGATAATCATATTGTGACGTACGTTAAAGATAATCATGTGTAAAATTGACGCATGT

GTTTTATCGGTCTGTATATCGAGGTTTATTTATTAATTTGAATAGATATTAAGTTTTATTATAT

TTACACTTACATACTAATAATAAATTCAACAAACAATTTATTTATGTTTATTTATTTATTAAAA

AAAACAAAAACTCAAAATTTCTTCTATAAAGTAACAAAACTTTTATGAGGGACAGCCCCCCCCC

AAAGCCCCCAGGGATGTAATTACGTCCCTCCCCCGCTAGGGGGCAGCAGCGAGCCGCCCGGGGC

TCCGCTCCGGTCCGGCGCTCCCCCCGCATCCCCGAGCCGGCAGCGTGCGGGGACAGCCCGGGCA

CGGGGAAGGTGGCACGGGATCGCTTTCCTCTGAACGCTTCTCGCTGCTCTTTGAGCCTGCAGAC

ACCTGGGGGGATACGGGGAAAAGGCTAGAGGTCCTGTATTAGAGGTCACGTGAGTGTTTTGCGA

CATTTTGCGACACCATGTGGTCACGCTGGGTATTTAAGCCCGAGTGAGCACGCAGGGTCTCCAT

TTTGAAGCGGGAGGTTTGAACGCGCAGCCGCCAAGCCGAATTCTGCAGATATCCCCGAGTCCTT

CAATGCTATCATTCCCTTTGATATTGGACCATATGCATAGTACCGAGAAACTAGTGCGAAGTAG

TGATCAGGTATTGCTGTTAGATATCCCCGAGTCCTTCAATGCTATCATTCTCTTTGATATTGGA

CCATATGCATAGTACCGAGAAACTAGTGCGAAGTAGTGATCAGGTATTGCTGTTAGATATCCCC

GAGTCCTTCAATGCTATCATTCCCTTTGATATTGGACCATATGCATAGTACCGAGAAACTAGTG

CGAAGTAGTGATCAGGTATTGCTGTTAGATATCCCCGAGTCCTTCAATGCTATCATTCTCTTTG

ATATTGGACCATATGCATAGTACCGAGAAACTAGTGCGAAGTAGTGATCAGGTATTGCTGTTAG

ATATCCCCGAGTCCTTCAATGCTATCATTCCCTTTGATATTGGACCATATGCATAGTACCGAGA

AACTAGTGCGAAGTAGTGATCAGGTATTGCTGTTAGATATCCCCGAGTCCTTCAATGCTATCAT

TTCCTTTGATATTGGATCATATGCATAGTACCGAGAAACTAGTGCGAAGTAGTGATCAGGTATT

GCTGTTAAGGATCCATCACACTGGCGGCCGCTCGAGGGGAGCTCGCAGGGTCTCCATTTTGAAG

CGGGAGGTTTGAACGCGCAGCCGCCATGCCGGGGTTTTACGAGATTGTGATTAAGGTCCCCAGC

GACCTTGACGAGCATCTGCCCGGCATTTCTGACAGCTTTGTGAACTGGGTGGCCGAGAAGGAAT

GGGAGTTGCCGCCAGATTCTGACATGGATCTGAATCTGATTGAGCAGGCACCCCTGACCGTGGC

CGAGAAGCTGCAGCGCGACTTTCTGACGGAATGGCGCCGTGTGAGTAAGGCCCCGGAGGCTCTT

TTCTTTGTGCAATTTGAGAAGGGAGAGAGCTACTTCCACATGCACGTGCTCGTGGAAACCACCG

GGGTGAAATCCATGGTTTTGGGACGTTTCCTGAGTCAGATTCGCGAAAAACTGATTCAGAGAAT

TTACCAGCGGGATCGAGCCGACTTTGCCAAACTGGTTCGCGGTCACAAAGACCAGAAATGGCGC

CGGAGGCGGGAACAAGGTGGTGGATGAGTGCTACATCCCCAATTACTTGCTCCCCAAAACCCAG

CCTGAGCTCCAGTGGGCGTGGACTAATATGGAACAGTATTTAAGCGCCTGTTTGAATCTCACGG

AGCGTAAACGGTTGGTGGCGCAGCATCTGACGCACGTGTCGCAGACGCAGGAGCAGAACAAAGA

GAATCAGAATCCCAATTCTGATGCGCCGGTGATCAGATCAAAAACTTCAGCCAGGTACATGGAG

CTGGTCGGGTGGCTCGTGGACAAGGGGATTACCTAGGAGAAGCAGTGGATCCAGGAGGACCAGG

CCTCATACATCTCCTTCAATGCGGCCTCCAACTCGCGGTCCCAAATCAAGGCTGCCTTGGACAA

TGCGGGAAAGATTATGAGCCTGACTAAAACCGCCCCCGACTACCTGGTGGGCCAGCAGCCCGTG

GAGGACATTTCCAGCAATCGGATTTATAAAATTTTGGAACTAAACGGGTACGATCCCCAATATG

CGGCTTCCGTCTTTCTGGGATGGGCCACGAAAAAGTTCGGCAAGAGGAACACCATCTGGCTGTT

-continued

```
TGGGCCTGCAACTACCGGGAAGACCAACATCGCGGAGGCCATAGCCCACACTGTGCCCTTCTAC

GGGTGCGTAAACTGGACCAATGAGAACTTTCCCTTCAACGACTGTGTCGACAAGATGGTGATCT

GGTGGGAGGAGGGGAAGATGACCGCCAAGGTCGTGGAGTCGGCCAAAGCCATTCTCGGAGGAAG

CAAGGTGCGCGTGGACCAGAAATGCAAGTCCTCGGCCCAGATAGACCCGACTCCCGTGATCGTC

ACCTCCAACACCAACATGTGCGCCGTGATTGACGGGAACTCAACGACCTTCGAACACCAGCAGC

CGTTGCAAGACCGGATGTTCAAATTTGAACTCACCCGCCGTCTGGATCATGACTTTGGGAAGGT

CACCAAGCAGGAAGTCAAAGACTTTTTCCGGTGGGCAAAGGATCACGTGGTTGAGGTGGAGCAT

GAATTCTACGTCAAAAAGGGTGGAGCCAAGAAAAGACCCGCCCCCAGTGACGCAGATATAAGTG

AGCCCAAACGGGTGCGCGAGTCAGTTGCGCAGCCATCGACGTCAGACGCGGAAGCTTCGATCAA

CTACGCAGACAGGTACCAAAACAAATGTTCTCGTCACGTGGGCATGAATCTGATGCTGTTTCCC

TGCAGACAATGCGAGAGAATGAATCAGAATTCAAATATCTGCTTCACTCACGGACAGAAAGACT

GTTTAGAGTGCTTTCCCGTGTCAGAATCTCAACCCGTTTCTGTCGTCAAAAAGGCGTATCAGAA

ACTGTGCTACATTCATCATATCATGGGAAAGGTGCCAGACGCTTGCACTGCCTGCGATCTGGTC

AATGTGGATTTGGATGACTGCATCTTTGAACAATAAATGATTTAAATCAGGTATGGCTGCCGAT

GGTTATCTTCCAGATTGGCTCGAGGACACTCTCTCTGAAGGAATAAGACAGTGGTGGAAGCTCA

AACCTGGCCCACCACCACCAAAGCCCGCAGAGCGGCATAAGGACGACAGCAGGGGTCTTGTGCT

TCCTGGGTACAAGTACCTCGGACCCTTCAACGGACTCGACAAGGGAGAGCCGGTCAACGAGGCA

GACGCCGCGGCCCTCGAGCACGACAAAGCCTACGACCGGCAGCTCGACAGCGGAGACAACCCGT

ACCTCAAGTACAACCACGCCGACGCGGAGTTTCAGGAGCGCCTTAAAGAAGATACGTCTTTTGG

GGGCAACCTCGGACGAGCAGTCTTCCAGGCGAAAAAGAGGGTTCTTGAACCTCTGGGCCTGGTT

GAGGAACCTGTTAAGACGGCTCCGGGAAAAAAGAGGCCGGTAGAGCACTCTCCTGTGGAGCCAG

ACTCCTCCTCGGGAACCGGAAAGGCGGGCCAGCAGCCTGCAAGAAAAAGATTGAATTTTGGTCA

GACTGGAGACGCAGACTCAGTACCTGACCCCCAGCCTCTCGGACAGCCACCAGCAGCCCCCTCT

GGTCTGGGAACTAATACGATGGCTACAGGCAGTGGCGCACCAATGGCAGACAATAACGAGGGCG

CCGACGGAGTGGGTAATTCCTCGGGAAATTGGCATTGCGATTCCACATGGATGGGCGACAGAGT

CATCACCACCAGCACCCGAACCTGGGCCCTGCCCACCTACAACAACCACCTCTACAAACAAATT

TCCAGCCAATCAGGAGCCTCGAACGACAATCACTACTTTGGCTACAGCACCCCTTGGGGGTATT

TTGACTTCAACAGATTCCACTGCCACTTTTCACCACGTGACTGGCAAAGACTCATCAACAACAA

CTGGGGATTCCGACCCAAGAGACTCAACTTCAAGCTCTTTAACATTCAAGTCAAAGAGGTCACG

CAGAATGACGGTACGACGACGATTGCCAATAACCTTACCAGCACGGTTCAGGTGTTTACTGACT

CGGAGTACCAGCTCCCGTACGTCCTCGGCTCGGCGCATCAAGGATGCCTCCCGCCGTTCCCAGC

AGACGTCTTCATGGTGCCACAGTATGGATACCTCACCCTGAACAACGGGAGTCAGGCAGTAGGA

CGCTCTTCATTTTACTGCCTGGAGTACTTTCCTTCTCAGATGCTGCGTACCGGAAACAACTTTA

CCTTCAGCTACACTTTTGAGGACGTTCCTTTCCACAGCAGCTACGCTCACAGCCAGAGTCTGGA

CCGTCTCATGAATCCTCTCATCGACCAGTACCTGTATTACTTGAGCAGAACAAACACTCCAAGT

GGAACCACCACGCAGTCAAGGCTTCAGTTTTCTCAGGCCGGAGCGAGTGACATTCGGGACCAGT

CTAGGAACTGGCTTCCTGGACCCTGTTACCGCCAGCAGCGAGTATCAAAGACATCTGCGGATAA

CAACAACAGTGAATACTCGTGGACTGGAGCTACCAAGTACCACCTCAATGGCAGAGACTCTCTG

GTGAATCCGGGCCCGGCCATGGCAAGCCACAAGGACGATGAAGAAAAGTTTTTTCCTCAGAGCG

GGGTTCTCATCTTTGGGAAGCAAGGCTCAGAGAAAACAAATGTGGACATTGAAAAGGTCATGAT

TACAGACGAAGAGGAAATCAGGACAACCAATCCCGTGGCTACGGAGCAGTATGGTTCTGTATCT
```

-continued

ACCAACCTCCAGAGAGGCAACAGACAAGCAGCTACCGCAGATGTCAACACACAAGGCGTTCTTC

CAGGCATGGTCTGGCAGGACAGAGATGTGTACCTTCAGGGGCCCATCTGGGCAAAGATTCCACA

CACGGACGGACATTTTCACCCCTCTCCCCTCATGGGTGGATTCGGACTTAAACACCCTCCTCCA

CAGATTCTCATCAAGAACACCCCGGTACCTGCGAATCCTTCGACCACCTTCAGTGCGGCAAAGT

TTGCTTCCTTCATCACACAGTACTCCACGGGACAGGTCAGCGTGGAGATCGAGTGGGAGCTGCA

GAAGGAAAACAGCAAACGCTGGAATCCCGAAATTCAGTACACTTCCAACTACAACAAGTCTGTT

AATGTGGACTTTACTGTGGACACTAATGGCGTGTATTCAGAGCCTCGCCCCATTGGCACCAGAT

ACCTGACTCGTAATCTGTAATTGCTTGTTAATCAATAAACCGTTTAATTCGTTTCAGTTGAACT

TTGGTCTCTGCGTATTTCTTTCTTATCTAGTTTCCATGCTCCTCCACGGCCAAGGATCTGCGAT

CGCTCCGGTGCCCGTCAGTGGGCAGAGCGCACATCGCCCACAGTCCCCGAGAAGTTGGGGGGAG

GGGTCGGCAATTGAACGGGTGCCTAGAGAAGGTGGCGCGGGGTAAACTGGGAAAGTGATGTCGT

GTACTGGCTCCGCCTTTTTCCCGAGGGTGGGGGAGAACCGTATATAAGTGCAGTAGTCGCCGTG

AACGTTCTTTTTCGCAACGGGTTTGCCGCCAGAACACAGCTGAAGCTTCGAGGGGCTCGCATCT

CTCCTTCACGCGCCCGCCGCCCTACCTGAGGCCGCCATCCACGCCGGTTGAGTCGCGTTCTGCC

GCCTCCCGCCTGTGGTGCCTCCTGAACTGCGTCCGCCGTCTAGGTAAGTTTAAAGCTCAGGTCG

AGACCGGGCCTTTGTCCGGCGCTCCCTTGGAGCCTACCTAGACTCAGCCGGCTCTCCACGCTTT

GCCTGACCCTGCTTGCTCAACTCTACGTCTTTGTTTCGTTTTCTGTTCTGCGCCGTTACAGATC

CAAGCTGTGACCGGCGCCTACTCTAGAGCTAGCGAATTCGAATTTAAATCGGATCCGCGGCCGC

GCCCCTCTCCCTCCCCCCCCCCTAACGTTACTGGCCGAAGCCGCTTGGAATAAGGCCGGTGTGC

GTTTGTCTATATGTTATTTTCCACCATATTGCCGTCTTTTGGCAATGTGAGGGCCCGGAAACCT

GGCCCTGTCTTCTTGACGAGCATTCCTAGGGGTCTTTCCCCTCTCGCCAAAGGAATGCAAGGTC

TGTTGAATGTCGTGAAGGAAGCAGTTCCTCTGGAAGCTTCTTGAAGACAAACAACGTCTGTAGC

GACCCTTTGCAGGCAGCGGAACCCCCCACCTGGCGACAGGTGCCTCTGCGGCCAAAAGCCACGT

GTATAAGATACACCTGCAAAGGCGGCACAACCCCAGTGCCACGTTGTGAGTTGGATAGTTGTGG

AAAGAGTCAAATGGCTCTCCTCAAGCGTATTCAACAAGGGGCTGAAGGATGCCCAGAAGGTACC

CCATTGTATGGGATCTGATCTGGGGCCTCGGTGCACATGCTTTACATGTGTTTAGTCGAGGTTA

AAAAAACGTCTAGGCCCCCCGAACCACGGGGACGTGGTTTTCCTTTGAAAAACACGATGATAAT

ATGGCCACAACCATGGCGTCCGGAATGATTGAACAAGATGGATTGCACGCAGGTTCTCCGGCCG

CTTGGGTGGAGAGGCTATTCGGCTATGACTGGGCACAACAGACAATCGGCTGCTCTGATGCCGC

CGTGTTCCGGCTGTCAGCGCAGGGGCGCCCGGTTCTTTTTGTCAAGACCGACCTGTCCGGTGCC

CTGAATGAACTGCAGGACGAGGCAGCGCGGCTATCGTGGCTGGCCGCGACGGGCGTTCCTTGCG

CAGCTGTGCTCGACGTTGTCACTGAAGCGGGAAGGGACTGGCTGCTATTGGGCGAAGTGCCGGG

GCAGGATCTCCTGTCATCTCACCTTGCTCCTGCCGAGAAAGTATCCATCATGGCTGATGCAATG

CGGCGGCTGCATACGCTTGATCCGGCTACCTGCCCATTCGACCACCAAGCGAAACATCGCATCG

AGCGAGCACGTACTCGGATGGAAGCCGGTCTTGTCGATCAGGATGATCTGGACGAAGAGCATCA

GGGGCTCGCGCCAGCCGAACTGTTCGCCAGGCTCAAGGCGCGCATGCCCGACGGCGAGGATCTC

GTCGTGACCCATGGCGATGCCTGCTTGCCGAATATCATGGTGGAAAATGGCCGCTTTTCTGGAT

TCATCGACTGTGGCCGGCTGGGTGTGGCGGACCGCTATCAGGACATAGCGTTGGCTACCCGTGA

TATTGCTGAAGAGCTTGGCGGCGAATGGGCTGACCGCTTCCTCGTGCTTTACGGTATCGCCGCT

CCCGATTCGCAGCGCATCGCCTTCTATCGCCTTCTTGACGAGTTCTTCTGAGTCGACAATCAAC

-continued

CTCTGGATTACAAAATTTGTGAAAGATTGACTGGTATTCTTAACTATGTTGCTCCTTTTACGCT

ATGTGGATACGCTGCTTTAATGCCTTTGTATCATGCGTTAACTAAACTTGTTTATTGCAGCTTA

TAATGGTTACAAATAAAGCAATAGCATCACAAATTTCACAAATAAAGCATTTTTTTCACTGCAT

TCTAGTTGTGGTTTGTCCAAACTCATCAATGTATCTTATCATGTCTGGAATTGACTCAAATGAT

GTCAATTAGTCTATCAGAAGCTCATCTGGTCTCCCTTCCGGGGGACAAGACATCCCTGTTTAAT

ATTTAAACAGCAGTGTTCCCAAACTGGGTTCTTATATCCCTTGCTCTGGTCAACCAGGTTGCAG

GGTTTCCTGTCCTCACAGGAACGAAGTCCCTAAAGAAACAGTGGCAGCCAGGTTTAGCCCCGGA

ATTGACTGGATTCCTTTTTTAGGGCCCATTGGTATGGCTTTTTCCCCGTATCCCCCCAGGTGTC

TGCAGGCTCAAAGAGCAGCGAGAAGCGTTCAGAGGAAAGCGATCCCGTGCCACCTTCCCCGTGC

CCGGGCTGTCCCCGCACGCTGCCGGCTCGGGGATGCGGGGGGAGCGCCGGACCGGAGCGGAGCC

CCGGGCGGCTCGCTGCTGCCCCCTAGCGGGGGAGGGACGTAATTACATCCCTGGGGGCTTTGGG

GGGGGGCTGTCCCTGATATCTATAACAAGAAAATATATATATAATAAGTTATCACGTAAGTAGA

ACATGAAATAACAATATAATTATCGTATGAGTTAAATCTTAAAAGTCACGTAAAAGATAATCAT

GCGTCATTTTGACTCACGCGGTCGTTATAGTTCAAAATCAGTGACACTTACCGCATTGACAAGC

ACGCCTCACGGGAGCTCCAAGCGGCGACTGAGATGTCCTAAATGCACAGCGACGGATTCGCGCT

ATTTAGAAAGAGAGAGCAATATTTCAAGAATGCATGCGTCAATTTTACGCAGACTATCTTTCTA

GGG

An exemplary nucleic acid sequence encoding a mutant rep (C714A, bold and underlined)/Cap gene with the insulator sequence (bold) is set forth in SEQ ID NO: 16:

CCCTAGAAAGATAATCATATTGTGACGTACGTTAAAGATAATCATGTGTAAAATTGACGCATGT

GTTTTATCGGTCTGTATATCGAGGTTTATTTATTAATTTGAATAGATATTAAGTTTTATTATAT

TTACACTTACATACTAATAATAAATTCAACAAACAATTTATTTATGTTTATTTATTTATTAAAA

AAAACAAAAACTCAAAATTTCTTCTATAAAGTAACAAAACTTTTATGAGGGACAGCCCCCCCCC

AAAGCCCCCAGGGATGTAATTACGTCCCTCCCCCGCTAGGGGGCAGCAGCGAGCCGCCCGGGGC

TCCGCTCCGGTCCGGCGCTCCCCCCGCATCCCCGAGCCGGCAGCGTGCGGGGACAGCCCGGGCA

CGGGGAAGGTGGCACGGGATCGCTTTCCTCTGAACGCTTCTCGCTGCTCTTTGAGCCTGCAGAC

ACCTGGGGGGATACGGGGAAAAGGCTAGAGGTCCTGTATTAGAGGTCACGTGAGTGTTTTGCGA

CATTTTGCGACACCATGTGGTCACGCTGGGTATTTAAGCCCGAGTGAGCACGCAGGGTCTCCAT

TTTGAAGCGAGGATCCATCACACTGGCGGCCGCTCGAGGGGAGCTCGCAGGGTCTCCATTTTGA

AGCGGGAGGTTTGAACGCGCAGCCGCCATGCCGGGGTTTTACGAGATTGTGATTAAGGTCCCCA

GCGACCTTGACGAGCATCTGCCCGGCATTTCTGACAGCTTTGTGAACTGGGTGGCCGAGAAGGA

ATGGGAGTTGCCGCCAGATTCTGACATGGATCTGAATCTGATTGAGCAGGCACCCCTGACCGTG

GCCGAGAAGCTGCAGCGCGACTTTCTGACGGAATGGCGCCGTGTGAGTAAGGCCCCGGAGGCTC

TTTTCTTTGTGCAATTTGAGAAGGGAGAGAGCTACTTCCACATGCACGTGCTCGTGGAAACCAC

CGGGGTGAAATCCATGGTTTTGGGACGTTTCCTGAGTCAGATTCGCGAAAAACTGATTCAGAGA

ATTTACCAGCGGGATCGAGCCGACTTTGCCAAACTGGTTCGCGGTCACAAAGACCAGAAATGGC

GCCGGAGGCGGGAACAAGGTGGTGGATGAGTGCTACATCCCCAATTACTTGCTCCCCAAAACCC

AGCCTGAGCTCCAGTGGGCGTGGACTAATATGGAACAGTATTTAAGCGCCTGTTTGAATCTCAC

GGAGCGTAAACGGTTGGTGGCGCAGCATCTGACGCACGTGTCGCAGACGCAGGAGCAGAACAAA

-continued

GAGAATCAGAATCCCAATTCTGATGCGCCGGTGATCAGATCAAAAACTTCAGCCAGGTACATGG

AGCTGGTCGGGTGGCTCGTGGACAAGGGGATTACCTAGGAGAAGCAGTGGATCCAGGAGGACCA

GGCCTCATACATCTCCTTCAATGCGGCCTCCAACTCGCGGTCCCAAATCAAGGCTGCCTTGGAC

AATGCGGGAAAGATTATGAGCCTGACTAAAACCGCCCCCGACTACCTGGTGGGCCAGCAGCCCG

TGGAGGACATTTCCAGCAATCGGATTTATAAAATTTTGGAACTAAACGGGTACGATCCCCAATA

TGCGGCTTCCGTCTTTCTGGGATGGGCCACGAAAAAGTTCGGCAAGAGGAACACCATCTGGCTG

TTTGGGCCTGCAACTACCGGGAAGACCAACATCGCGGAGGCCATAGCCCACACTGTGCCCTTCT

ACGGGTGCGTAAACTGGACCAATGAGAACTTTCCCTTCAACGACTGTGTCGACAAGATGGTGAT

CTGGTGGGAGGAGGGGAAGATGACCGCCAAGGTCGTGGAGTCGGCCAAAGCCATTCTCGGAGGA

AGCAAGGTGCGCGTGGACCAGAAATGCAAGTCCTCGGCCCAGATAGACCCGACTCCCGTGATCG

TCACCTCCAACACCAACATGTGCGCCGTGATTGACGGGAACTCAACGACCTTCGAACACCAGCA

GCCGTTGCAAGACCGGATGTTCAAATTTGAACTCACCCGCCGTCTGGATCATGACTTTGGGAAG

GTCACCAAGCAGGAAGTCAAAGACTTTTTCCGGTGGGCAAAGGATCACGTGGTTGAGGTGGAGC

ATGAATTCTACGTCAAAAAGGGTGGAGCCAAGAAAAGACCCGCCCCCAGTGACGCAGATATAAG

TGAGCCCAAACGGGTGCGCGAGTCAGTTGCGCAGCCATCGACGTCAGACGCGGAAGCTTCGATC

AACTACGCAGACAGGTACCAAAACAAATGTTCTCGTCACGTGGGCATGAATCTGATGCTGTTTC

CCTGCAGACAATGCGAGAGAATGAATCAGAATTCAAATATCTGCTTCACTCACGGACAGAAAGA

CTGTTTAGAGTGCTTTCCCGTGTCAGAATCTCAACCCGTTTCTGTCGTCAAAAAGGCGTATCAG

AAACTGTGCTACATTCATCATATCATGGGAAAGGTGCCAGACGCTTGCACTGCCTGCGATCTGG

TCAATGTGGATTTGGATGACTGCATCTTTGAACAATAAATGATTTAAATCAGGTATGGCTGCCG

ATGGTTATCTTCCAGATTGGCTCGAGGACACTCTCTCTGAAGGAATAAGACAGTGGTGGAAGCT

CAAACCTGGCCCACCACCACCAAAGCCCGCAGAGCGGCATAAGGACGACAGCAGGGGTCTTGTG

CTTCCTGGGTACAAGTACCTCGGACCCTTCAACGGACTCGACAAGGGAGAGCCGGTCAACGAGG

CAGACGCCGCGGCCCTCGAGCACGACAAAGCCTACGACCGGCAGCTCGACAGCGGAGACAACCC

GTACCTCAAGTACAACCACGCCGACGCGGAGTTTCAGGAGCGCCTTAAAGAAGATACGTCTTTT

GGGGGCAACCTCGGACGAGCAGTCTTCCAGGCGAAAAAGAGGGTTCTTGAACCTCTGGGCCTGG

TTGAGGAACCTGTTAAGACGGCTCCGGGAAAAAAGAGGCCGGTAGAGCACTCTCCTGTGGAGCC

AGACTCCTCCTCGGGAACCGGAAAGGCGGGCCAGCAGCCTGCAAGAAAAAGATTGAATTTTGGT

CAGACTGGAGACGCAGACTCAGTACCTGACCCCCAGCCTCTCGGACAGCCACCAGCAGCCCCCT

CTGGTCTGGGAACTAATACGATGGCTACAGGCAGTGGCGCACCAATGGCAGACAATAACGAGGG

CGCCGACGGAGTGGGTAATTCCTCGGGAAATTGGCATTGCGATTCCACATGGATGGGCGACAGA

GTCATCACCACCAGCACCCGAACCTGGGCCCTGCCCACCTACAACAACCACCTCTACAAACAAA

TTTCCAGCCAATCAGGAGCCTCGAACGACAATCACTACTTTGGCTACAGCACCCCTTGGGGGTA

TTTTGACTTCAACAGATTCCACTGCCACTTTTCACCACGTGACTGGCAAAGACTCATCAACAAC

AACTGGGGATTCCGACCCAAGAGACTCAACTTCAAGCTCTTTAACATTCAAGTCAAAGAGGTCA

CGCAGAATGACGGTACGACGACGATTGCCAATAACCTTACCAGCACGGTTCAGGTGTTTACTGA

CTCGGAGTACCAGCTCCCGTACGTCCTCGGCTCGGCGCATCAAGGATGCCTCCCGCCGTTCCCA

GCAGACGTCTTCATGGTGCCACAGTATGGATACCTCACCCTGAACAACGGGAGTCAGGCAGTAG

GACGCTCTTCATTTTACTGCCTGGAGTACTTTCCTTCTCAGATGCTGCGTACCGGAAACAACTT

TACCTTCAGCTACACTTTTGAGGACGTTCCTTTCCACAGCAGCTACGCTCACAGCCAGAGTCTG

GACCGTCTCATGAATCCTCTCATCGACCAGTACCTGTATTACTTGAGCAGAACAAACACTCCAA

-continued

GTGGAACCACCACGCAGTCAAGGCTTCAGTTTTCTCAGGCCGGAGCGAGTGACATTCGGGACCA

GTCTAGGAACTGGCTTCCTGGACCCTGTTACCGCCAGCAGCGAGTATCAAAGACATCTGCGGAT

AACAACAACAGTGAATACTCGTGGACTGGAGCTACCAAGTACCACCTCAATGGCAGAGACTCTC

TGGTGAATCCGGGCCCGGCCATGGCAAGCCACAAGGACGATGAAGAAAAGTTTTTTCCTCAGAG

CGGGGTTCTCATCTTTGGGAAGCAAGGCTCAGAGAAAACAAATGTGGACATTGAAAAGGTCATG

ATTACAGACGAAGAGGAAATCAGGACAACCAATCCCGTGGCTACGGAGCAGTATGGTTCTGTAT

CTACCAACCTCCAGAGAGGCAACAGACAAGCAGCTACCGCAGATGTCAACACACAAGGCGTTCT

TCCAGGCATGGTCTGGCAGGACAGAGATGTGTACCTTCAGGGGCCCATCTGGGCAAAGATTCCA

CACACGGACGGACATTTTCACCCCTCTCCCCTCATGGGTGGATTCGGACTTAAACACCCTCCTC

CACAGATTCTCATCAAGAACACCCCGGTACCTGCGAATCCTTCGACCACCTTCAGTGCGGCAAA

GTTTGCTTCCTTCATCACACAGTACTCCACGGGACAGGTCAGCGTGGAGATCGAGTGGGAGCTG

CAGAAGGAAAACAGCAAACGCTGGAATCCCGAAATTCAGTACACTTCCAACTACAACAAGTCTG

TTAATGTGGACTTTACTGTGGACACTAATGGCGTGTATTCAGAGCCTCGCCCCATTGGCACCAG

ATACCTGACTCGTAATCTGTAATTGCTTGTTAATCAATAAACCGTTTAATTCGTTTCAGTTGAA

CTTTGGTCTCTGCGTATTTCTTTCTTATCTAGTTTCCATGCTCCTCCACGGCCAAGGATCTGCG

ATCGCTCCGGTGCCCGTCAGTGGGCAGAGCGCACATCGCCCACAGTCCCCGAGAAGTTGGGGGG

AGGGGTCGGCAATTGAACGGGTGCCTAGAGAAGGTGGCGCGGGGTAAACTGGGAAAGTGATGTC

GTGTACTGGCTCCGCCTTTTTCCCGAGGGTGGGGGAGAACCGTATATAAGTGCAGTAGTCGCCG

TGAACGTTCTTTTTCGCAACGGGTTTGCCGCCAGAACACAGCTGAAGCTTCGAGGGGCTCGCAT

CTCTCCTTCACGCGCCCGCCGCCCTACCTGAGGCCGCCATCCACGCCGGTTGAGTCGCGTTCTG

CCGCCTCCCGCCTGTGGTGCCTCCTGAACTGCGTCCGCCGTCTAGGTAAGTTTAAAGCTCAGGT

CGAGACCGGGCCTTTGTCCGGCGCTCCCTTGGAGCCTACCTAGACTCAGCCGGCTCTCCACGCT

TTGCCTGACCCTGCTTGCTCAACTCTACGTCTTTGTTTCGTTTTCTGTTCTGCGCCGTTACAGA

TCCAAGCTGTGACCGGCGCCTACTCTAGAGCTAGCGAATTCGAATTTAAATCGGATCCGCGGCC

GCGCCCCTCTCCCTCCCCCCCCCCTAACGTTACTGGCCGAAGCCGCTTGGAATAAGGCCGGTGT

GCGTTTGTCTATATGTTATTTTCCACCATATTGCCGTCTTTTGGCAATGTGAGGGCCCGGAAAC

CTGGCCCTGTCTTCTTGACGAGCATTCCTAGGGGTCTTTCCCCTCTCGCCAAAGGAATGCAAGG

TCTGTTGAATGTCGTGAAGGAAGCAGTTCCTCTGGAAGCTTCTTGAAGACAAACAACGTCTGTA

GCGACCCTTTGCAGGCAGCGGAACCCCCCACCTGGCGACAGGTGCCTCTGCGGCCAAAAGCCAC

GTGTATAAGATACACCTGCAAAGGCGGCACAACCCCAGTGCCACGTTGTGAGTTGGATAGTTGT

GGAAAGAGTCAAATGGCTCTCCTCAAGCGTATTCAACAAGGGGCTGAAGGATGCCCAGAAGGTA

CCCCATTGTATGGGATCTGATCTGGGGCCTCGGTGCACATGCTTTACATGTGTTTAGTCGAGGT

TAAAAAAACGTCTAGGCCCCCCGAACCACGGGGACGTGGTTTTCCTTTGAAAAACACGATGATA

ATATGGCCACAACCATGGCGTCCGGAATGATTGAACAAGATGGATTGCACGCAGGTTCTCCGGC

CGCTTGGGTGGAGAGGCTATTCGGCTATGACTGGGCACAACAGACAATCGGCTGCTCTGATGCC

GCCGTGTTCCGGCTGTCAGCGCAGGGGCGCCCGGTTCTTTTTGTCAAGACCGACCTGTCCGGTG

CCCTGAATGAACTGCAGGACGAGGCAGCGCGGCTATCGTGGCTGGCCGCGACGGGCGTTCCTTG

CGCAGCTGTGCTCGACGTTGTCACTGAAGCGGGAAGGGACTGGCTGCTATTGGGCGAAGTGCCG

GGGCAGGATCTCCTGTCATCTCACCTTGCTCCTGCCGAGAAAGTATCCATCATGGCTGATGCAA

TGCGGCGGCTGCATACGCTTGATCCGGCTACCTGCCCATTCGACCACCAAGCGAAACATCGCAT

-continued

CGAGCGAGCACGTACTCGGATGGAAGCCGGTCTTGTCGATCAGGATGATCTGGACGAAGAGCAT

CAGGGGCTCGCGCCAGCCGAACTGTTCGCCAGGCTCAAGGCGCGCATGCCCGACGGCGAGGATC

TCGTCGTGACCCATGGCGATGCCTGCTTGCCGAATATCATGGTGGAAAATGGCCGCTTTTCTGG

ATTCATCGACTGTGGCCGGCTGGGTGTGGCGGACCGCTATCAGGACATAGCGTTGGCTACCCGT

GATATTGCTGAAGAGCTTGGCGGCGAATGGGCTGACCGCTTCCTCGTGCTTTACGGTATCGCCG

CTCCCGATTCGCAGCGCATCGCCTTCTATCGCCTTCTTGACGAGTTCTTCTGAGTCGACAATCA

ACCTCTGGATTACAAAATTTGTGAAAGATTGACTGGTATTCTTAACTATGTTGCTCCTTTTACG

CTATGTGGATACGCTGCTTTAATGCCTTTGTATCATGCGTTAACTAAACTTGTTTATTGCAGCT

TATAATGGTTACAAATAAAGCAATAGCATCACAAATTTCACAAATAAAGCATTTTTTTCACTGC

ATTCTAGTTGTGGTTTGTCCAAACTCATCAATGTATCTTATCATGTCTGGAATTGACTCAAATG

ATGTCAATTAGTCTATCAGAAGCTCATCTGGTCTCCCTTCCGGGGGACAAGACATCCCTGTTTA

ATATTTAAACAGCAGTGTTCCCAAACTGGGTTCTTATATCCCTTGCTCTGGTCAACCAGGTTGC

AGGGTTTCCTGTCCTCACAGGAACGAAGTCCCTAAAGAAACAGTGGCAGCCAGGTTTAGCCCCG

GAATTGACTGGATTCCTTTTTTAGGGCCCATTGGTATGGCTTTTTCCCCGTATCCCCCCAGGTG

TCTGCAGGCTCAAAGAGCAGCGAGAAGCGTTCAGAGGAAAGCGATCCCGTGCCACCTTCCCCGT

GCCCGGGCTGTCCCCGCACGCTGCCGGCTCGGGGATGCGGGGGGAGCGCCGGACCGGAGCGGAG

CCCCGGGCGGCTCGCTGCTGCCCCCTAGCGGGGGAGGGACGTAATTACATCCCTGGGGGCTTTG

GGGGGGGGCTGTCCCTGATATCTATAACAAGAAAATATATATATAATAAGTTATCACGTAAGTA

GAACATGAAATAACAATATAATTATCGTATGAGTTAAATCTTAAAAGTCACGTAAAAGATAATC

ATGCGTCATTTTGACTCACGCGGTCGTTATAGTTCAAAATCAGTGACACTTACCGCATTGACAA

GCACGCCTCACGGGAGCTCCAAGCGGCGACTGAGATGTCCTAAATGCACAGCGACGGATTCGCG

CTATTTAGAAAGAGAGAGCAATATTTCAAGAATGCATGCGTCAATTTTACGCAGACTATCTTTC

TAGGG

An exemplary nucleic acid sequence encoding a mutant rep (C714A, bold and underlined)/Cap gene with the stuffer sequence (underlined) is set forth in SEQ ID NO: 17:

CCCTAGAAAGATAATCATATTGTGACGTACGTTAAAGATAATCATGTGTAAAATTGACGCATGT

GTTTTATCGGTCTGTATATCGAGGTTTATTTATTAATTTGAATAGATATTAAGTTTTATTATAT

TTACACTTACATACTAATAATAAATTCAACAAACAATTTATTTATGTTTATTTATTTATTAAAA

AAAACAAAAACTCAAAATTTCTTCTATAAAGTAACAAATCCTGTATTAGAGGTCACGTGAGTGT

TTTGCGACATTTTGCGACACCATGTGGTCACGCTGGGTATTTAAGCCCGAGTGAGCACGCAGGG

TCTCCATTTTGAAGCGGGAGGTTTGAACGCGCAGCCGCCAAGCCGAATTCTGCAGATATCCCCG

AGTCCTTCAATGCTATCATTCCCTTTGATATTGGACCATATGCATAGTACCGAGAAACTAGTGC

GAAGTAGTGATCAGGTATTGCTGTTAGATATCCCCGAGTCCTTCAATGCTATCATTCTCTTTGA

TATTGGACCATATGCATAGTACCGAGAAACTAGTGCGAAGTAGTGATCAGGTATTGCTGTTAGA

TATCCCCGAGTCCTTCAATGCTATCATTCCCTTTGATATTGGACCATATGCATAGTACCGAGAA

ACTAGTGCGAAGTAGTGATCAGGTATTGCTGTTAGATATCCCCGAGTCCTTCAATGCTATCATT

CTCTTTGATATTGGACCATATGCATAGTACCGAGAAACTAGTGCGAAGTAGTGATCAGGTATTG

CTGTTAGATATCCCCGAGTCCTTCAATGCTATCATTCCCTTTGATATTGGACCATATGCATAGT

ACCGAGAAACTAGTGCGAAGTAGTGATCAGGTATTGCTGTTAGATATCCCCGAGTCCTTCAATG

-continued

CTATCATTTCCTTTGATATTGGATCATATGCATAGTACCGAGAAACTAGTGCGAAGTAGTGATC

AGGTATTGCTGTTAAGGATCCATCACACTGGCGGCCGCTCGAGGGGAGCTCGCAGGGTCTCCAT

TTTGAAGCGGGAGGTTTGAACGCGCAGCCGCCATGCCGGGGTTTTACGAGATTGTGATTAAGGT

CCCCAGCGACCTTGACGAGCATCTGCCCGGCATTTCTGACAGCTTTGTGAACTGGGTGGCCGAG

AAGGAATGGGAGTTGCCGCCAGATTCTGACATGGATCTGAATCTGATTGAGCAGGCACCCCTGA

CCGTGGCCGAGAAGCTGCAGCGCGACTTTCTGACGGAATGGCGCCGTGTGAGTAAGGCCCCGGA

GGCTCTTTTCTTTGTGCAATTTGAGAAGGGAGAGAGCTACTTCCACATGCACGTGCTCGTGGAA

ACCACCGGGGTGAAATCCATGGTTTTGGGACGTTTCCTGAGTCAGATTCGCGAAAAACTGATTC

AGAGAATTTACCAGCGGGATCGAGCCGACTTTGCCAAACTGGTTCGCGGTCACAAAGACCAGAA

ATGGCGCCGGAGGCGGGAACAAGGTGGTGGATGAGTGCTACATCCCCAATTACTTGCTCCCCAA

AACCCAGCCTGAGCTCCAGTGGGCGTGGACTAATATGGAACAGTATTTAAGCGCCTGTTTGAAT

CTCACGGAGCGTAAACGGTTGGTGGCGCAGCATCTGACGCACGTGTCGCAGACGCAGGAGCAGA

ACAAAGAGAATCAGAATCCCAATTCTGATGCGCCGGTGATCAGATCAAAAACTTCAGCCAGGTA

CATGGAGCTGGTCGGGTGGCTCGTGGACAAGGGGATTACCTAGGAGAAGCAGTGGATCCAGGAG

GACCAGGCCTCATACATCTCCTTCAATGCGGCCTCCAACTCGCGGTCCCAAATCAAGGCTGCCT

TGGACAATGCGGGAAAGATTATGAGCCTGACTAAAACCGCCCCCGACTACCTGGTGGGCCAGCA

GCCCGTGGAGGACATTTCCAGCAATCGGATTTATAAAATTTTGGAACTAAACGGGTACGATCCC

CAATATGCGGCTTCCGTCTTTCTGGGATGGGCCACGAAAAAGTTCGGCAAGAGGAACACCATCT

GGCTGTTTGGGCCTGCAACTACCGGGAAGACCAACATCGCGGAGGCCATAGCCCACACTGTGCC

CTTCTACGGGTGCGTAAACTGGACCAATGAGAACTTTCCCTTCAACGACTGTGTCGACAAGATG

GTGATCTGGTGGGAGGAGGGGAAGATGACCGCCAAGGTCGTGGAGTCGGCCAAAGCCATTCTCG

GAGGAAGCAAGGTGCGCGTGGACCAGAAATGCAAGTCCTCGGCCCAGATAGACCCGACTCCCGT

GATCGTCACCTCCAACACCAACATGTGCGCCGTGATTGACGGGAACTCAACGACCTTCGAACAC

CAGCAGCCGTTGCAAGACCGGATGTTCAAATTTGAACTCACCCGCCGTCTGGATCATGACTTTG

GGAAGGTCACCAAGCAGGAAGTCAAAGACTTTTTCCGGTGGGCAAAGGATCACGTGGTTGAGGT

GGAGCATGAATTCTACGTCAAAAAGGGTGGAGCCAAGAAAAGACCCGCCCCCAGTGACGCAGAT

ATAAGTGAGCCCAAACGGGTGCGCGAGTCAGTTGCGCAGCCATCGACGTCAGACGCGGAAGCTT

CGATCAACTACGCAGACAGGTACCAAAACAAATGTTCTCGTCACGTGGGCATGAATCTGATGCT

GTTTCCCTGCAGACAATGCGAGAGAATGAATCAGAATTCAAATATCTGCTTCACTCACGGACAG

AAAGACTGTTTAGAGTGCTTTCCCGTGTCAGAATCTCAACCCGTTTCTGTCGTCAAAAAGGCGT

ATCAGAAACTGTGCTACATTCATCATATCATGGGAAAGGTGCCAGACGCTTGCACTGCCTGCGA

TCTGGTCAATGTGGATTTGGATGACTGCATCTTTGAACAATAAATGATTTAAATCAGGTATGGC

TGCCGATGGTTATCTTCCAGATTGGCTCGAGGACACTCTCTCTGAAGGAATAAGACAGTGGTGG

AAGCTCAAACCTGGCCCACCACCACCAAAGCCCGCAGAGCGGCATAAGGACGACAGCAGGGGTC

TTGTGCTTCCTGGGTACAAGTACCTCGGACCCTTCAACGGACTCGACAAGGGAGAGCCGGTCAA

CGAGGCAGACGCCGCGGCCCTCGAGCACGACAAAGCCTACGACCGGCAGCTCGACAGCGGAGAC

AACCCGTACCTCAAGTACAACCACGCCGACGCGGAGTTTCAGGAGCGCCTTAAAGAAGATACGT

CTTTTGGGGGCAACCTCGGACGAGCAGTCTTCCAGGCGAAAAAGAGGGTTCTTGAACCTCTGGG

CCTGGTTGAGGAACCTGTTAAGACGGCTCCGGGAAAAAAGAGGCCGGTAGAGCACTCTCCTGTG

GAGCCAGACTCCTCCTCGGGAACCGGAAAGGCGGGCCAGCAGCCTGCAAGAAAAAGATTGAATT

TTGGTCAGACTGGAGACGCAGACTCAGTACCTGACCCCCAGCCTCTCGGACAGCCACCAGCAGC

-continued

CCCCTCTGGTCTGGGAACTAATACGATGGCTACAGGCAGTGGCGCACCAATGGCAGACAATAAC

GAGGGCGCCGACGGAGTGGGTAATTCCTCGGGAAATTGGCATTGCGATTCCACATGGATGGGCG

ACAGAGTCATCACCACCAGCACCCGAACCTGGGCCCTGCCCACCTACAACAACCACCTCTACAA

ACAAATTTCCAGCCAATCAGGAGCCTCGAACGACAATCACTACTTTGGCTACAGCACCCCTTGG

GGGTATTTTGACTTCAACAGATTCCACTGCCACTTTTCACCACGTGACTGGCAAAGACTCATCA

ACAACAACTGGGGATTCCGACCCAAGAGACTCAACTTCAAGCTCTTTAACATTCAAGTCAAAGA

GGTCACGCAGAATGACGGTACGACGACGATTGCCAATAACCTTACCAGCACGGTTCAGGTGTTT

ACTGACTCGGAGTACCAGCTCCCGTACGTCCTCGGCTCGGCGCATCAAGGATGCCTCCCGCCGT

TCCCAGCAGACGTCTTCATGGTGCCACAGTATGGATACCTCACCCTGAACAACGGGAGTCAGGC

AGTAGGACGCTCTTCATTTTACTGCCTGGAGTACTTTCCTTCTCAGATGCTGCGTACCGGAAAC

AACTTTACCTTCAGCTACACTTTTGAGGACGTTCCTTTCCACAGCAGCTACGCTCACAGCCAGA

GTCTGGACCGTCTCATGAATCCTCTCATCGACCAGTACCTGTATTACTTGAGCAGAACAAACAC

TCCAAGTGGAACCACCACGCAGTCAAGGCTTCAGTTTTCTCAGGCCGGAGCGAGTGACATTCGG

GACCAGTCTAGGAACTGGCTTCCTGGACCCTGTTACCGCCAGCAGCGAGTATCAAAGACATCTG

CGGATAACAACAACAGTGAATACTCGTGGACTGGAGCTACCAAGTACCACCTCAATGGCAGAGA

CTCTCTGGTGAATCCGGGCCCGGCCATGGCAAGCCACAAGGACGATGAAGAAAAGTTTTTTCCT

CAGAGCGGGGTTCTCATCTTTGGGAAGCAAGGCTCAGAGAAAACAAATGTGGACATTGAAAAGG

TCATGATTACAGACGAAGAGGAAATCAGGACAACCAATCCCGTGGCTACGGAGCAGTATGGTTC

TGTATCTACCAACCTCCAGAGAGGCAACAGACAAGCAGCTACCGCAGATGTCAACACACAAGGC

GTTCTTCCAGGCATGGTCTGGCAGGACAGAGATGTGTACCTTCAGGGGCCCATCTGGGCAAAGA

TTCCACACACGGACGGACATTTTCACCCCTCTCCCCTCATGGGTGGATTCGGACTTAAACACCC

TCCTCCACAGATTCTCATCAAGAACACCCCGGTACCTGCGAATCCTTCGACCACCTTCAGTGCG

GCAAAGTTTGCTTCCTTCATCACACAGTACTCCACGGGACAGGTCAGCGTGGAGATCGAGTGGG

AGCTGCAGAAGGAAAACAGCAAACGCTGGAATCCCGAAATTCAGTACACTTCCAACTACAACAA

GTCTGTTAATGTGGACTTTACTGTGGACACTAATGGCGTGTATTCAGAGCCTCGCCCCATTGGC

ACCAGATACCTGACTCGTAATCTGTAATTGCTTGTTAATCAATAAACCGTTTAATTCGTTTCAG

TTGAACTTTGGTCTCTGCGTATTTCTTTCTTATCTAGTTTCCATGCTCCTCCACGGCCAAGGAT

CTGCGATCGCTCCGGTGCCCGTCAGTGGGCAGAGCGCACATCGCCCACAGTCCCCGAGAAGTTG

GGGGGAGGGGTCGGCAATTGAACGGGTGCCTAGAGAAGGTGGCGCGGGGTAAACTGGGAAAGTG

ATGTCGTGTACTGGCTCCGCCTTTTTCCCGAGGGTGGGGGAGAACCGTATATAAGTGCAGTAGT

CGCCGTGAACGTTCTTTTTCGCAACGGGTTTGCCGCCAGAACACAGCTGAAGCTTCGAGGGGCT

CGCATCTCTCCTTCACGCGCCCGCCGCCCTACCTGAGGCCGCCATCCACGCCGGTTGAGTCGCG

TTCTGCCGCCTCCCGCCTGTGGTGCCTCCTGAACTGCGTCCGCCGTCTAGGTAAGTTTAAAGCT

CAGGTCGAGACCGGGCCTTTGTCCGGCGCTCCCTTGGAGCCTACCTAGACTCAGCCGGCTCTCC

ACGCTTTGCCTGACCCTGCTTGCTCAACTCTACGTCTTTGTTTCGTTTTCTGTTCTGCGCCGTT

ACAGATCCAAGCTGTGACCGGCGCCTACTCTAGAGCTAGCGAATTCGAATTTAAATCGGATCCG

CGGCCGCGCCCCTCTCCCTCCCCCCCCCCTAACGTTACTGGCCGAAGCCGCTTGGAATAAGGCC

GGTGTGCGTTTGTCTATATGTTATTTTCCACCATATTGCCGTCTTTTGGCAATGTGAGGGCCCG

GAAACCTGGCCCTGTCTTCTTGACGAGCATTCCTAGGGGTCTTTCCCCTCTCGCCAAAGGAATG

CAAGGTCTGTTGAATGTCGTGAAGGAAGCAGTTCCTCTGGAAGCTTCTTGAAGACAAACAACGT

-continued

```
CTGTAGCGACCCTTTGCAGGCAGCGGAACCCCCCACCTGGCGACAGGTGCCTCTGCGGCCAAAA

GCCACGTGTATAAGATACACCTGCAAAGGCGGCACAACCCCAGTGCCACGTTGTGAGTTGGATA

GTTGTGGAAAGAGTCAAATGGCTCTCCTCAAGCGTATTCAACAAGGGGCTGAAGGATGCCCAGA

AGGTACCCCATTGTATGGGATCTGATCTGGGGCCTCGGTGCACATGCTTTACATGTGTTTAGTC

GAGGTTAAAAAAACGTCTAGGCCCCCCGAACCACGGGGACGTGGTTTTCCTTTGAAAAACACGA

TGATAATATGGCCACAACCATGGCGTCCGGAATGATTGAACAAGATGGATTGCACGCAGGTTCT

CCGGCCGCTTGGGTGGAGAGGCTATTCGGCTATGACTGGGCACAACAGACAATCGGCTGCTCTG

ATGCCGCCGTGTTCCGGCTGTCAGCGCAGGGGCGCCCGGTTCTTTTTGTCAAGACCGACCTGTC

CGGTGCCCTGAATGAACTGCAGGACGAGGCAGCGCGGCTATCGTGGCTGGCCGCGACGGGCGTT

CCTTGCGCAGCTGTGCTCGACGTTGTCACTGAAGCGGGAAGGGACTGGCTGCTATTGGGCGAAG

TGCCGGGGCAGGATCTCCTGTCATCTCACCTTGCTCCTGCCGAGAAAGTATCCATCATGGCTGA

TGCAATGCGGCGGCTGCATACGCTTGATCCGGCTACCTGCCCATTCGACCACCAAGCGAAACAT

CGCATCGAGCGAGCACGTACTCGGATGGAAGCCGGTCTTGTCGATCAGGATGATCTGGACGAAG

AGCATCAGGGGCTCGCGCCAGCCGAACTGTTCGCCAGGCTCAAGGCGCGCATGCCCGACGGCGA

GGATCTCGTCGTGACCCATGGCGATGCCTGCTTGCCGAATATCATGGTGGAAAATGGCCGCTTT

TCTGGATTCATCGACTGTGGCCGGCTGGGTGTGGCGGACCGCTATCAGGACATAGCGTTGGCTA

CCCGTGATATTGCTGAAGAGCTTGGCGGCGAATGGGCTGACCGCTTCCTCGTGCTTTACGGTAT

CGCCGCTCCCGATTCGCAGCGCATCGCCTTCTATCGCCTTCTTGACGAGTTCTTCTGAGTCGAC

AATCAACCTCTGGATTACAAAATTTGTGAAAGATTGACTGGTATTCTTAACTATGTTGCTCCTT

TTACGCTATGTGGATACGCTGCTTTAATGCCTTTGTATCATGCGTTAACTAAACTTGTTTATTG

CAGCTTATAATGGTTACAAATAAAGCAATAGCATCACAAATTTCACAAATAAAGCATTTTTTTC

ACTGCATTCTAGTTGTGGTTTGTCCAAACTCATCAATGTATCTTATCATGTCTGGAATTGACTC

AAATGATGTCAATTAGTCTATCAGAAGCTCATCTGGTCTCCCTTCCGGGGGACAAGACATCCCT

GTTTAATATTTAAACAGCAGTGTTCCCAAACTGGGTTCTTATATCCCTTGCTCTGGTCAACCAG

GTTGCAGGGTTTCCTGTCCTCACAGGAACGAAGTCCCTAAAGAAACAGTGGCAGCCAGGTTTAG

CCCCGGAATTGACTGGATTCCTTTTTTAGGGCCCATTGGTATTATAACAAGAAAATATATATAT

AATAAGTTATCACGTAAGTAGAACATGAAATAACAATATAATTATCGTATGAGTTAAATCTTAA

AAGTCACGTAAAAGATAATCATGCGTCATTTTGACTCACGCGGTCGTTATAGTTCAAAATCAGT

GACACTTACCGCATTGACAAGCACGCCTCACGGGAGCTCCAAGCGGCGACTGAGATGTCCTAAA

TGCACAGCGACGGATTCGCGCTATTTAGAAAGAGAGAGCAATATTTCAAGAATGCATGCGTCAA

TTTTACGCAGACTATCTTTCTAGGG
```

An exemplary nucleic acid sequence encoding a mutant rep (C714A, bold and underlined)/Cap gene is set forth in SEQ ID NO: 18:

```
CCCTAGAAAGATAATCATATTGTGACGTACGTTAAAGATAATCATGTGTAAAATTGACGCATGT

GTTTTATCGGTCTGTATATCGAGGTTTATTTATTAATTTGAATAGATATTAAGTTTTATTATAT

TTACACTTACATACTAATAATAAATTCAACAAACAATTTATTTATGTTTATTTATTTATTAAAA

AAAACAAAAACTCAAAATTTCTTCTATAAAGTAACAAATCCTGTATTAGAGGTCACGTGAGTGT

TTTGCGACATTTTGCGACACCATGTGGTCACGCTGGGTATTTAAGCCCGAGTGAGCACGCAGGG

TCTCCATTTTGAAGCGAGGATCCATCACACTGGCGGCCGCTCGAGGGGAGCTCGCAGGGTCTCC
```

-continued

ATTTTGAAGCGGGAGGTTTGAACGCGCAGCCGCCATGCCGGGGTTTTACGAGATTGTGATTAAG

GTCCCCAGCGACCTTGACGAGCATCTGCCCGGCATTTCTGACAGCTTTGTGAACTGGGTGGCCG

AGAAGGAATGGGAGTTGCCGCCAGATTCTGACATGGATCTGAATCTGATTGAGCAGGCACCCCT

GACCGTGGCCGAGAAGCTGCAGCGCGACTTTCTGACGGAATGGCGCCGTGTGAGTAAGGCCCCG

GAGGCTCTTTTCTTTGTGCAATTTGAGAAGGGAGAGAGCTACTTCCACATGCACGTGCTCGTGG

AAACCACCGGGGTGAAATCCATGGTTTTGGGACGTTTCCTGAGTCAGATTCGCGAAAAACTGAT

TCAGAGAATTTACCAGCGGGATCGAGCCGACTTTGCCAAACTGGTTCGCGGTCACAAAGACCAG

AAATGGCGCCGGAGGCGGGAACAAGGTGGTGGATGAGTGCTACATCCCCAATTACTTGCTCCCC

AAAACCCAGCCTGAGCTCCAGTGGGCGTGGACTAATATGGAACAGTATTTAAGCGCCTGTTTGA

ATCTCACGGAGCGTAAACGGTTGGTGGCGCAGCATCTGACGCACGTGTCGCAGACGCAGGAGCA

GAACAAAGAGAATCAGAATCCCAATTCTGATGCGCCGGTGATCAGATCAAAAACTTCAGCCAGG

TACATGGAGCTGGTCGGGTGGCTCGTGGACAAGGGGATTACCTAGGAGAAGCAGTGGATCCAGG

AGGACCAGGCCTCATACATCTCCTTCAATGCGGCCTCCAACTCGCGGTCCCAAATCAAGGCTGC

CTTGGACAATGCGGGAAAGATTATGAGCCTGACTAAAACCGCCCCCGACTACCTGGTGGGCCAG

CAGCCCGTGGAGGACATTTCCAGCAATCGGATTTATAAAATTTTGGAACTAAACGGGTACGATC

CCCAATATGCGGCTTCCGTCTTTCTGGGATGGGCCACGAAAAAGTTCGGCAAGAGGAACACCAT

CTGGCTGTTTGGGCCTGCAACTACCGGGAAGACCAACATCGCGGAGGCCATAGCCCACACTGTG

CCCTTCTACGGGTGCGTAAACTGGACCAATGAGAACTTTCCCTTCAACGACTGTGTCGACAAGA

TGGTGATCTGGTGGGAGGAGGGGAAGATGACCGCCAAGGTCGTGGAGTCGGCCAAAGCCATTCT

CGGAGGAAGCAAGGTGCGCGTGGACCAGAAATGCAAGTCCTCGGCCCAGATAGACCCGACTCCC

GTGATCGTCACCTCCAACACCAACATGTGCGCCGTGATTGACGGGAACTCAACGACCTTCGAAC

ACCAGCAGCCGTTGCAAGACCGGATGTTCAAATTTGAACTCACCCGCCGTCTGGATCATGACTT

TGGGAAGGTCACCAAGCAGGAAGTCAAAGACTTTTTCCGGTGGGCAAAGGATCACGTGGTTGAG

GTGGAGCATGAATTCTACGTCAAAAAGGGTGGAGCCAAGAAAAGACCCGCCCCCAGTGACGCAG

ATATAAGTGAGCCCAAACGGGTGCGCGAGTCAGTTGCGCAGCCATCGACGTCAGACGCGGAAGC

TTCGATCAACTACGCAGACAGGTACCAAAACAAATGTTCTCGTCACGTGGGCATGAATCTGATG

CTGTTTCCCTGCAGACAATGCGAGAGAATGAATCAGAATTCAAATATCTGCTTCACTCACGGAC

AGAAAGACTGTTTAGAGTGCTTTCCCGTGTCAGAATCTCAACCCGTTTCTGTCGTCAAAAAGGC

GTATCAGAAACTGTGCTACATTCATCATATCATGGGAAAGGTGCCAGACGCTTGCACTGCCTGC

GATCTGGTCAATGTGGATTTGGATGACTGCATCTTTGAACAATAAATGATTTAAATCAGGTATG

GCTGCCGATGGTTATCTTCCAGATTGGCTCGAGGACACTCTCTCTGAAGGAATAAGACAGTGGT

GGAAGCTCAAACCTGGCCCACCACCACCAAAGCCCGCAGAGCGGCATAAGGACGACAGCAGGGG

TCTTGTGCTTCCTGGGTACAAGTACCTCGGACCCTTCAACGGACTCGACAAGGGAGAGCCGGTC

AACGAGGCAGACGCCGCGGCCCTCGAGCACGACAAAGCCTACGACCGGCAGCTCGACAGCGGAG

ACAACCCGTACCTCAAGTACAACCACGCCGACGCGGAGTTTCAGGAGCGCCTTAAAGAAGATAC

GTCTTTTGGGGGCAACCTCGGACGAGCAGTCTTCCAGGCGAAAAAGAGGGTTCTTGAACCTCTG

GGCCTGGTTGAGGAACCTGTTAAGACGGCTCCGGGAAAAAAGAGGCCGGTAGAGCACTCTCCTG

TGGAGCCAGACTCCTCCTCGGGAACCGGAAAGGCGGGCCAGCAGCCTGCAAGAAAAAGATTGAA

TTTTGGTCAGACTGGAGACGCAGACTCAGTACCTGACCCCCAGCCTCTCGGACAGCCACCAGCA

GCCCCCTCTGGTCTGGGAACTAATACGATGGCTACAGGCAGTGGCGCACCAATGGCAGACAATA

ACGAGGGCGCCGACGGAGTGGGTAATTCCTCGGGAAATTGGCATTGCGATTCCACATGGATGGG

-continued

CGACAGAGTCATCACCACCAGCACCCGAACCTGGGCCCTGCCCACCTACAACAACCACCTCTAC

AAACAAATTTCCAGCCAATCAGGAGCCTCGAACGACAATCACTACTTTGGCTACAGCACCCCTT

GGGGGTATTTTGACTTCAACAGATTCCACTGCCACTTTTCACCACGTGACTGGCAAAGACTCAT

CAACAACAACTGGGGATTCCGACCCAAGAGACTCAACTTCAAGCTCTTTAACATTCAAGTCAAA

GAGGTCACGCAGAATGACGGTACGACGACGATTGCCAATAACCTTACCAGCACGGTTCAGGTGT

TTACTGACTCGGAGTACCAGCTCCCGTACGTCCTCGGCTCGGCGCATCAAGGATGCCTCCCGCC

GTTCCCAGCAGACGTCTTCATGGTGCCACAGTATGGATACCTCACCCTGAACAACGGGAGTCAG

GCAGTAGGACGCTCTTCATTTTACTGCCTGGAGTACTTTCCTTCTCAGATGCTGCGTACCGGAA

ACAACTTTACCTTCAGCTACACTTTTGAGGACGTTCCTTTCCACAGCAGCTACGCTCACAGCCA

GAGTCTGGACCGTCTCATGAATCCTCTCATCGACCAGTACCTGTATTACTTGAGCAGAACAAAC

ACTCCAAGTGGAACCACCACGCAGTCAAGGCTTCAGTTTTCTCAGGCCGGAGCGAGTGACATTC

GGGACCAGTCTAGGAACTGGCTTCCTGGACCCTGTTACCGCCAGCAGCGAGTATCAAAGACATC

TGCGGATAACAACAACAGTGAATACTCGTGGACTGGAGCTACCAAGTACCACCTCAATGGCAGA

GACTCTCTGGTGAATCCGGGCCCGGCCATGGCAAGCCACAAGGACGATGAAGAAAAGTTTTTTC

CTCAGAGCGGGGTTCTCATCTTTGGGAAGCAAGGCTCAGAGAAAACAAATGTGGACATTGAAAA

GGTCATGATTACAGACGAAGAGGAAATCAGGACAACCAATCCCGTGGCTACGGAGCAGTATGGT

TCTGTATCTACCAACCTCCAGAGAGGCAACAGACAAGCAGCTACCGCAGATGTCAACACACAAG

GCGTTCTTCCAGGCATGGTCTGGCAGGACAGAGATGTGTACCTTCAGGGGCCCATCTGGGCAAA

GATTCCACACACGGACGGACATTTTCACCCCTCTCCCCTCATGGGTGGATTCGGACTTAAACAC

CCTCCTCCACAGATTCTCATCAAGAACACCCCGGTACCTGCGAATCCTTCGACCACCTTCAGTG

CGGCAAAGTTTGCTTCCTTCATCACACAGTACTCCACGGGACAGGTCAGCGTGGAGATCGAGTG

GGAGCTGCAGAAGGAAAACAGCAAACGCTGGAATCCCGAAATTCAGTACACTTCCAACTACAAC

AAGTCTGTTAATGTGGACTTTACTGTGGACACTAATGGCGTGTATTCAGAGCCTCGCCCCATTG

GCACCAGATACCTGACTCGTAATCTGTAATTGCTTGTTAATCAATAAACCGTTTAATTCGTTTC

AGTTGAACTTTGGTCTCTGCGTATTTCTTTCTTATCTAGTTTCCATGCTCCTCCACGGCCAAGG

ATCTGCGATCGCTCCGGTGCCCGTCAGTGGGCAGAGCGCACATCGCCCACAGTCCCCGAGAAGT

TGGGGGGAGGGGTCGGCAATTGAACGGGTGCCTAGAGAAGGTGGCGCGGGGTAAACTGGGAAAG

TGATGTCGTGTACTGGCTCCGCCTTTTTCCCGAGGGTGGGGGAGAACCGTATATAAGTGCAGTA

GTCGCCGTGAACGTTCTTTTTCGCAACGGGTTTGCCGCCAGAACACAGCTGAAGCTTCGAGGGG

CTCGCATCTCTCCTTCACGCGCCCGCCGCCCTACCTGAGGCCGCCATCCACGCCGGTTGAGTCG

CGTTCTGCCGCCTCCCGCCTGTGGTGCCTCCTGAACTGCGTCCGCCGTCTAGGTAAGTTTAAAG

CTCAGGTCGAGACCGGGCCTTTGTCCGGCGCTCCCTTGGAGCCTACCTAGACTCAGCCGGCTCT

CCACGCTTTGCCTGACCCTGCTTGCTCAACTCTACGTCTTTGTTTCGTTTTCTGTTCTGCGCCG

TTACAGATCCAAGCTGTGACCGGCGCCTACTCTAGAGCTAGCGAATTCGAATTTAAATCGGATC

CGCGGCCGCGCCCCTCTCCCTCCCCCCCCCCTAACGTTACTGGCCGAAGCCGCTTGGAATAAGG

CCGGTGTGCGTTTGTCTATATGTTATTTTCCACCATATTGCCGTCTTTTGGCAATGTGAGGGCC

CGGAAACCTGGCCCTGTCTTCTTGACGAGCATTCCTAGGGGTCTTTCCCCTCTCGCCAAAGGAA

TGCAAGGTCTGTTGAATGTCGTGAAGGAAGCAGTTCCTCTGGAAGCTTCTTGAAGACAAACAAC

GTCTGTAGCGACCCTTTGCAGGCAGCGGAACCCCCCACCTGGCGACAGGTGCCTCTGCGGCCAA

AAGCCACGTGTATAAGATACACCTGCAAAGGCGGCACAACCCCAGTGCCACGTTGTGAGTTGGA

-continued

```
TAGTTGTGGAAAGAGTCAAATGGCTCTCCTCAAGCGTATTCAACAAGGGGCTGAAGGATGCCCA

GAAGGTACCCCATTGTATGGGATCTGATCTGGGGCCTCGGTGCACATGCTTTACATGTGTTTAG

TCGAGGTTAAAAAAACGTCTAGGCCCCCCGAACCACGGGGACGTGGTTTTCCTTTGAAAAACAC

GATGATAATATGGCCACAACCATGGCGTCCGGAATGATTGAACAAGATGGATTGCACGCAGGTT

CTCCGGCCGCTTGGGTGGAGAGGCTATTCGGCTATGACTGGGCACAACAGACAATCGGCTGCTC

TGATGCCGCCGTGTTCCGGCTGTCAGCGCAGGGGCGCCCGGTTCTTTTTGTCAAGACCGACCTG

TCCGGTGCCCTGAATGAACTGCAGGACGAGGCAGCGCGGCTATCGTGGCTGGCCGCGACGGGCG

TTCCTTGCGCAGCTGTGCTCGACGTTGTCACTGAAGCGGGAAGGGACTGGCTGCTATTGGGCGA

AGTGCCGGGGCAGGATCTCCTGTCATCTCACCTTGCTCCTGCCGAGAAAGTATCCATCATGGCT

GATGCAATGCGGCGGCTGCATACGCTTGATCCGGCTACCTGCCCATTCGACCACCAAGCGAAAC

ATCGCATCGAGCGAGCACGTACTCGGATGGAAGCCGGTCTTGTCGATCAGGATGATCTGGACGA

AGAGCATCAGGGGCTCGCGCCAGCCGAACTGTTCGCCAGGCTCAAGGCGCGCATGCCCGACGGC

GAGGATCTCGTCGTGACCCATGGCGATGCCTGCTTGCCGAATATCATGGTGGAAAATGGCCGCT

TTTCTGGATTCATCGACTGTGGCCGGCTGGGTGTGGCGGACCGCTATCAGGACATAGCGTTGGC

TACCCGTGATATTGCTGAAGAGCTTGGCGGCGAATGGGCTGACCGCTTCCTCGTGCTTTACGGT

ATCGCCGCTCCCGATTCGCAGCGCATCGCCTTCTATCGCCTTCTTGACGAGTTCTTCTGAGTCG

ACAATCAACCTCTGGATTACAAAATTTGTGAAAGATTGACTGGTATTCTTAACTATGTTGCTCC

TTTTACGCTATGTGGATACGCTGCTTTAATGCCTTTGTATCATGCGTTAACTAAACTTGTTTAT

TGCAGCTTATAATGGTTACAAATAAAGCAATAGCATCACAAATTTCACAAATAAAGCATTTTTT

TCACTGCATTCTAGTTGTGGTTTGTCCAAACTCATCAATGTATCTTATCATGTCTGGAATTGAC

TCAAATGATGTCAATTAGTCTATCAGAAGCTCATCTGGTCTCCCTTCCGGGGGACAAGACATCC

CTGTTTAATATTTAAACAGCAGTGTTCCCAAACTGGGTTCTTATATCCCTTGCTCTGGTCAACC

AGGTTGCAGGGTTTCCTGTCCTCACAGGAACGAAGTCCCTAAAGAAACAGTGGCAGCCAGGTTT

AGCCCCGGAATTGACTGGATTCCTTTTTTAGGGCCCATTGGTATTATAACAAGAAAATATATAT

ATAATAAGTTATCACGTAAGTAGAACATGAAATAACAATATAATTATCGTATGAGTTAAATCTT

AAAAGTCACGTAAAAGATAATCATGCGTCATTTTGACTCACGCGGTCGTTATAGTTCAAAATCA

GTGACACTTACCGCATTGACAAGCACGCCTCACGGGAGCTCCAAGCGGCGACTGAGATGTCCTA

AATGCACAGCGACGGATTCGCGCTATTTAGAAAGAGAGAGCAATATTTCAAGAATGCATGCGTC

AATTTTACGCAGACTATCTTTCTAGGG
```

The disclosure is based, in part, on vectors for rAAV production that comprise a combination of AAV packaging genes and viral helper functions. "Helper functions" generally refers to nucleic acid sequences encoding non-AAV-derived viral and/or cellular functions upon which AAV is dependent for replication (e.g., "accessory functions"). The accessory functions include those functions required for AAV replication, including, without limitation, those moieties involved in activation of AAV gene transcription, stage-specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some embodiments, a vector as described by the disclosure comprises a nucleic acid encoding and one or more viral (e.g., adenovirus (Ad), etc.) helper elements (e.g., accessory functions). Examples of Ad helper elements include but are not limited to Ad-Ela, Ad-VA, Ad-E2a, Ad-E2b, and Ad-E4. The Ad type from which the one or more helper elements are derived can vary. In some embodiments, the one or more helper elements are Ad1, Ad2, Ad3, Ad4, or Ad5 helper elements. In some embodiments, the helper elements are Ad5 helper elements.

In some embodiments, a vector as described by the disclosure comprises a bacterial plasmid backbone or a bacterial origin of replication (ori). Examples of bacterial origins of replication (ori) include but are not limited to pUC (e.g., pMB1), pBR322 (e.g., pMB1), pET (e.g., pBR322), ColE1, R6K, p15A, and pSC101. In some embodiments, an origin of replication (ori) is a pUC ori. In some embodiments, a vector as described by the disclosure is not a plasmid.

In some embodiments, an rAAV production system comprises a second vector comprising one or more nucleic acids encoding an expression cassette comprising a transgene flanked by adeno-associated virus (AAV) inverted terminal repeat (ITR) sequences (e.g., an rAAV vector).

"Recombinant AAV (rAAV) vectors" are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The instant disclosure provides a vector comprising a single, cis-acting wild-type ITR. In some embodiments, the ITR is a 5' ITR. In some embodiments, the ITR is a 3' ITR Generally, ITR sequences are about 145 bp in length. Preferably, substantially the entire sequences encoding the ITR(s) is used in the molecule, although some degree of minor modification of these sequences is permissible. The ability to modify ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). For example, an ITR may be mutated at its terminal resolution site (TR), which inhibits replication at the vector terminus where the TR has been mutated and results in the formation of a self-complementary AAV. Another example of such a molecule employed in the present disclosure is a "cis-acting" plasmid containing the transgene, in which the selected transgene sequence and associated regulatory elements are flanked by the 5' AAV ITR sequence and a 3' hairpin-forming RNA sequence. AAV ITR sequences may be obtained from any known AAV, including presently identified mammalian AAV types. In some embodiments, an ITR sequence is an AAV2, AAV3, AAV4, AAV5, AAV6, AAV7, AAV8, AAVrh8, AAV9, AAV10, and/or AAVrh10 ITR sequence.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

Aspects of the disclosure relate to gene therapy vectors comprising an isolated nucleic acid as described herein. A gene therapy vector may be a viral vector (e.g., a lentiviral vector, an adeno-associated virus vector, etc.), a plasmid, a closed-ended DNA (e.g., ceDNA), etc. In some embodiments, a gene therapy vector is a viral vector. In some embodiments, an expression cassette encoding a minigene is flanked by one or more viral replication sequences, for example lentiviral long terminal repeats (LTRs) or adeno-associated virus (AAV) inverted terminal repeats (ITRs).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4:928-933; Mattion, N M et al., J Virology, November 1996; p. 8124-8127; Furler, S et al., Gene Therapy, 2001; 8:864-873; and Halpin, C et al., The Plant Journal, 1999; 4:453-459). The cleavage activity of the 2A sequence has previously been demonstrated in artificial systems including plasmids and gene therapy vectors (AAV and retroviruses) (Ryan, M D et al., EMBO, 1994; 4:928-933; Mattion, N M et al., J Virology, November 1996; p. 8124-8127; Furler, S et al., Gene Therapy, 2001; 8:864-873; and Halpin, C et al., The Plant Journal, 1999; 4:453-459; de Felipe, P et al., Gene Therapy, 1999; 6:198-208; de Felipe, P et al., Human Gene Therapy, 2000; 11:1921-1931.; and Klump, H et al., Gene Therapy, 2001; 8:811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, a promoter is an RNA polymerase II (pol II) promoter or an RNA polymerase III (pol III) promoter. In some embodiments, a promoter is a H1, U6, CB, CBA, CB6, Desmin, CMV, AAT, or MHK promoter The disclosure relates, in some aspects, to isolated nucleic acids and vectors (e.g., rAAV vectors) comprising one or more nucleic acids sequences encoding a transgene. The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Thus, the disclosure embraces the delivery of vectors encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10 (187A), viral IL-10, IL-11, IL-12, IL-13, IL-14, IL-15, IL-16 IL-17, and IL-18.

The vectors disclosed herein may comprise a transgene to be transferred to a subject to treat a disease associated with reduced expression, lack of expression or dysfunction of the native gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; omithine transcarbamylase, associated with omithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent *porphyria*; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco (endo) plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

The following are further non-limiting examples of proteins that may be encoded by transgenes of the vectors disclosed herein to treat a disease associated with reduced expression, lack of expression or dysfunction of the native gene: a-galactosidase, acid-glucosidase, adiopokines, adiponectin, alglucosidase alfa, anti-thrombin, ApoAV, ApoCII, apolipoprotein A-I (APOA1), arylsulfatase A, arylsulfatase B, ATP-binding cassette transporter A1 (ABCA1), ABCD1, CCR5 receptor, erythropoietin, Factor VIII, Factor VII, Factor IX, Factor V, fetal hemoglobin, beta-globin, GPI-anchored HDL-binding protein (GPI-HBP) I, growth hormone, hepatocyte growth factor, imiglucerase, lecithin-cholesterol acyltransferase (LCAT), leptin, LDL receptor, lipase maturation factor (LMF) 1, lipoprotein lipase, lysozyme, nicotinamide dinucleotide phosphate (NADPH) oxidase, Rab escort protein-1 (REP-1), retinal degeneration slow (RDS), retinal pigment epithelium-specific 65 (RPE65), rhodopsin, T cell receptor alpha or beta chains, thrombopoeitin, tyrosine hydroxylase, VEGF, von heldebrant factor, von willebrand factor, and X-linked inhibitor of apoptosis (XIAP).

In some aspects, the disclosure relates to rAAVs and rAAV vectors comprising a transgene, wherein the transgene is a hairpin-forming RNA. Non-limiting examples of hairpin-forming RNA include short hairpin RNA (shRNA), microRNA (miRNA) and artificial microRNA (AmiRNA). In some embodiments, nucleic acids are provided herein that contain or encode the target recognition and binding sequences (e.g., a seed sequence or a sequence complementary to a target) of any one of the inhibitory RNAs (e.g., shRNA, miRNA, AmiRNA) disclosed herein.

Generally, hairpin-forming RNAs are arranged into a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue.

Hairpin-forming RNA are useful for translational repression and/or gene silencing via the RNAi pathway. Due to having a common secondary structure, hairpin-forming RNA share the characteristic of being processed by the proteins Drosha and Dicer prior to being loaded into the RNA-induced silencing complex (RISC). Duplex length amongst hairpin-forming RNA can vary. In some embodiments, a duplex is between about 19 nucleotides and about 200 nucleotides in length. In some embodiments, a duplex is between about between about 14 nucleotides to about 35 nucleotides in length. In some embodiments, a duplex is between about 19 and 150 nucleotides in length. In some embodiments, hairpin-forming RNA has a duplex region that is 19, 20, 21, 22, 23, 24, 25, 26, 27, 28, 29, 30, 31, 32, or 33 nucleotides in length. In some embodiments, a duplex is between about 19 nucleotides and 33 nucleotides in length. In some embodiments, a duplex is between about 40 nucleotides and 100 nucleotides in length. In some embodiments, a duplex is between about 60 and about 80 nucleotides in length.

In some embodiments, the hairpin-forming RNA is a microRNA (miRNA), or artificial microRNA (AmiRNA). A microRNA (miRNA) is a small non-coding RNA found in plants and animals and functions in transcriptional and post-translational regulation of gene expression. An artificial microRNA (AmiRNA) is derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest. An artificial precursor microRNA (pre-amiRNA) is normally processed such that one single stable small RNA is preferentially generated. In some embodiments, scAAV vectors and scAAVs described herein comprise a nucleic acid encoding an AmiRNA. In some embodiments, the pri-miRNA scaffold of the AmiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

In some aspects, the disclosure relates to rAAV comprising a combination of hairpin-forming nucleic acid and a protein coding gene. rAAV vectors comprising an interfering nucleic acid and a protein coding gene are useful for simultaneously performing gene silencing and gene substitution. For example, rAAV vectors described herein can be used to silence a defective gene (e.g., mutated SOD1) while simultaneously delivering a non-mutated or functional copy of the defective gene (e.g., wild-type SOD1).

Host Cells

In some embodiments, a rAAV production system as described by the disclosure further comprises a host cell. A "host cell" refers to any cell that harbors, or is capable of harboring, a substance of interest. In some embodiments, a host cell is a eukaryotic cell. In some embodiments, a host cell is a mammalian cell. In some embodiments, a mammalian cell is a HEK293 cell, a HEK293T cell, a HeLa cell, a A549 cell, or a Chinese hamster ovary (CHO) cell. In some embodiments, a host cell is a bacterial cell, for example an *E. coli* cell.

A host cell may be used as a recipient of an isolated nucleic acid or vector as described herein, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the term "stable cell line" refers to a genome in which the information content of the genome from one generation to the next is maintained.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

The disclosure is based, in part, on isolated nucleic acids and vectors that comprise components needed to replicate and package recombinant adeno-associated virus particles. In some embodiments, an isolated nucleic acid or vector as described herein lacks one or more genes required for replication and/or packaging of rAAV. In some embodiments, an isolated nucleic acid or vector as described herein lacks Ad Ela helper element. In some embodiments, a host cell expresses (or is capable of expressing) the one or more helper elements missing from the isolated nucleic acid or vector. For example, in some embodiments, a host cell expresses Adenovirus helper element Ad-Ela. In some embodiments the Ad-Ela is integrated into the genome of the host cell (e.g., HEK293 cells). In some embodiments, the Ad-Ela is introduced into a host cell and/or transiently expressed in a host cell (e.g., CHO cells).

rAAV Production Methods

In some aspects, the disclosure provides methods for producing a recombinant adeno-associated virus (rAAV), comprising the step of introducing an rAAV production system as described by the disclosure into a host cell that expresses an Ad-Ela helper function.

Generally, methods described by the disclosure involve transfecting a population of host cells (e.g., host cells expressing Ad-Ela) one or more vectors. In some embodiments, the cap gene and the mutated rep gene as provided by this disclosure are present in the host cell, for example, they are stably integrated in the host cell genome. In some embodiments, the mutated rep gene as described by this disclosure but not the cap gene are present in the host cell, for example, being stably integrated in the host cell genome. In some embodiments, orthogonal aminoacyl-tRNA synthetase-tRNA pairs are present in the host cell genome, to which ncAAs can be supplied. In some embodiments, the one or more vectors comprise Adenoviral helper elements (e.g., Ad5-VA, Ad5-E2a, Ad5-E2b, or Ad5-E4), and/or anticodon engineered synthetic suppressor tRNAs, and/or rAAV cap genes. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells. In some embodiments, the more than one vector of an rAAV production system are introduced into the host cell in a single transfection reaction. In some embodiments, a first vector and second vector of an rAAV production system are introduced into the host cell in separate transfection reactions.

After transfection with the isolated nucleic acids and/or vectors described herein, the host cells can be cultured in the presence of an antibiotic agent that is cognate to the antibiotic-resistance gene of the first vector (e.g., the first vector of the rAAV production system). For example, in some embodiments, a vector comprises an kanR gene and the transfected host cells are cultured in the presence of kanamycin. The concentration of antibiotic agent present in the culture media can vary. In some embodiments, the concentration of antibiotic agent in the culture media ranges from about 5-100 μg/mL (e.g., any amount between 5 and 100 μg/mL, inclusive).

In some embodiments, methods described by the disclosure further comprise the step of supplementing the cell culture after transfection with cognate non-canonical amino acid (ncAA) for the expression of a functional rep gene. In some embodiments, methods described by the disclosure further comprise the step of supplementing the cell culture after transfection with a read-through small molecule for the expression of a functional rep gene.

In some embodiments, methods described by the disclosure further comprise the step of isolating rAAV particles (e.g., rAAV particles comprising the transgene) from the host cells and/or cell culture media. Methods of rAAV purification are known in the art and are described, for example by WO2010148143, WO2016/114992, Potter et al. Mol Ther Methods Clin Dev. 2014; 1:14034, and Wang et al. Methods Mol Biol. 2011; 807:361-404.

The disclosure relates, in part, to cell culture systems comprising rAAV production systems described herein. In some aspects, the disclosure provides an apparatus for production of recombinant adeno-associated virus (rAAV) particles, the apparatus comprising: a container housing an rAAV production system as described herein; and, a population of host cells, wherein the rAAV production system and the host cells are suspended in a cell culture medium.

In some embodiments, the container is a cell culture flask, cell culture plate, a beaker, or a cell culture bag. In some embodiments, the cell culture medium is a mammalian cell culture medium. Examples of cell culture media are described, for example, by Yao et al. (2017) Reproductive Medicine and Biology 16 (2): 99-117.

The disclosure is based, in part, on the recognition that transformation of host cells with isolated nucleic acids and vectors (e.g., rAAV production systems) described by the disclosure allow for production of rAAV viral particles that is cost and time-efficient relative to currently available rAAV production methods (e.g., the triple-transfection method). Methods of measuring viral titer (and/or viral genome copy number) are known in the art and include, for example, silver-stain gel analysis, digital droplet (dd) polymerase chain reaction (ddPCR), and microscopic image analysis. In some embodiments, methods as described by the disclosure produce a viral titer of less than $10^{16}$ rAAV particles (e.g., $10^{15}$, $10^{14}$, $10^{13}$, $10^{12}$, $10^{11}$, $10^{10}$, etc.). In some embodiments, a titer between $10^{10}$ and $10^{16}$ (e.g., $10^{15}$, $10^{14}$, $10^{13}$, $10^{12}$, $10^{11}$, $10^{10}$, or any integer therebetween) rAAV particles are produced.

EXAMPLES

Example 1

Gene therapy holds a great promise for curing diseases that are not currently addressed by conventional medicine, including many rare diseases. The adeno-associated virus (AAV) has been widely used to deliver a genetic payload to a target tissue. Significant progress has been made in delineating AAV vectors of high therapeutic efficacy that target a specific tissue. To this end, the AAV vectors have been used in a significant number of clinical trials as well as commercialized gene therapy products. However, AAV based gene therapy products are expensive mainly due to the complexity of AAV vector production. Currently, the widely adopted vector manufacturing scheme, which relies on plasmid transfection, is not only expensive but is also time consuming to the extent that it could not meet the required doses for some clinical trials. Much effort has been put into developing a vector manufacturing scheme based on a producer cell line platform, which circumvents plasmid transfection, without success. Adenoviral early gene (E1) mediated activation of AAV rep gene is cytotoxic and genotoxic, which hinders the development of a stable producer cell line that carries the rep gene.

Described herein is a novel approach to manufacturing AAV using a stable cell line expressing the rep gene that bypasses the need for repeated rep gene transfection during the AAV manufacturing process. Engineered tRNA was used to suppress the mutations introduced beforehand to the rep gene that is integrated to the genome of a cell line. Overall, this approach can obviate the need for plasmid transfection and can greatly facilitates a scale-up of AAV manufacturing.

A strategy for developing an AAV manufacturing cell lines was designed, which capitalized on the read-through activity of the engineered tRNA. Rep genes containing amber or frame shift mutations, which knock out its function, were integrated into the genome of a cell line. Anticodon engineered tRNA, or orthogonal aminoacyl-tRNA synthetase-tRNA pairs, were used to suppress the mutation introduced to the rep gene, thereby allowing functionally expressed rep gene.

Single and multiple amber mutations coupled with or without frameshift mutations were introduced to completely knock out the rep gene integrated to the genome of a cell line. Depending on the need of manufacturing, this AAV production cell line platform was designed to be induced in different ways. By creating a stable cell line expressing orthogonal aminoacyl-tRNA synthetase-tRNA pairs and the mutated rep gene, viral packaging can be initiated by simply supplementing the cognate non-canonical amino acid (ncAA). A four-base codon/anticodon strategy was used to rescue a strong stop and frame shift mutation introduced to the rep gene.

Alternatively, the manufacturing was designed to be initiated by the infection a cell line carrying the mutated rep gene with the adenovirus expressing engineered tRNA. The various AAV production schemes that were designed are depicted in FIG. 1.

Figure 2A:
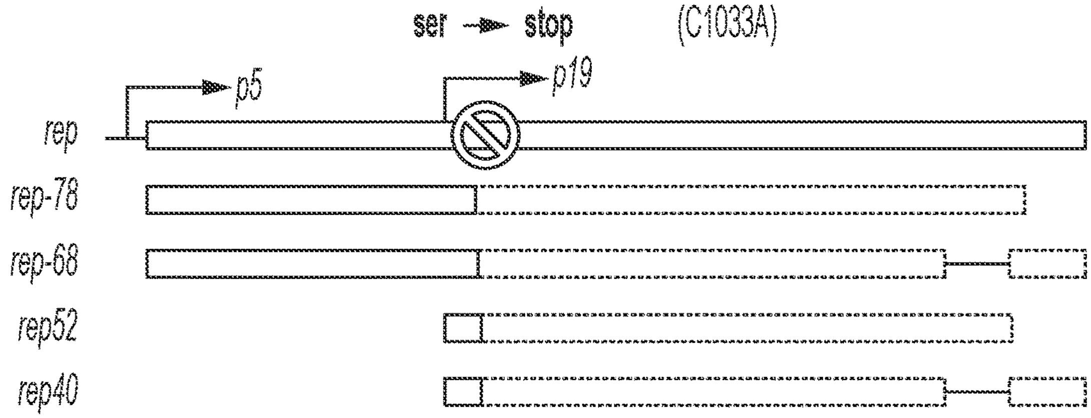
FIGS. 2A-2B show the design of inducible rep gene and experiments.
Figure 2B:
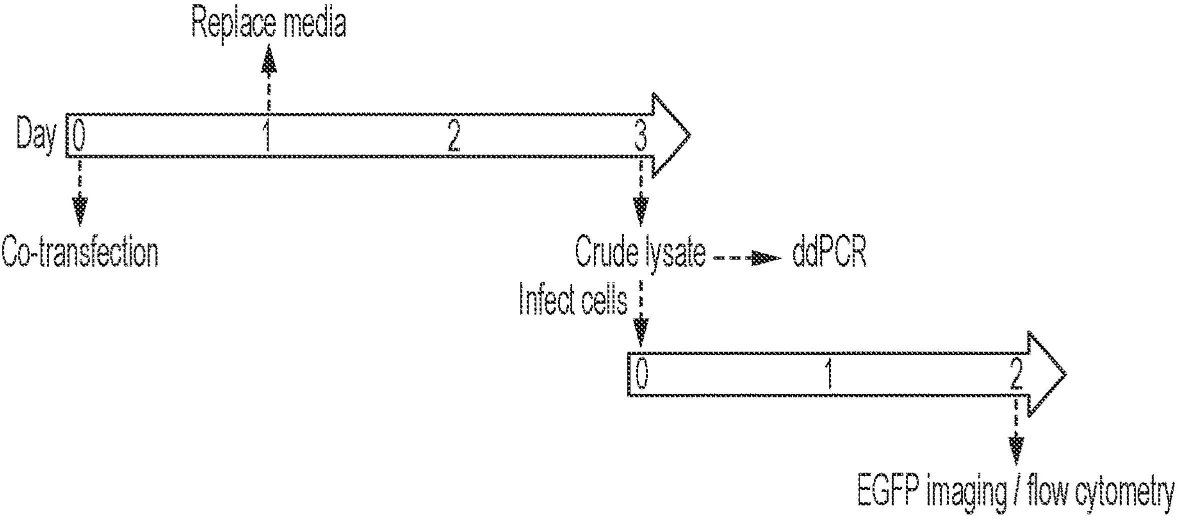
Figure 3A:
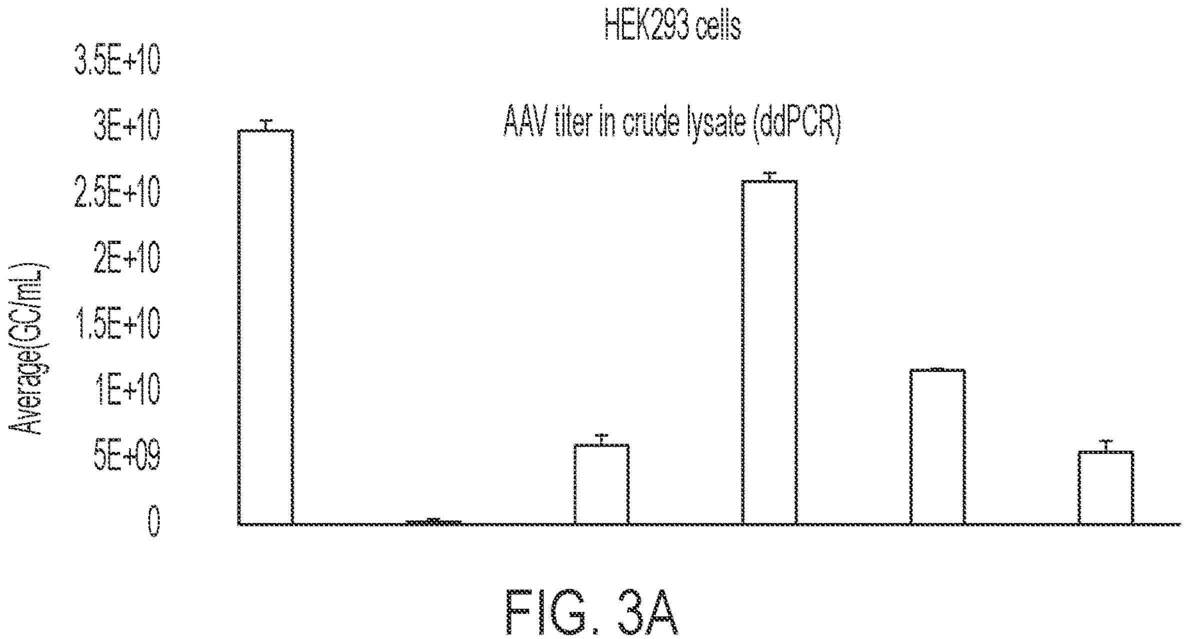
FIGS. 3A-3C show anticodon engineered tRNA suppression of mutant rep to restore AAV production.
Figure 3B:
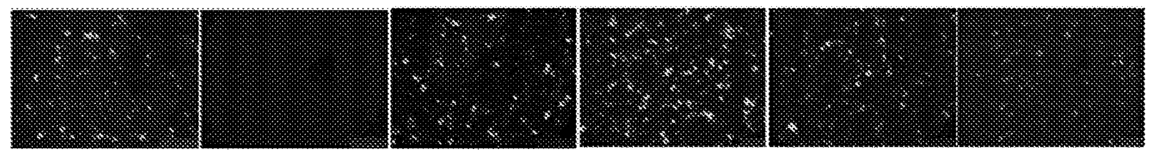
Figure 3C:
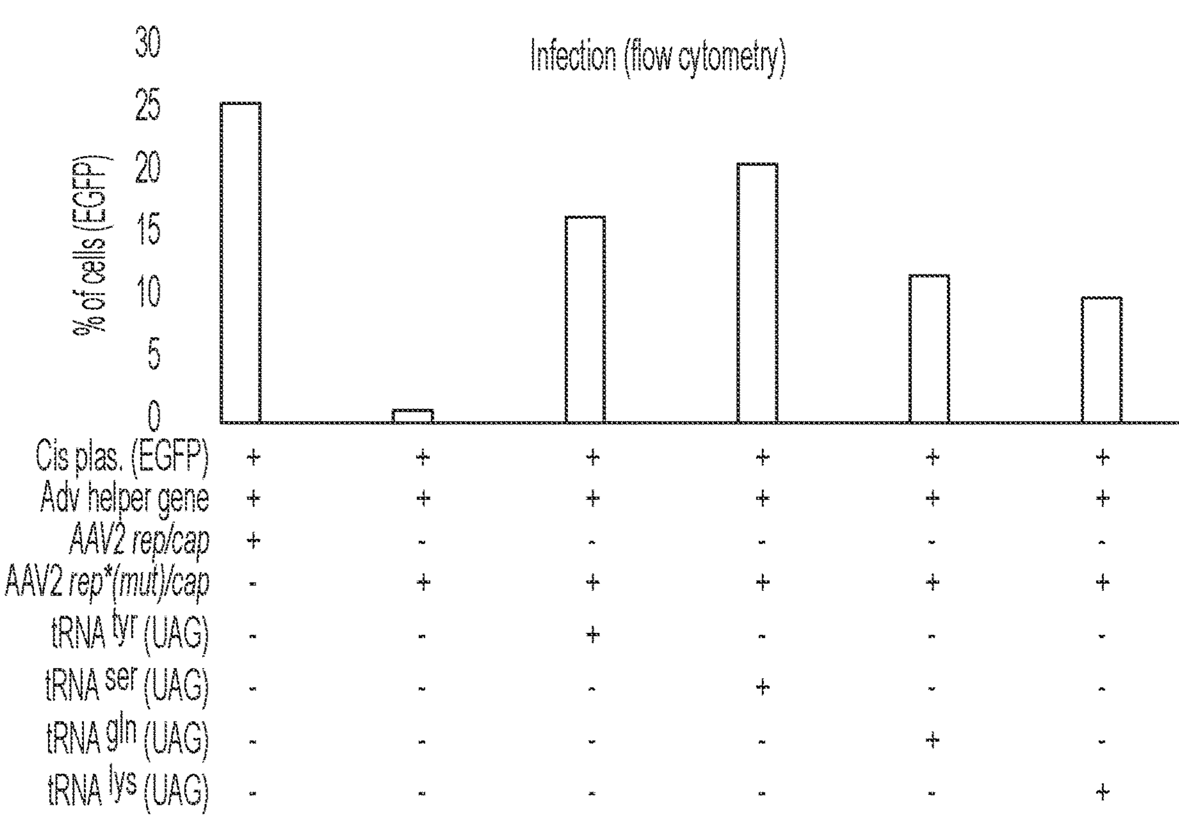

A mutation was introduced to the rep gene that prematurely stops the translation of all four rep proteins (FIG. 2A). In addition to introducing the plasmid carrying the mutated rep gene to the HEK293 cell lines, a different anticodon engineered tRNA expressing plasmid was also added to the transfection mix containing EGFP cis-packaging and adenoviral helper gene plasmids (FIG. 2B). Three days post-transfection, the viral titer in the crude lysate was measured via ddPCR. The expression of all four anticodon engineered tRNA resulted in higher viral titers compared to the control. Notably, tRNAser (UAG) resulted in viral titers close to the wild-type rep control, which restores the native serine amino acid (FIG. 3A). To check the infectivity, a co-infected HEK293 cell line was co-infected with both the adenovirus and the AAV virus thus produced. Successful infection of AAV was confirmed by analyzing EGFP fluorescence two days post infection by florescent microscope and flow cytometry (FIGS. 3A-3C). Consistent with the viral titer demonstrated by ddPCR, cells infected with AAV produced by tRNAser (UAG) expressing tRNA resulted in higher infectivity.

Figure 4A:
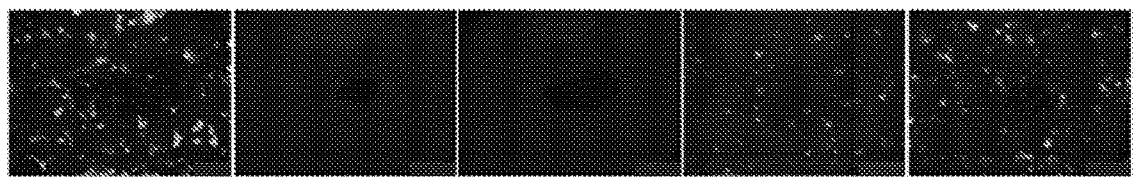
FIGS. 4A-4B show orthogonal aminoacyl-tRNA synthetase/tRNA suppression of the mutant rep to restore AAV production.
Figure 4B:
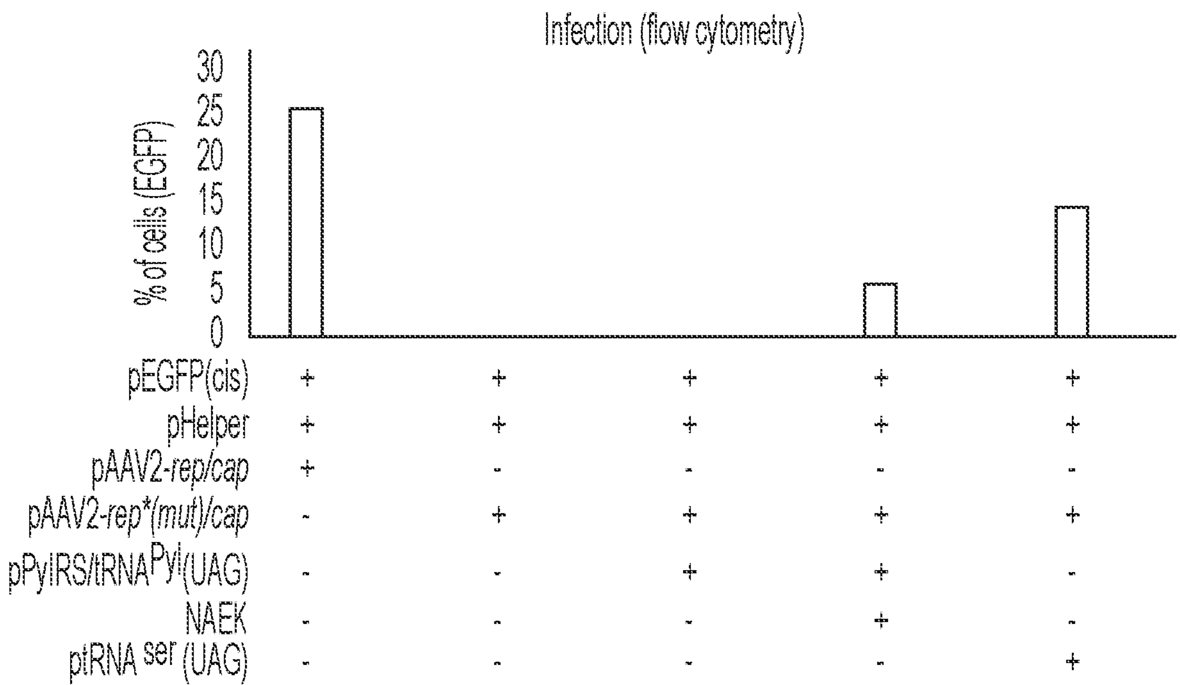

In addition, orthogonal aminoacyl-tRNA synthetase-tRNA pairs (aaRS/tRNA) were utilized to induce the AAV production by supplementing the non-canonical amino acid, NAEK, one day post transfection (FIGS. 4A-4B). In this scheme, both rep expression and AAV production were dependent on the introduction of an ncAA, allowing for the generation of stable cell line with mutant rep genes.

Example 2

Figure 5A:
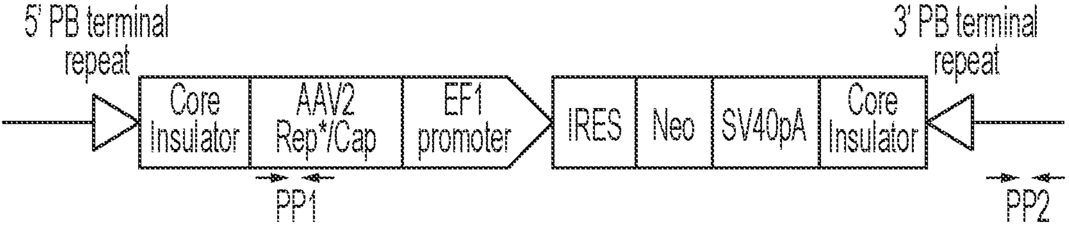
FIGS. 5A-5D show production of AAV using a rep*/cap producer cell line.
Figure 5B:
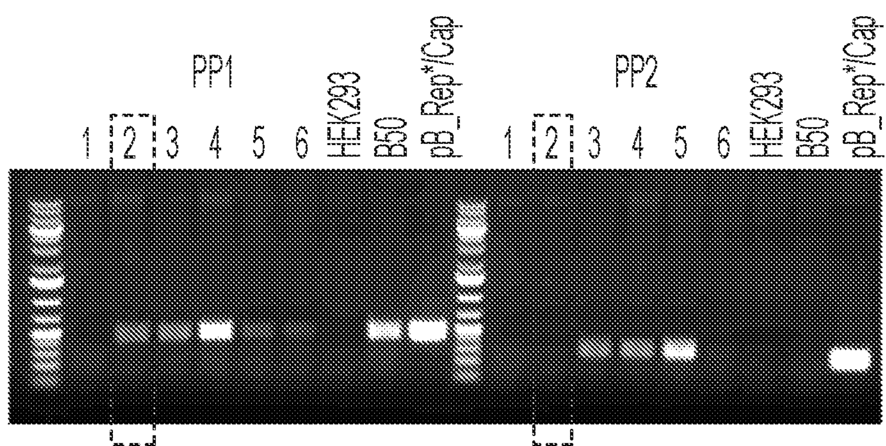
Figure 5C:
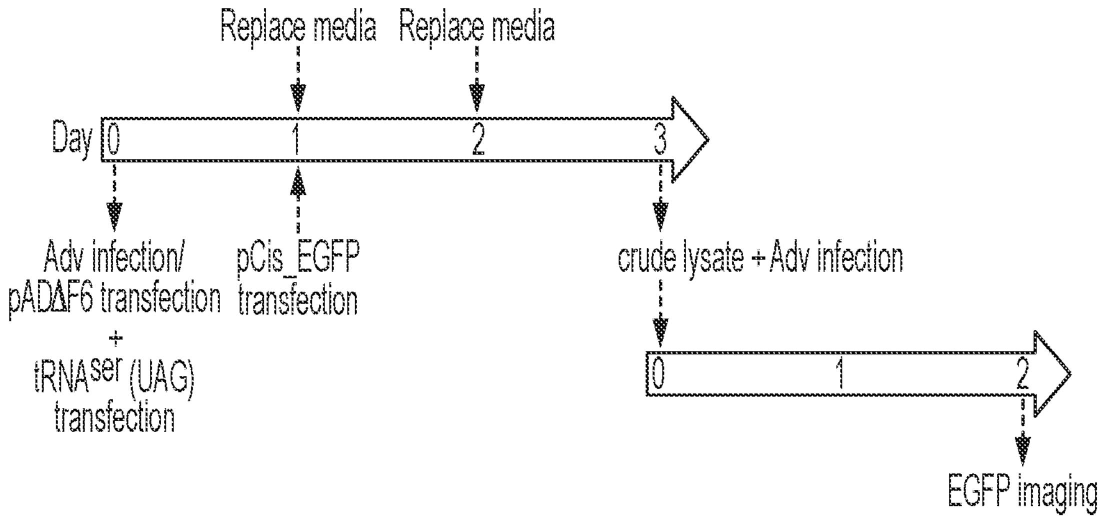
Figure 5D:
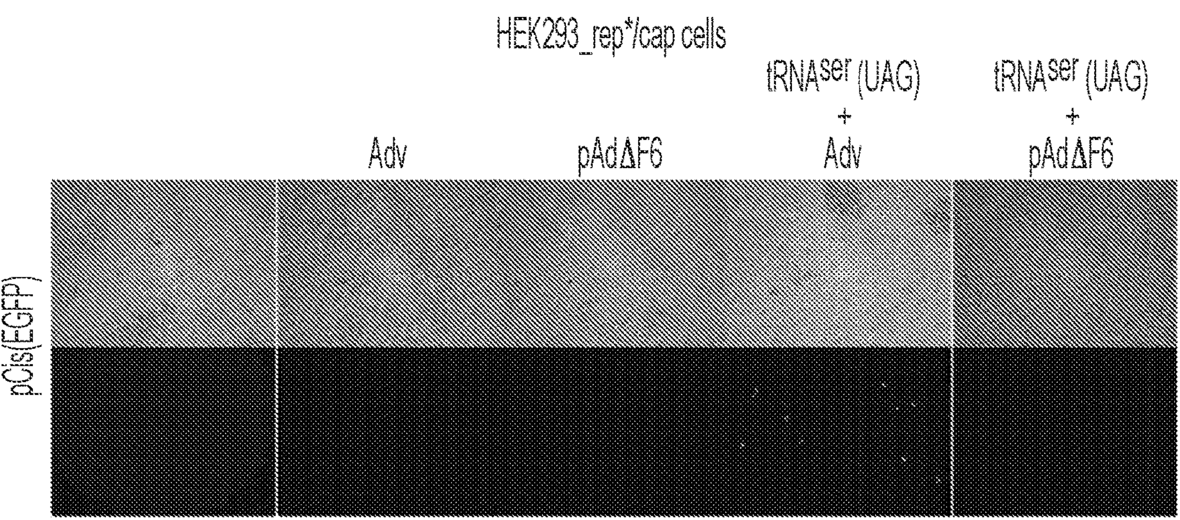

FIGS. 5A-5D show production of AAV using a rep*/cap producer cell line. FIG. 5A shows a schematic depicting a piggybac transposon construct used to create a rep*/cap cell line. The two primer pairs used for genotyping PCR are shown by the arrows. FIG. 5B shows an image of genotyping PCR of agarose gel electrophoresis. Six putative cell lines were genotyped. Cell line #2 marked by dotted rectangle is used in the next experiments. FIG. 5C shows a flowchart showing the experimental layout. FIG. 5D shows representative GFP and bright-field images of cells two days after co-infection with crude lysate and adenovirus.

Figure 6A:
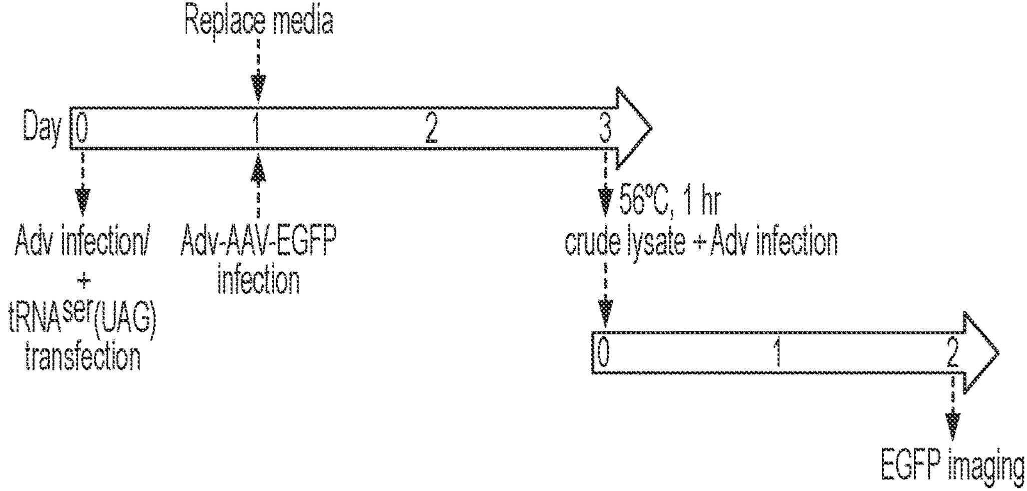
FIGS. 6A-6B show production of AAV using a rep*/cap cell line and Adenovirus-AAV hybrid.
Figure 6B:
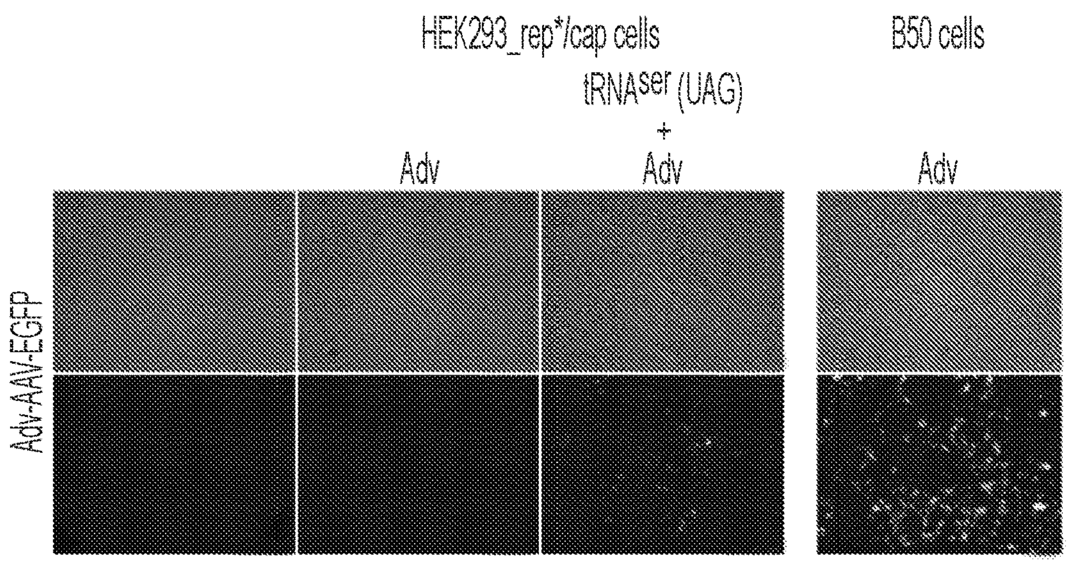

FIGS. 6A-6B show production of AAV using a rep*/cap cell line and Adenovirus-AAV hybrid. FIG. 6A shows a flowchart depicting the experimental layout. FIG. 6B shows representative GFP and bright-field images of cells two days after co-infection with crude lysate and adenovirus.

Figure 7A:
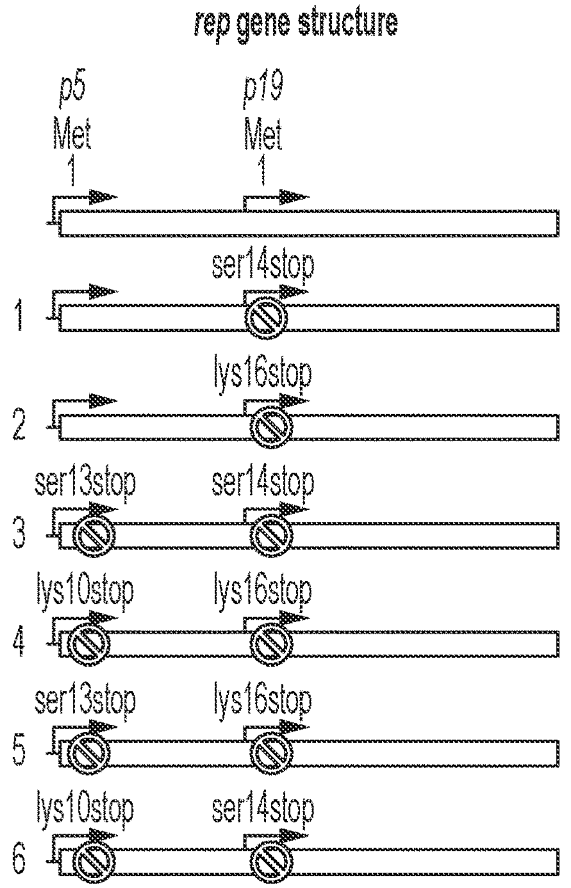
FIGS. 7A-7B show AAV production by suppressing various rep mutants.
Figure 7B:
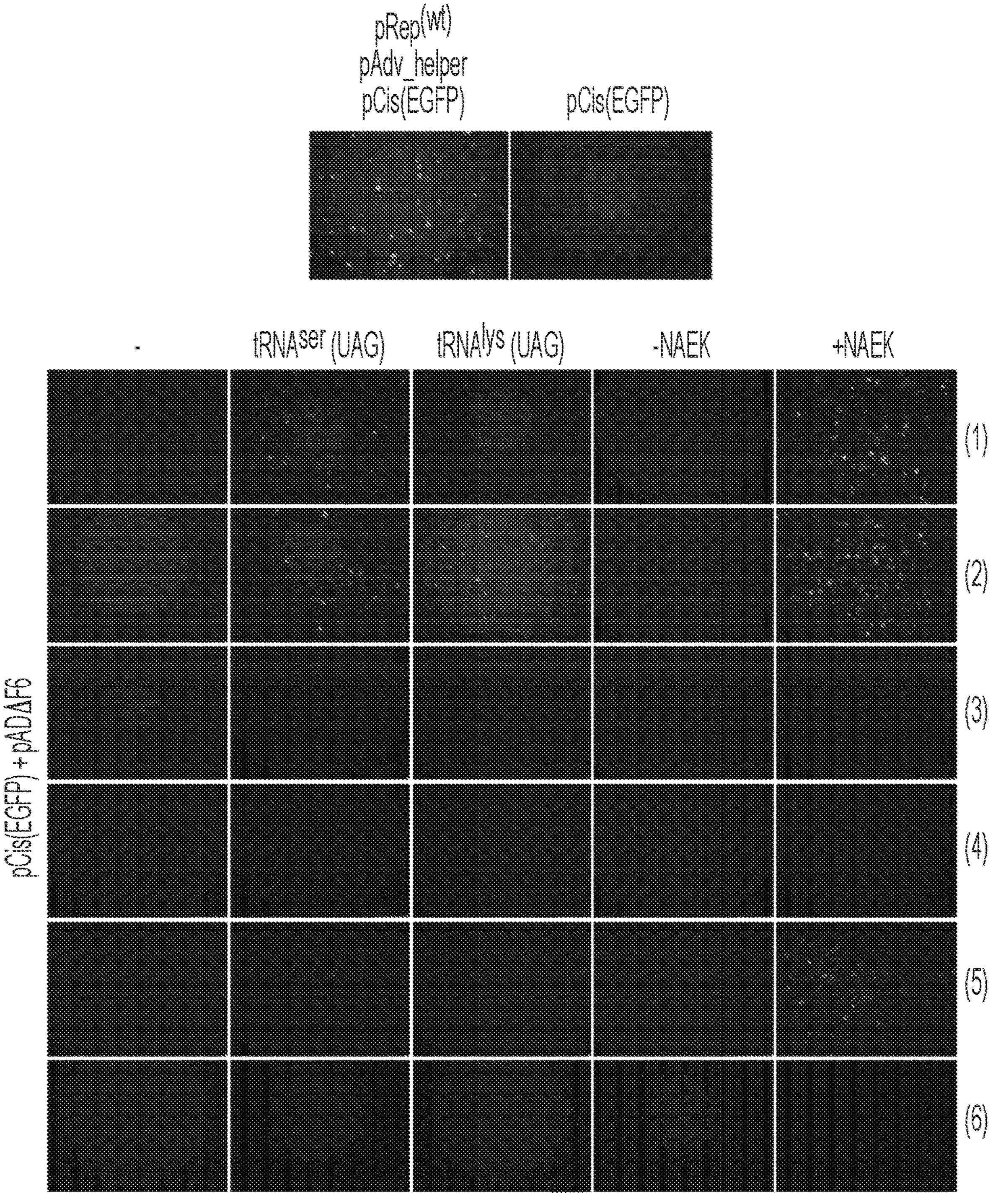

FIGS. 7A-7B show AAV production by suppressing various rep mutants. FIG. 7A shows a schematic depicting rep gene structure with amber mutations at different locations. The mutation position on the left and right side of the rep gene structure corresponds to the Met starting position for the large (REP78 and REP68) and small (REP52 and REP40) protein driven by p5 and p19, respectively. FIG. 7B shows representative GFP images of cells two days after co-infection of HRK293 cells with crude lysate and adenovirus. NAEK is added to a final concentration of 1 mM.

Example 3

Figure 8A:
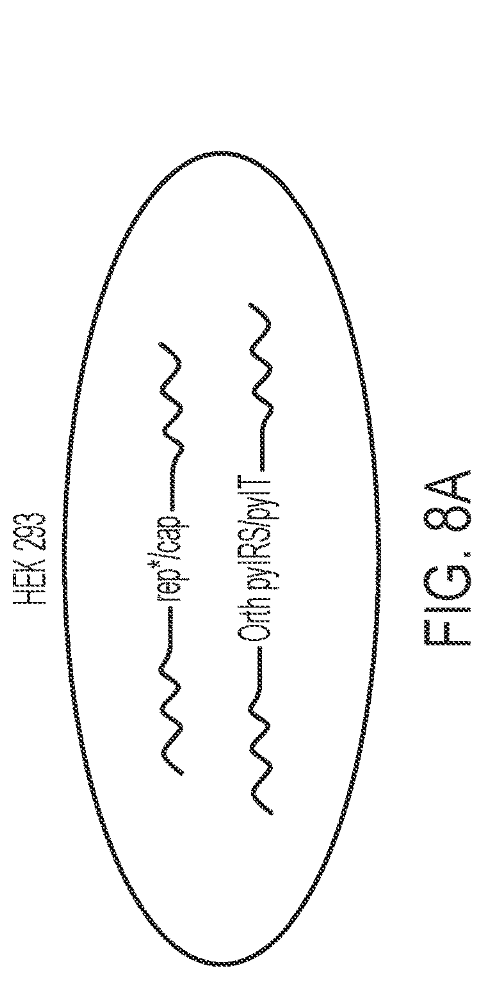
FIGS. 8A-8E show that the HEK293 cell line harboring an orthogonal pyrrolysyl-tRNA system supports plasmid-free rAAV production.
Figure 8B:
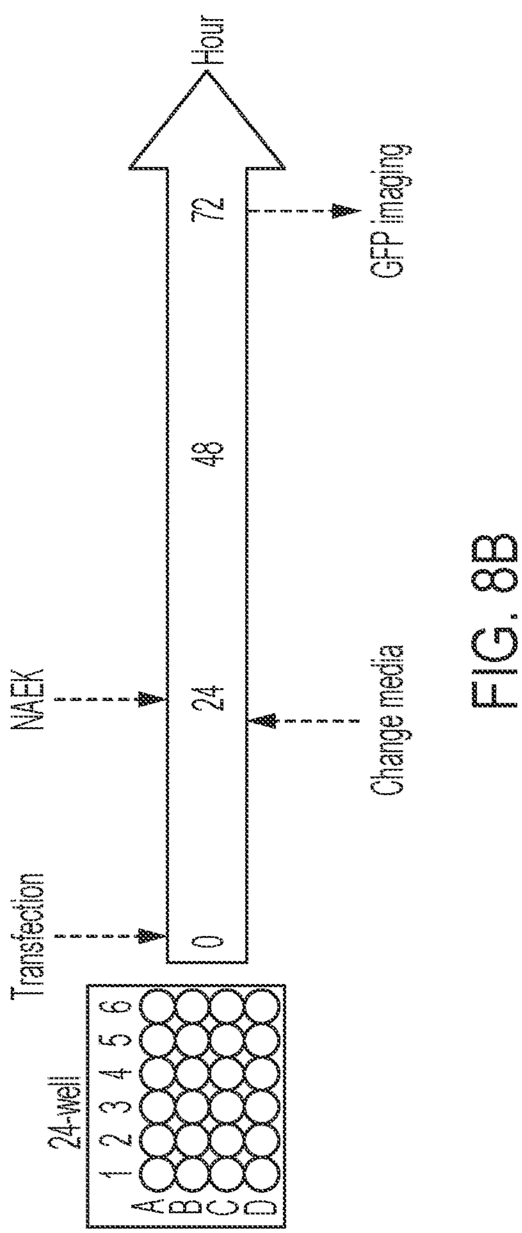
Figure 8C:
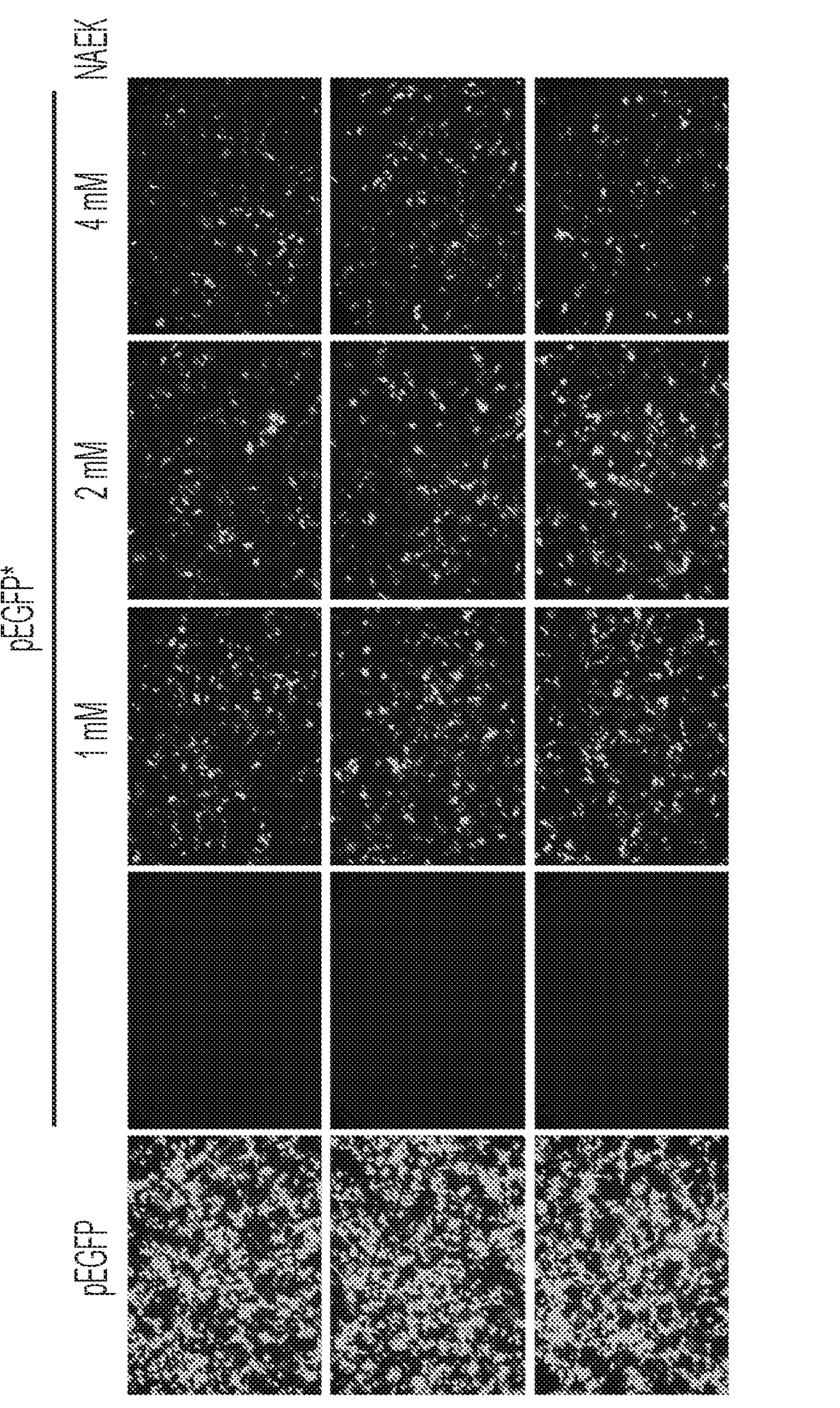

An HEK293 cell line harboring a mutant rep (C714A)/cap and orthogonal Pyrrolysyl-tRNA synthetase/pyltRNA pair was generated using a piggybac transposon system. FIG. 8A shows a cartoon of a cell line containing Rep*(C714A)/Cap and orthogonal Pyrrolysyl-tRNA synthetase/pyltRNA pair. The cells were first transfected with a plasmid encoding either wild type EGFP or a mutant EGFP (Y39X) as reporter for the read through ability once the cells were supplemented with a non-canonical amin acid (ncAA). NAEK was supplemented to the media to a final concentration of 1 mM, 2 mM and 4 mM, 24 hours post-transfection. EGFP expression was evaluated 72 hours post-transfection (FIG. 8B). As shown in FIG. 8C, NEAK supplementation at 1 mM, 2 mM and 4 mM induced EGFP expression in cells transfected with the mutant Y39X EGFP. 4 mM NEAK is less efficient in inducing EGFP expression probably because NEAK is acidic, and high concentration of NEAK in cell culture may be toxic to cells.

Figure 8D:
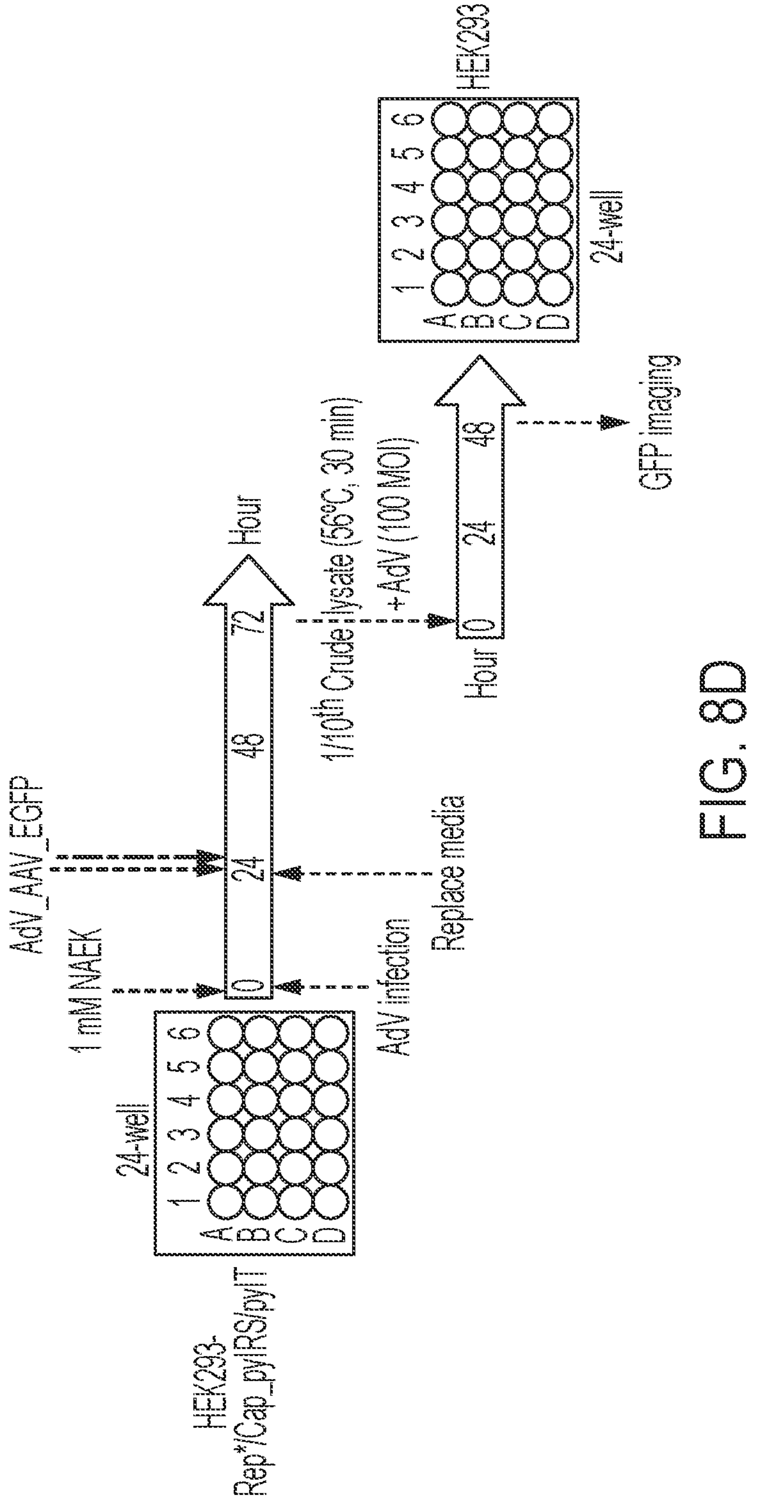
Figure 8E:
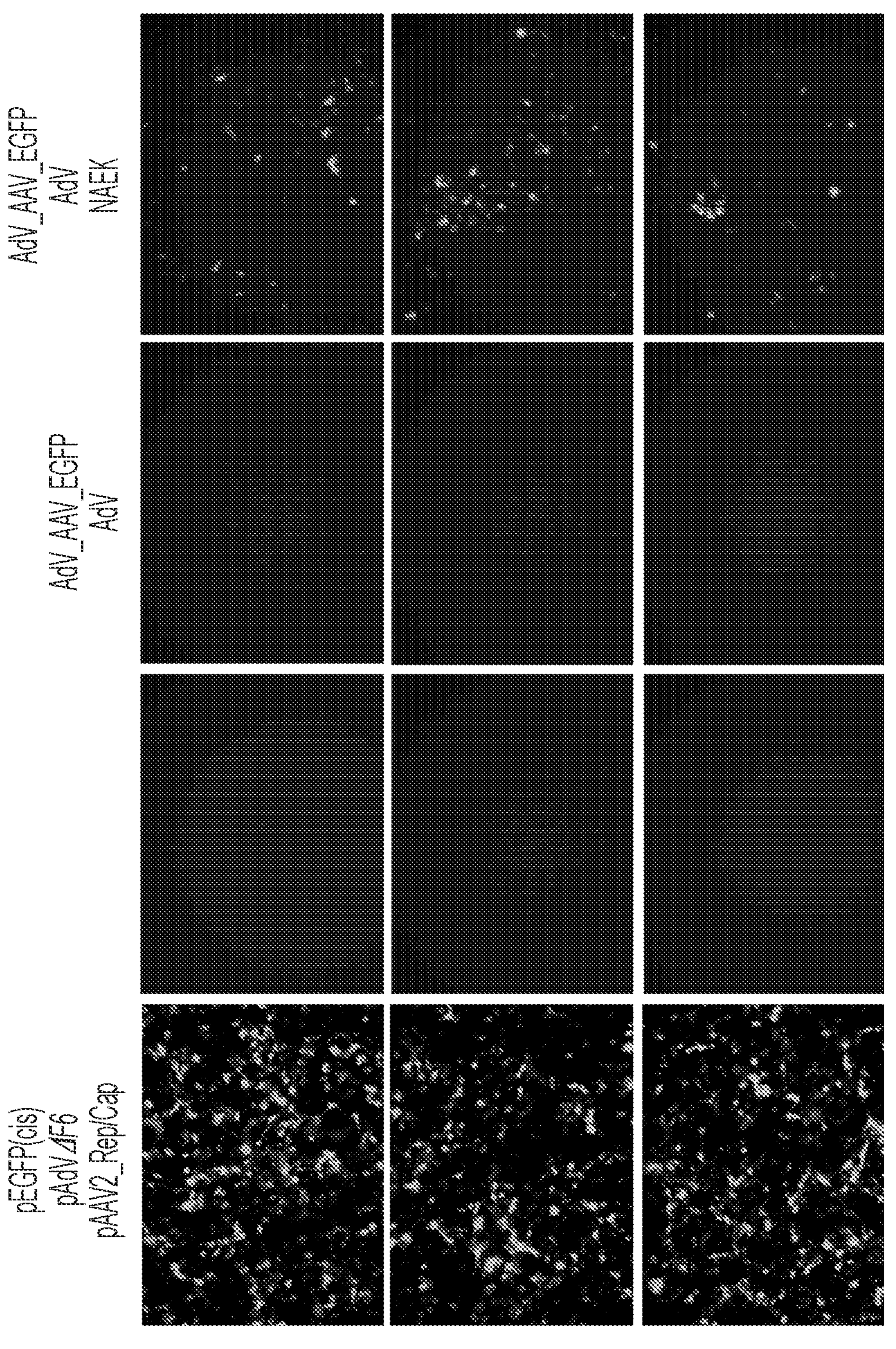

Further, the ability of the HEK293 cells harboring the mutant rep (C714A)/cap and orthogonal Pyrrolysyl-tRNA synthetase/pyltRNA pair in producing rAAV was evaluated. The HEK cells were sequentially infected with Adv5 and hybrid AdV-AAV-EGFP 24 hours apart, after treating cells with NAEK to a final concentration of 1 mM. Crude lysate was harvested 72 hours post initial infection and heat treated at 56° C. for 30 min. Heat inactivation at 56° C. eliminated the adenovirus in the lysate, thus ensuring the transduction of cells were due to the rAAV in the crud lysate. 1/10th of the crude lysate was used to infect new HEK293 cells (FIG. 8D). As shown in FIG. 8E, the crude lysate from HEK293 cells supplemented with 1 mM NEAK successfully infected new HEK293 cells, indicating that NEAK induced read through of the mutant rep gene, thereby leading to successful rAAV packaging.

Figure 9A:
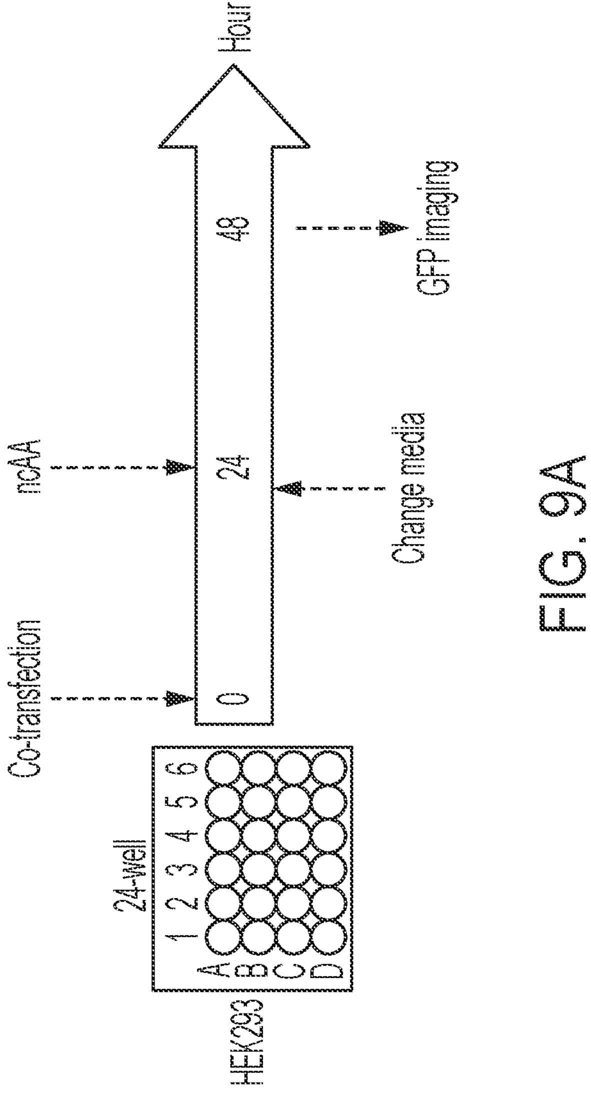
FIGS. 9A-9D show graphs testing different ncAA as an inducer for AAV production.
Figure 9B:
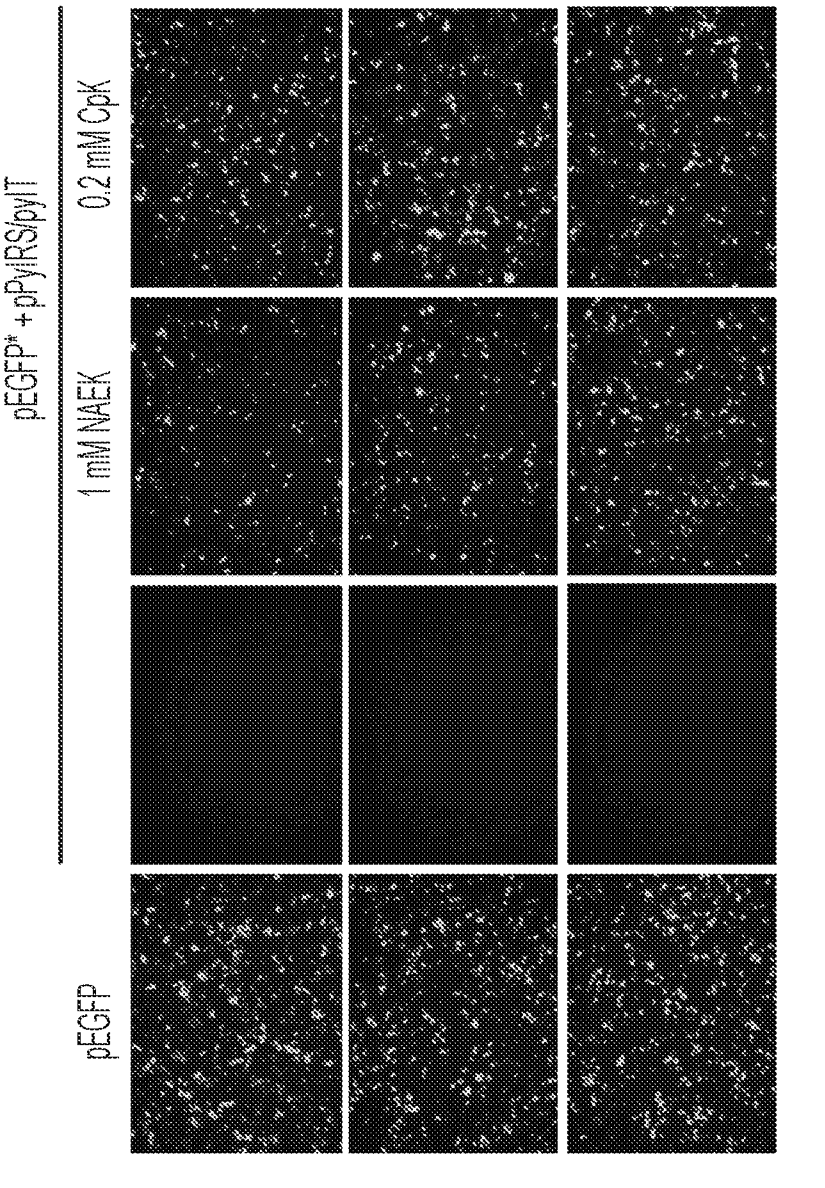
Figure 9C:
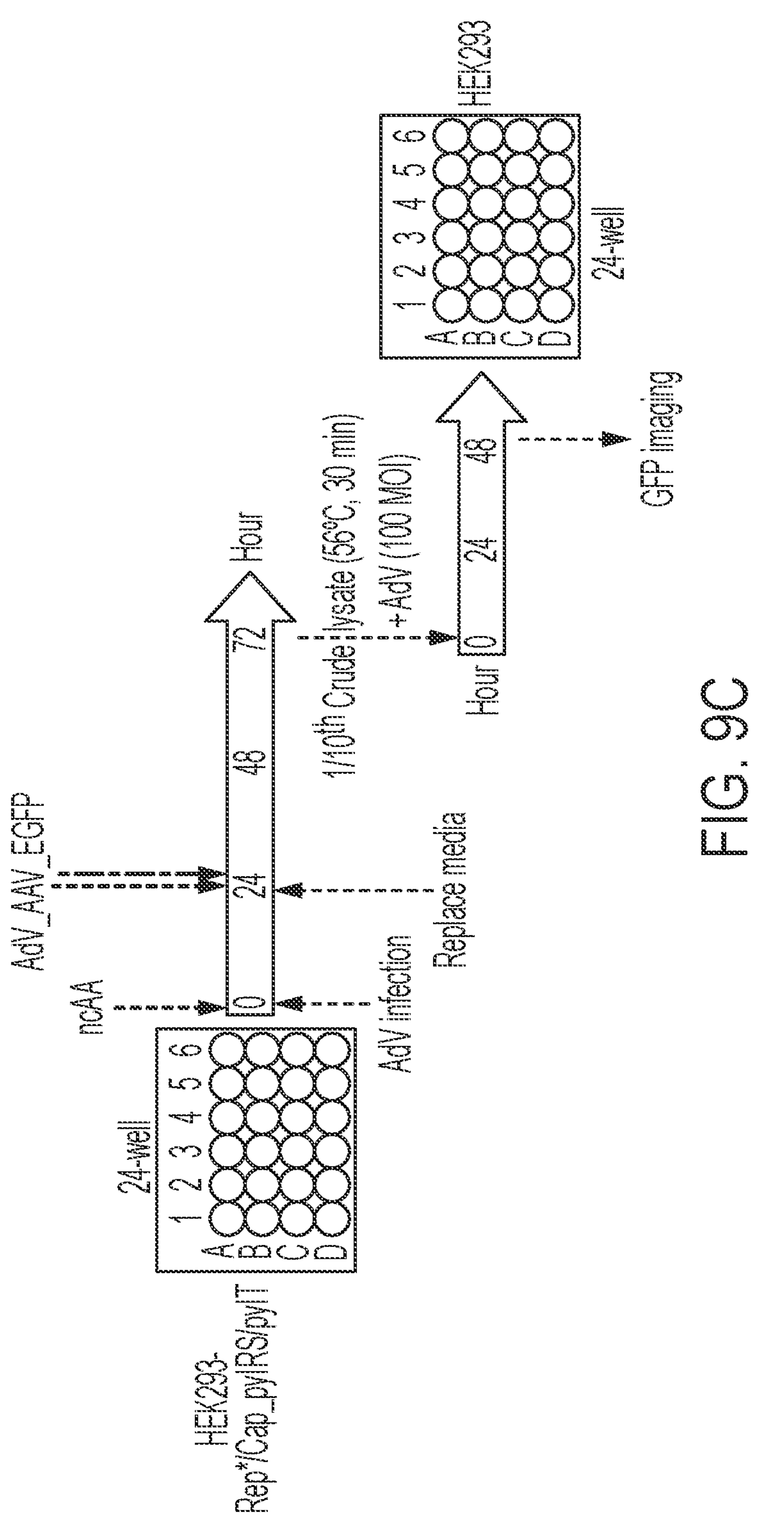
Figure 9D:
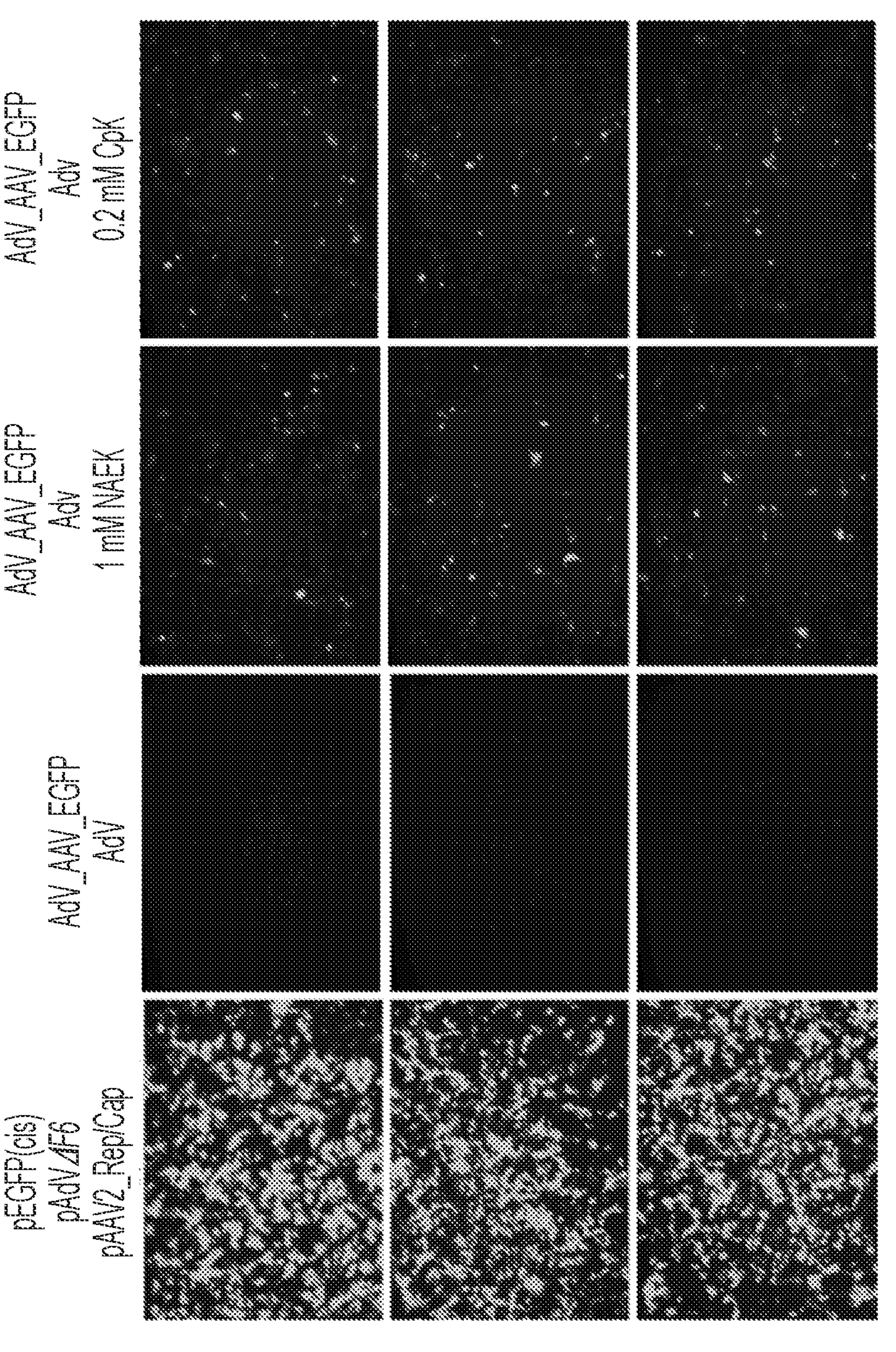

Further, the ability of different ncAA as an inducer for AAV production was tested. The experimental procedure is shown in FIG. 9A. wild-type HEK293 cells were transfected by a plasmid expressing either wild type or mutant EGFP (Y39X) and a plasmid containing orthogonal Pyrrolysyl-tRNA synthetase/pyltRNA pair. Either NAEK, or CpK was supplemented to the media to a final concentration of 1 mM, and 0.2 mM, respectively, 24 hours post transfection. As shown in FIG. 9B, both NEAK and CpK successfully induced read through of EGFP Y39X mutation and EGFP expression. ncAA as an inducer for AAV production was also tested. HEK cells shown in FIG. 8A were treating with NEAK at 1 mM final concentration, or CpK at 0.2 mM final concentration. Twenty-four hours later, the cells were sequentially infected with Adv5 and hybrid AdV-AAV-EGFP 24 hours apart. Crude lysate was harvested 72 hours post initial infection and heat treated at 56° C. for 30 min. 1/10th of the crude lysate was used to infect new HEK293 cells. As shown in FIG. 9D, the crude lysate from HEK293 cells supplemented with 1 mM NEAK or 0.2 mM CpK successfully infected new HEK293 cells 48 hours post-infection, indicating that NEAK and CpK induced read through of the mutant rep gene, thereby leading to successful rAAV packaging. Other ncAA known in the art or described in this disclosure, such as Boc-lysine, can also be used as read through inducers for AAV production.

Figure 10A:
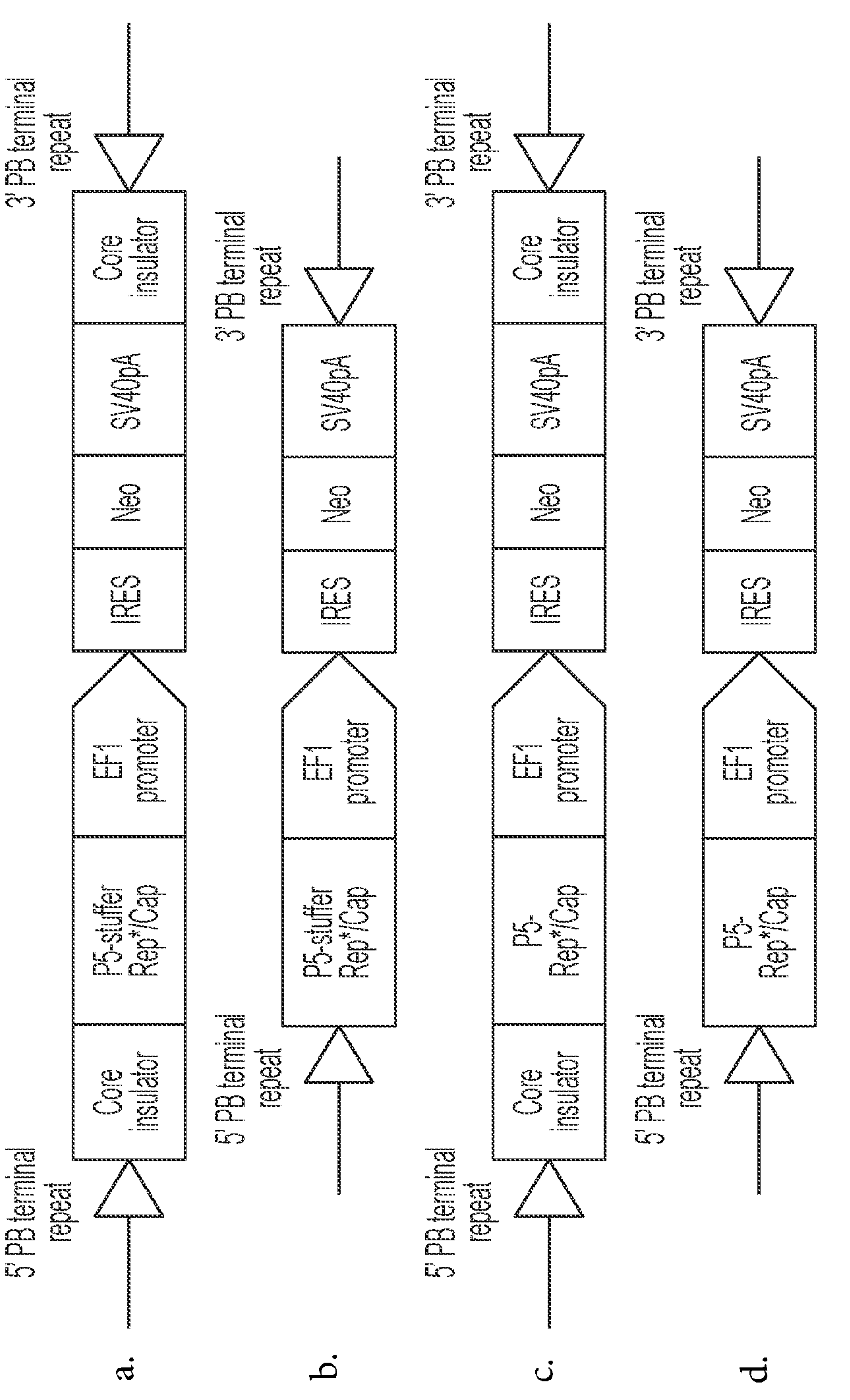
FIGS. 10A-10C are graphs showing testing AAV production using a cell line that contains modified Rep*/cap construct.
Figure 10B:
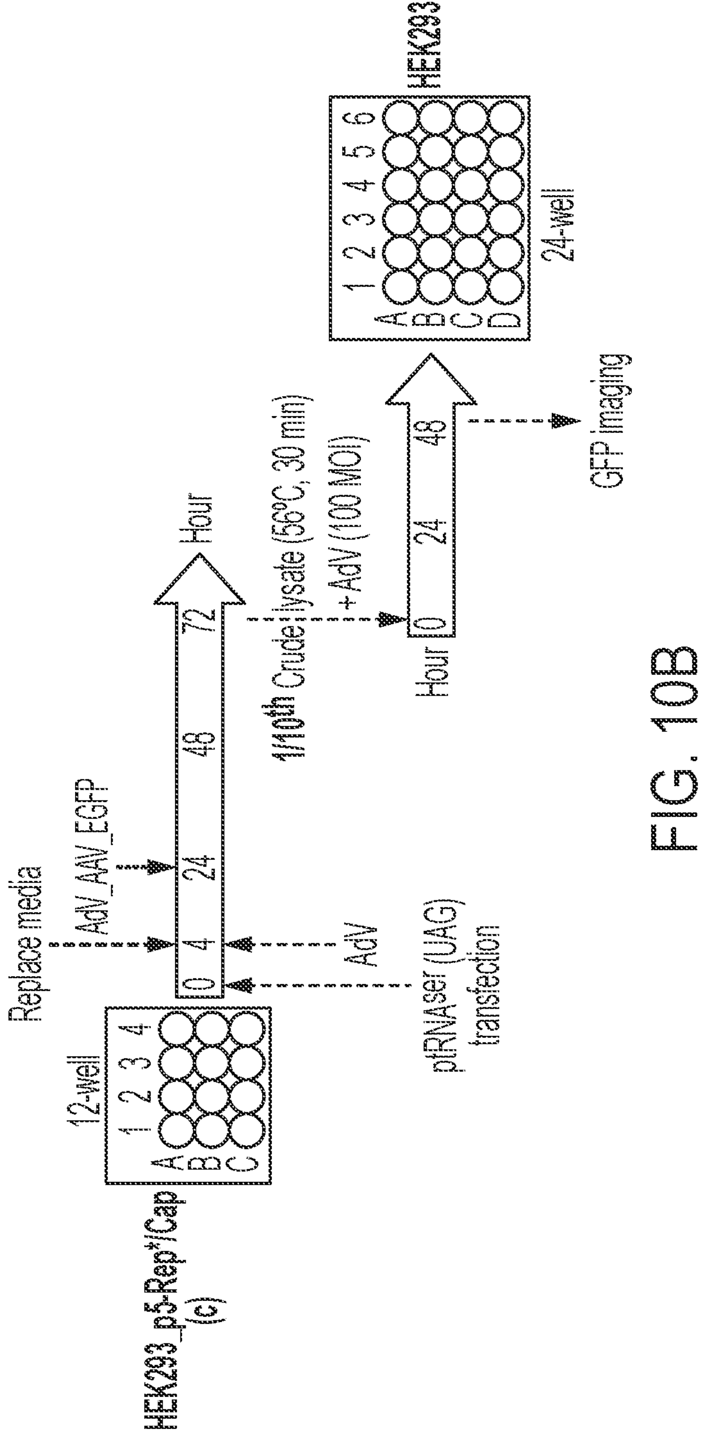
Figure 10C:
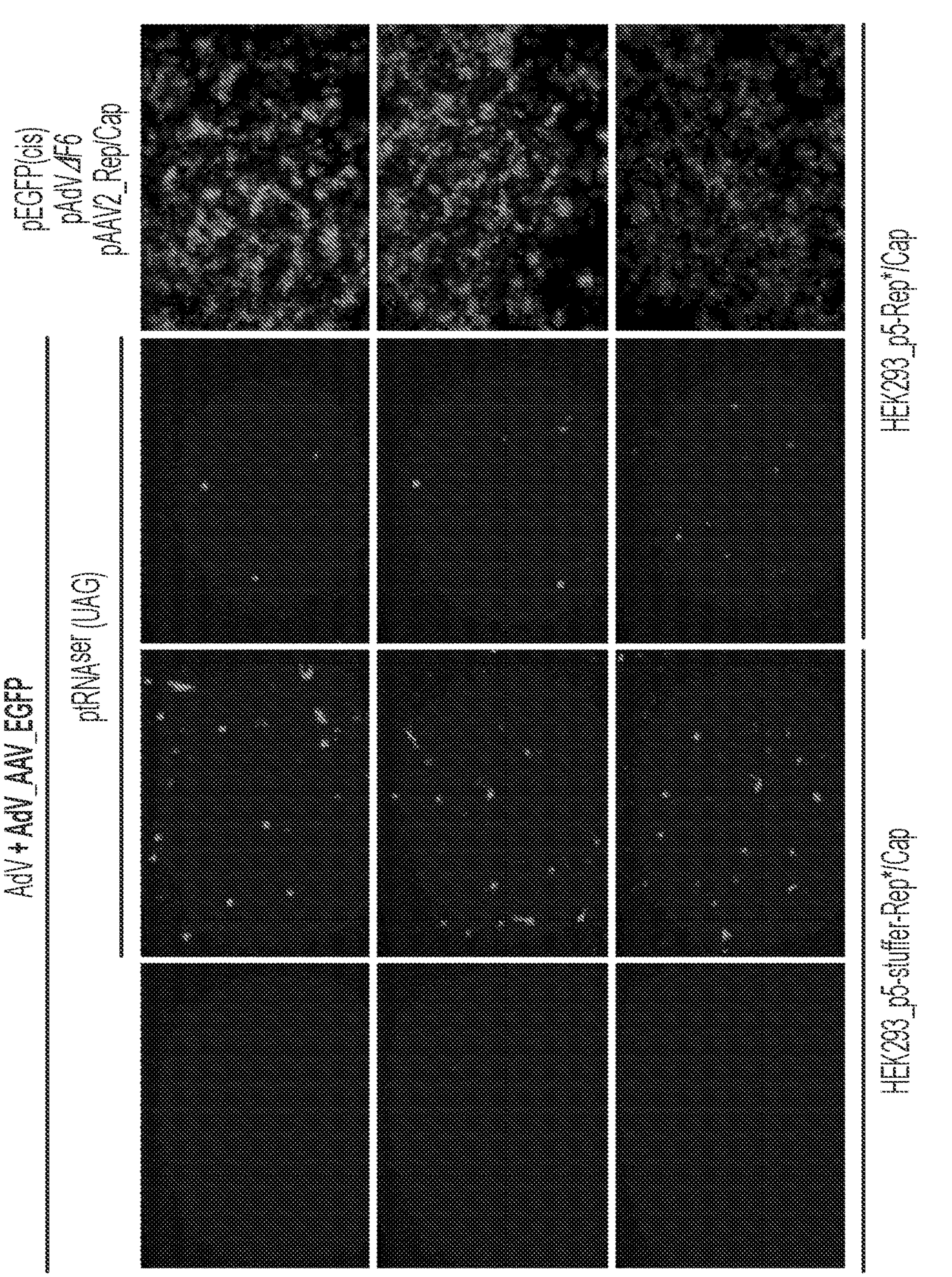

Other HEK293 cell lines harboring mutant rep/cap were generated using different constructs for control of rep/cap expression in the cell line by piggybac transposon system. Four constructs were tested (FIG. 10A). These constructs use a P5 promoter, which is a native promoter for rep/cap gene, in driving the expression of mutant rep/cap gene (Rep*/Cap). A stuffer sequences can be placed between the P5 promoter and the coding sequence of the Rep*/Cap as a regulator of rep/cap protein expression level. Alternatively, a core insulator sequence can be placed to flank the expression cassette. The placement of the core insulators may be able to reduce the unintended expression of the nearby genes where the constructed is inserted in the genome. Construct (a) (SEQ ID NO: 15) and (b) (SEQ ID NO: 16) contain 600 bp stuffer sequence at the p5 promoter but not construct (c) (SEQ ID NO: 17) and (d) (SEQ ID NO: 18). Construct (a) and (c) have the core insulator sequence flanking the expression cassette but not construct (b) and (d). FIG. 10B shows a schematic illustration of experimental procedure in testing these cells for AAV production. Cell lines that carry constructs (a) and (c) were sequentially infected with Adv5 and hybrid AdV-AAV-EGFP, after transfecting the cells with suppressor tRNA (tRNAser(UAG)). Crude lysate was harvested 72 hours post-transfection and heat treated at 56° C. for 30 min. 1/10th of the crude lysate was used to infect new HEK293 cells. FIG. 10C shows that HEK293 cell lines carrying constructs (a) or (c) are capable of rAAV production.

What is claimed is:

1. A nucleic acid encoding an adeno-associated virus (AAV) rep gene that comprises one mutation that prematurely stops the translation of at least one AAV rep protein, wherein the one mutation comprises a C714A mutation relative to SEQ ID NO: 1, and wherein the nucleic acid sequence of the AAV rep gene is at least 90% sequence identity to SEQ ID NO: 1.

2. The nucleic acid of claim 1, wherein the nonsense mutation encodes a UAG codon.

3. The nucleic acid of claim 1, wherein the rep gene that comprises one or more mutations comprises a nucleic acid sequence of any one of SEQ ID NOs: 3, 5, 7, 9, 11 and 13.

* * * * *

SEQUENCE LISTING

```
<160> NUMBER OF SEQ ID NOS: 18

<210> SEQ ID NO 1
<211> LENGTH: 1867
<212> TYPE: DNA
```

<213> ORGANISM: Artificial Sequence
<220> FEATURE:
<223> OTHER INFORMATION: Synthetic polynucleotide

<400> SEQUENCE: 1

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggctct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccagcggg atcgagccga ctttgccaaa ctggttcgcg gtcacaaaga ccagaaatgg    420
cgccggaggc gggaacaagg tggtggatga gtgctacatc cccaattact tgctccccaa    480
aacccagcct gagctccagt gggcgtggac taatatggaa cagtatttaa gcgcctgttt    540
gaatctcacg gagcgtaaac ggttggtggc gcagcatctg acgcacgtgt cgcagacgca    600
ggagcagaac aaagagaatc agaatcccaa ttctgatgcg ccggtgatca gatcaaaaac    660
ttcagccagg tacatggagc tggtcgggtg gctcgtggac aaggggatta cctcggagaa    720
gcagtggatc caggaggacc aggcctcata catctccttc aatgcggcct ccaactcgcg    780
gtcccaaatc aaggctgcct tggacaatgc gggaaagatt atgagcctga ctaaaaccgc    840
cccgactac ctggtgggcc agcagcccgt ggaggacatt tccagcaatc ggatttataa     900
aattttggaa ctaaacgggt acgatcccca atatgcggct tccgtctttc tgggatgggc    960
cacgaaaaag ttcggcaaga ggaacaccat ctggctgttt gggcctgcaa ctaccgggaa   1020
gaccaacatc gcggaggcca tagcccacac tgtgcccttc tacgggtgcg taaactggac   1080
caatgagaac tttcccttca acgactgtgt cgacaagatg gtgatctggt gggaggaggg   1140
gaagatgacc gccaaggtcg tggagtcggc caaagccatt ctcggaggaa gcaaggtgcg   1200
cgtggaccag aaatgcaagt cctcggccca gatagacccg actcccgtga tcgtcacctc   1260
caacaccaac atgtgcgccg tgattgacgg gaactcaacg accttcgaac accagcagcc   1320
gttgcaagac cggatgttca aatttgaact cacccgccgt ctggatcatg actttgggaa   1380
ggtcaccaag caggaagtca aagacttttt ccggtgggca aaggatcacg tggttgaggt   1440
ggagcatgaa ttctacgtca aaaagggtgg agccaagaaa agacccgccc ccagtgacgc   1500
agatataagt gagcccaaac gggtgcgcga gtcagttgcg cagccatcga cgtcagacgc   1560
ggaagcttcg atcaactacg cagacaggta ccaaaacaaa tgttctcgtc acgtgggcat   1620
gaatctgatg ctgtttccct gcagacaatg cgagagaatg aatcagaatt caaatatctg   1680
cttcactcac ggacagaaag actgtttaga gtgctttccc gtgtcagaat ctcaacccgt   1740
ttctgtcgtc aaaaaggcgt atcagaaact gtgctacatt catcatatca tgggaaaggt   1800
gccagacgct tgcactgcct gcgatctggt caatgtggat ttggatgact gcatctttga   1860
acaataa                                                             1867
```

<210> SEQ ID NO 2
<211> LENGTH: 621
<212> TYPE: PRT
<213> ORGANISM: Artificial Sequence
<220> FEATURE:
<223> OTHER INFORMATION: Synthetic polypeptide

<400> SEQUENCE: 2

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415
```

```
Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620
```

<210> SEQ ID NO 3
<211> LENGTH: 1867
<212> TYPE: DNA
<213> ORGANISM: Artificial Sequence
<220> FEATURE:
<223> OTHER INFORMATION: Synthetic polynucleotide

<400> SEQUENCE: 3

```
atgccggggt tttacgagat tgtgattaag gtccccagcg accttgacga gcatctgccc      60

ggcatttctg acagctttgt gaactgggtg gccgagaagg aatgggagtt gccgccagat     120

tctgacatgg atctgaatct gattgagcag gcacccctga ccgtggccga gaagctgcag     180

cgcgactttc tgacggaatg gcgccgtgtg agtaaggccc cggaggctct tttctttgtg     240

caatttgaga agggagagag ctacttccac atgcacgtgc tcgtggaaac caccggggtg     300

aaatccatgg ttttgggacg tttcctgagt cagattcgcg aaaaactgat tcagagaatt     360

taccagcggg atcgagccga ctttgccaaa ctggttcgcg gtcacaaaga ccagaaatgg     420

cgccggaggc gggaacaagg tggtggatga gtgctacatc cccaattact tgctccccaa     480

aacccagcct gagctccagt gggcgtggac taatatggaa cagtatttaa gcgcctgttt     540

gaatctcacg gagcgtaaac ggttggtggc gcagcatctg acgcacgtgt cgcagacgca     600

ggagcagaac aaagagaatc agaatcccaa ttctgatgcg ccggtgatca gatcaaaaac     660

ttcagccagg tacatggagc tggtcgggtg gctcgtggac aaggggatta cctaggagaa     720

gcagtggatc caggaggacc aggcctcata catctccttc aatgcggcct ccaactcgcg     780

gtcccaaatc aaggctgcct tggacaatgc gggaaagatt atgagcctga ctaaaaccgc     840

ccccgactac ctggtgggcc agcagcccgt ggaggacatt tccagcaatc ggatttataa     900
```

```
aattttggaa ctaaacgggt acgatcccca atatgcggct tccgtctttc tgggatgggc    960

cacgaaaaag ttcggcaaga ggaacaccat ctggctgttt gggcctgcaa ctaccgggaa   1020

gaccaacatc gcggaggcca tagcccacac tgtgcccttc tacgggtgcg taaactggac   1080

caatgagaac tttcccttca acgactgtgt cgacaagatg gtgatctggt gggaggaggg   1140

gaagatgacc gccaaggtcg tggagtcggc caaagccatt ctcggaggaa gcaaggtgcg   1200

cgtggaccag aaatgcaagt cctcggccca gatagacccg actcccgtga tcgtcacctc   1260

caacaccaac atgtgcgccg tgattgacgg gaactcaacg accttcgaac accagcagcc   1320

gttgcaagac cggatgttca aatttgaact cacccgccgt ctggatcatg actttgggaa   1380

ggtcaccaag caggaagtca aagacttttt ccggtgggca aaggatcacg tggttgaggt   1440

ggagcatgaa ttctacgtca aaaagggtgg agccaagaaa agacccgccc ccagtgacgc   1500

agatataagt gagcccaaac gggtgcgcga gtcagttgcg cagccatcga cgtcagacgc   1560

ggaagcttcg atcaactacg cagacaggta ccaaaacaaa tgttctcgtc acgtgggcat   1620

gaatctgatg ctgtttccct gcagacaatg cgagagaatg aatcagaatt caaatatctg   1680

cttcactcac ggacagaaag actgtttaga gtgctttccc gtgtcagaat ctcaacccgt   1740

ttctgtcgtc aaaaaggcgt atcagaaact gtgctacatt catcatatca tgggaaaggt   1800

gccagacgct tgcactgcct gcgatctggt caatgtggat ttggatgact gcatctttga   1860

acaataa                                                             1867
```

<210> SEQ ID NO 4
<211> LENGTH: 620
<212> TYPE: PRT
<213> ORGANISM: Artificial Sequence
<220> FEATURE:
<223> OTHER INFORMATION: Synthetic polypeptide

<400> SEQUENCE: 4

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190
```

```
Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Glu Lys Gln
225                 230                 235                 240

Trp Ile Gln Glu Asp Gln Ala Ser Tyr Ile Ser Phe Asn Ala Ala Ser
                245                 250                 255

Asn Ser Arg Ser Gln Ile Lys Ala Ala Leu Asp Asn Ala Gly Lys Ile
            260                 265                 270

Met Ser Leu Thr Lys Thr Ala Pro Asp Tyr Leu Val Gly Gln Gln Pro
        275                 280                 285

Val Glu Asp Ile Ser Ser Asn Arg Ile Tyr Lys Ile Leu Glu Leu Asn
    290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
                325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
        355                 360                 365

Val Asp Lys Met Val Ile Trp Trp Glu Glu Gly Lys Met Thr Ala Lys
    370                 375                 380

Val Val Glu Ser Ala Lys Ala Ile Leu Gly Gly Ser Lys Val Arg Val
385                 390                 395                 400

Asp Gln Lys Cys Lys Ser Ser Ala Gln Ile Asp Pro Thr Pro Val Ile
                405                 410                 415

Val Thr Ser Asn Thr Asn Met Cys Ala Val Ile Asp Gly Asn Ser Thr
            420                 425                 430

Thr Phe Glu His Gln Gln Pro Leu Gln Asp Arg Met Phe Lys Phe Glu
        435                 440                 445

Leu Thr Arg Arg Leu Asp His Asp Phe Gly Lys Val Thr Lys Gln Glu
    450                 455                 460

Val Lys Asp Phe Phe Arg Trp Ala Lys Asp His Val Val Glu Val Glu
465                 470                 475                 480

His Glu Phe Tyr Val Lys Lys Gly Gly Ala Lys Lys Arg Pro Ala Pro
                485                 490                 495

Ser Asp Ala Asp Ile Ser Glu Pro Lys Arg Val Arg Glu Ser Val Ala
            500                 505                 510

Gln Pro Ser Thr Ser Asp Ala Glu Ala Ser Ile Asn Tyr Ala Asp Arg
        515                 520                 525

Tyr Gln Asn Lys Cys Ser Arg His Val Gly Met Asn Leu Met Leu Phe
    530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
                565                 570                 575

Gln Pro Val Ser Val Val Lys Lys Ala Tyr Gln Lys Leu Cys Tyr Ile
            580                 585                 590

His His Ile Met Gly Lys Val Pro Asp Ala Cys Thr Ala Cys Asp Leu
        595                 600                 605
```

```
Val Asn Val Asp Leu Asp Asp Cys Ile Phe Glu Gln
    610                 615                 620


<210> SEQ ID NO 5
<211> LENGTH: 1867
<212> TYPE: DNA
<213> ORGANISM: Artificial Sequence
<220> FEATURE:
<223> OTHER INFORMATION: Synthetic polynucleotide

<400> SEQUENCE: 5

atgccggggt tttacgagat tgtgattaag gtcccctagg accttgacga gcatctgccc      60

ggcatttctg acagctttgt gaactgggtg gccgagaagg aatgggagtt gccgccagat     120

tctgacatgg atctgaatct gattgagcag gcacccctga ccgtggccga gaagctgcag     180

cgcgactttc tgacggaatg gcgccgtgtg agtaaggccc cggaggctct tttctttgtg     240

caatttgaga agggagagag ctacttccac atgcacgtgc tcgtggaaac caccggggtg     300

aaatccatgg ttttgggacg tttcctgagt cagattcgcg aaaaactgat tcagagaatt     360

taccagcggg atcgagccga ctttgccaaa ctggttcgcg gtcacaaaga ccagaaatgg     420

cgccggaggc gggaacaagg tggtggatga gtgctacatc cccaattact tgctccccaa     480

aacccagcct gagctccagt gggcgtggac taatatggaa cagtatttaa gcgcctgttt     540

gaatctcacg gagcgtaaac ggttggtggc gcagcatctg acgcacgtgt cgcagacgca     600

ggagcagaac aaagagaatc agaatcccaa ttctgatgcg ccggtgatca gatcaaaaac     660

ttcagccagg tacatggagc tggtcgggtg gctcgtggac aaggggatta cctaggagaa     720

gcagtggatc caggaggacc aggcctcata catctccttc aatgcggcct ccaactcgcg     780

gtcccaaatc aaggctgcct tggacaatgc gggaaagatt atgagcctga ctaaaaccgc     840

ccccgactac ctggtgggcc agcagcccgt ggaggacatt tccagcaatc ggatttataa     900

aattttggaa ctaaacgggt acgatcccca atatgcggct tccgtctttc tgggatgggc     960

cacgaaaaag ttcggcaaga ggaacaccat ctggctgttt gggcctgcaa ctaccgggaa    1020

gaccaacatc gcggaggcca tagcccacac tgtgcccttc tacgggtgcg taaactggac    1080

caatgagaac tttcccttca acgactgtgt cgacaagatg gtgatctggt gggaggaggg    1140

gaagatgacc gccaaggtcg tggagtcggc caaagccatt ctcggaggaa gcaaggtgcg    1200

cgtggaccag aaatgcaagt cctcggccca gatagacccg actcccgtga tcgtcacctc    1260

caacaccaac atgtgcgccg tgattgacgg gaactcaacg accttcgaac accagcagcc    1320

gttgcaagac cggatgttca aatttgaact cacccgccgt ctggatcatg actttgggaa    1380

ggtcaccaag caggaagtca aagacttttt ccggtgggca aaggatcacg tggttgaggt    1440

ggagcatgaa ttctacgtca aaaagggtgg agccaagaaa agacccgccc ccagtgacgc    1500

agatataagt gagcccaaac gggtgcgcga gtcagttgcg cagccatcga cgtcagacgc    1560

ggaagcttcg atcaactacg cagacaggta ccaaaacaaa tgttctcgtc acgtgggcat    1620

gaatctgatg ctgtttccct gcagacaatg cgagagaatg aatcagaatt caaatatctg    1680

cttcactcac ggacagaaag actgtttaga gtgctttccc gtgtcagaat ctcaacccgt    1740

ttctgtcgtc aaaaaggcgt atcagaaact gtgctacatt catcatatca tgggaaaggt    1800

gccagacgct tgcactgcct gcgatctggt caatgtggat ttggatgact gcatctttga    1860

acaataa                                                              1867


<210> SEQ ID NO 6
```

```
<211> LENGTH: 619
<212> TYPE: PRT
<213> ORGANISM: Artificial Sequence
<220> FEATURE:
<223> OTHER INFORMATION: Synthetic polypeptide

<400> SEQUENCE: 6

Met Pro Gly Phe Tyr Glu Ile Val Ile Lys Val Pro Asp Leu Asp Glu
1               5                   10                  15

His Leu Pro Gly Ile Ser Asp Ser Phe Val Asn Trp Val Ala Glu Lys
            20                  25                  30

Glu Trp Glu Leu Pro Pro Asp Ser Asp Met Asp Leu Asn Leu Ile Glu
        35                  40                  45

Gln Ala Pro Leu Thr Val Ala Glu Lys Leu Gln Arg Asp Phe Leu Thr
    50                  55                  60

Glu Trp Arg Arg Val Ser Lys Ala Pro Glu Ala Leu Phe Phe Val Gln
65                  70                  75                  80

Phe Glu Lys Gly Glu Ser Tyr Phe His Met His Val Leu Val Glu Thr
                85                  90                  95

Thr Gly Val Lys Ser Met Val Leu Gly Arg Phe Leu Ser Gln Ile Arg
            100                 105                 110

Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Gly Asn
    130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
            180                 185                 190

Thr His Val Ser Gln Thr Gln Glu Gln Asn Lys Glu Asn Gln Asn Pro
        195                 200                 205

Asn Ser Asp Ala Pro Val Ile Arg Ser Lys Thr Ser Ala Arg Tyr Met
    210                 215                 220

Glu Leu Val Gly Trp Leu Val Asp Lys Gly Ile Thr Glu Lys Gln Trp
225                 230                 235                 240

Ile Gln Glu Asp Gln Ala Ser Tyr Ile Ser Phe Asn Ala Ala Ser Asn
                245                 250                 255

Ser Arg Ser Gln Ile Lys Ala Ala Leu Asp Asn Ala Gly Lys Ile Met
            260                 265                 270

Ser Leu Thr Lys Thr Ala Pro Asp Tyr Leu Val Gly Gln Gln Pro Val
        275                 280                 285

Glu Asp Ile Ser Ser Asn Arg Ile Tyr Lys Ile Leu Glu Leu Asn Gly
    290                 295                 300

Tyr Asp Pro Gln Tyr Ala Ala Ser Val Phe Leu Gly Trp Ala Thr Lys
305                 310                 315                 320

Lys Phe Gly Lys Arg Asn Thr Ile Trp Leu Phe Gly Pro Ala Thr Thr
                325                 330                 335

Gly Lys Thr Asn Ile Ala Glu Ala Ile Ala His Thr Val Pro Phe Tyr
            340                 345                 350

Gly Cys Val Asn Trp Thr Asn Glu Asn Phe Pro Phe Asn Asp Cys Val
        355                 360                 365

Asp Lys Met Val Ile Trp Trp Glu Glu Gly Lys Met Thr Ala Lys Val
    370                 375                 380
```

```
Val Glu Ser Ala Lys Ala Ile Leu Gly Gly Ser Lys Val Arg Val Asp
385                 390                 395                 400

Gln Lys Cys Lys Ser Ser Ala Gln Ile Asp Pro Thr Pro Val Ile Val
                405                 410                 415

Thr Ser Asn Thr Asn Met Cys Ala Val Ile Asp Gly Asn Ser Thr Thr
            420                 425                 430

Phe Glu His Gln Gln Pro Leu Gln Asp Arg Met Phe Lys Phe Glu Leu
        435                 440                 445

Thr Arg Arg Leu Asp His Asp Phe Gly Lys Val Thr Lys Gln Glu Val
    450                 455                 460

Lys Asp Phe Phe Arg Trp Ala Lys Asp His Val Val Glu Val Glu His
465                 470                 475                 480

Glu Phe Tyr Val Lys Lys Gly Gly Ala Lys Lys Arg Pro Ala Pro Ser
                485                 490                 495

Asp Ala Asp Ile Ser Glu Pro Lys Arg Val Arg Glu Ser Val Ala Gln
            500                 505                 510

Pro Ser Thr Ser Asp Ala Glu Ala Ser Ile Asn Tyr Ala Asp Arg Tyr
        515                 520                 525

Gln Asn Lys Cys Ser Arg His Val Gly Met Asn Leu Met Leu Phe Pro
    530                 535                 540

Cys Arg Gln Cys Glu Arg Met Asn Gln Asn Ser Asn Ile Cys Phe Thr
545                 550                 555                 560

His Gly Gln Lys Asp Cys Leu Glu Cys Phe Pro Val Ser Glu Ser Gln
                565                 570                 575

Pro Val Ser Val Val Lys Lys Ala Tyr Gln Lys Leu Cys Tyr Ile His
            580                 585                 590

His Ile Met Gly Lys Val Pro Asp Ala Cys Thr Ala Cys Asp Leu Val
        595                 600                 605

Asn Val Asp Leu Asp Asp Cys Ile Phe Glu Gln
    610                 615
```

<210> SEQ ID NO 7
<211> LENGTH: 1867
<212> TYPE: DNA
<213> ORGANISM: Artificial Sequence
<220> FEATURE:
<223> OTHER INFORMATION: Synthetic polynucleotide

<400> SEQUENCE: 7

```
atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggctct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccagcggg atcgagccga ctttgccaaa ctggttcgcg gtcacaaaga ccagaaatgg    420

cgccggaggc gggaacaagg tggtggatga gtgctacatc cccaattact tgctccccaa    480

aacccagcct gagctccagt gggcgtggac taatatggaa cagtatttaa gcgcctgttt    540

gaatctcacg gagcgtaaac ggttggtggc gcagcatctg acgcacgtgt cgcagacgca    600

ggagcagaac aaagagaatc agaatcccaa ttctgatgcg ccggtgatca gatcaaaaac    660

ttcagccagg tacatggagc tggtcgggtg gctcgtggac aaggggatta cctcggagta    720
```

```
gcagtggatc caggaggacc aggcctcata catctccttc aatgcggcct ccaactcgcg    780

gtcccaaatc aaggctgcct tggacaatgc gggaaagatt atgagcctga ctaaaaccgc    840

ccccgactac ctggtgggcc agcagcccgt ggaggacatt tccagcaatc ggatttataa    900

aattttggaa ctaaacgggt acgatcccca atatgcggct tccgtctttc tgggatgggc    960

cacgaaaaag ttcggcaaga ggaacaccat ctggctgttt gggcctgcaa ctaccgggaa   1020

gaccaacatc gcggaggcca tagcccacac tgtgcccttc tacgggtgcg taaactggac   1080

caatgagaac tttcccttca acgactgtgt cgacaagatg gtgatctggt gggaggaggg   1140

gaagatgacc gccaaggtcg tggagtcggc caaagccatt ctcggaggaa gcaaggtgcg   1200

cgtggaccag aaatgcaagt cctcggccca gatagacccg actcccgtga tcgtcacctc   1260

caacaccaac atgtgcgccg tgattgacgg gaactcaacg accttcgaac accagcagcc   1320

gttgcaagac cggatgttca aatttgaact cacccgccgt ctggatcatg actttgggaa   1380

ggtcaccaag caggaagtca aagacttttt ccggtgggca aaggatcacg tggttgaggt   1440

ggagcatgaa ttctacgtca aaaagggtgg agccaagaaa agacccgccc ccagtgacgc   1500

agatataagt gagcccaaac gggtgcgcga gtcagttgcg cagccatcga cgtcagacgc   1560

ggaagcttcg atcaactacg cagacaggta ccaaaacaaa tgttctcgtc acgtgggcat   1620

gaatctgatg ctgtttccct gcagacaatg cgagagaatg aatcagaatt caaatatctg   1680

cttcactcac ggacagaaag actgtttaga gtgctttccc gtgtcagaat ctcaacccgt   1740

ttctgtcgtc aaaaaggcgt atcagaaact gtgctacatt catcatatca tgggaaaggt   1800

gccagacgct tgcactgcct gcgatctggt caatgtggat ttggatgact gcatctttga   1860

acaataa                                                             1867
```

```
<210> SEQ ID NO 8
<211> LENGTH: 620
<212> TYPE: PRT
<213> ORGANISM: Artificial Sequence
<220> FEATURE:
<223> OTHER INFORMATION: Synthetic polypeptide

<400> SEQUENCE: 8

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
```

```
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Gln
225                 230                 235                 240

Trp Ile Gln Glu Asp Gln Ala Ser Tyr Ile Ser Phe Asn Ala Ala Ser
                245                 250                 255

Asn Ser Arg Ser Gln Ile Lys Ala Ala Leu Asp Asn Ala Gly Lys Ile
            260                 265                 270

Met Ser Leu Thr Lys Thr Ala Pro Asp Tyr Leu Val Gly Gln Gln Pro
        275                 280                 285

Val Glu Asp Ile Ser Ser Asn Arg Ile Tyr Lys Ile Leu Glu Leu Asn
    290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
                325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
        355                 360                 365

Val Asp Lys Met Val Ile Trp Trp Glu Glu Gly Lys Met Thr Ala Lys
    370                 375                 380

Val Val Glu Ser Ala Lys Ala Ile Leu Gly Gly Ser Lys Val Arg Val
385                 390                 395                 400

Asp Gln Lys Cys Lys Ser Ser Ala Gln Ile Asp Pro Thr Pro Val Ile
                405                 410                 415

Val Thr Ser Asn Thr Asn Met Cys Ala Val Ile Asp Gly Asn Ser Thr
            420                 425                 430

Thr Phe Glu His Gln Gln Pro Leu Gln Asp Arg Met Phe Lys Phe Glu
        435                 440                 445

Leu Thr Arg Arg Leu Asp His Asp Phe Gly Lys Val Thr Lys Gln Glu
    450                 455                 460

Val Lys Asp Phe Phe Arg Trp Ala Lys Asp His Val Val Glu Val Glu
465                 470                 475                 480

His Glu Phe Tyr Val Lys Lys Gly Gly Ala Lys Lys Arg Pro Ala Pro
                485                 490                 495

Ser Asp Ala Asp Ile Ser Glu Pro Lys Arg Val Arg Glu Ser Val Ala
            500                 505                 510

Gln Pro Ser Thr Ser Asp Ala Glu Ala Ser Ile Asn Tyr Ala Asp Arg
        515                 520                 525

Tyr Gln Asn Lys Cys Ser Arg His Val Gly Met Asn Leu Met Leu Phe
    530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
                565                 570                 575
```

```
Gln Pro Val Ser Val Val Lys Lys Ala Tyr Gln Lys Leu Cys Tyr Ile
            580                 585                 590

His His Ile Met Gly Lys Val Pro Asp Ala Cys Thr Ala Cys Asp Leu
        595                 600                 605

Val Asn Val Asp Leu Asp Asp Cys Ile Phe Glu Gln
    610                 615                 620
```

<210> SEQ ID NO 9
<211> LENGTH: 1867
<212> TYPE: DNA
<213> ORGANISM: Artificial Sequence
<220> FEATURE:
<223> OTHER INFORMATION: Synthetic polynucleotide

<400> SEQUENCE: 9

```
atgccggggt tttacgagat tgtgatttag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggctct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccagcggg atcgagccga ctttgccaaa ctggttcgcg gtcacaaaga ccagaaatgg    420

cgccggaggc gggaacaagg tggtggatga gtgctacatc cccaattact tgctccccaa    480

aacccagcct gagctccagt gggcgtggac taatatggaa cagtatttaa gcgcctgttt    540

gaatctcacg gagcgtaaac ggttggtggc gcagcatctg acgcacgtgt cgcagacgca    600

ggagcagaac aaagagaatc agaatcccaa ttctgatgcg ccggtgatca gatcaaaaac    660

ttcagccagg tacatggagc tggtcgggtg gctcgtggac aaggggatta cctcggagta    720

gcagtggatc caggaggacc aggcctcata catctccttc aatgcggcct ccaactcgcg    780

gtcccaaatc aaggctgcct tggacaatgc gggaaagatt atgagcctga ctaaaaccgc    840

cccgactac ctggtgggcc agcagcccgt ggaggacatt tccagcaatc ggatttataa     900

aattttggaa ctaaacgggt acgatcccca atatgcggct tccgtctttc tgggatgggc    960

cacgaaaaag ttcggcaaga ggaacaccat ctggctgttt gggcctgcaa ctaccgggaa   1020

gaccaacatc gcggaggcca tagcccacac tgtgcccttc tacgggtgcg taaactggac   1080

caatgagaac tttcccttca acgactgtgt cgacaagatg gtgatctggt gggaggaggg   1140

gaagatgacc gccaaggtcg tggagtcggc caaagccatt ctcggaggaa gcaaggtgcg   1200

cgtggaccag aaatgcaagt cctcggccca gatagacccg actcccgtga tcgtcacctc   1260

caacaccaac atgtgcgccg tgattgacgg gaactcaacg accttcgaac accagcagcc   1320

gttgcaagac cggatgttca aatttgaact cacccgccgt ctggatcatg actttgggaa   1380

ggtcaccaag caggaagtca aagacttttt ccggtgggca aaggatcacg tggttgaggt   1440

ggagcatgaa ttctacgtca aaaagggtgg agccaagaaa agacccgccc ccagtgacgc   1500

agatataagt gagcccaaac gggtgcgcga gtcagttgcg cagccatcga cgtcagacgc   1560

ggaagcttcg atcaactacg cagacaggta ccaaaacaaa tgttctcgtc acgtgggcat   1620

gaatctgatg ctgtttccct gcagacaatg cgagagaatg aatcagaatt caaatatctg   1680

cttcactcac ggacagaaag actgtttaga gtgctttccc gtgtcagaat ctcaacccgt   1740

ttctgtcgtc aaaaaggcgt atcagaaact gtgctacatt catcatatca tgggaaaggt   1800
```

gccagacgct tgcactgcct gcgatctggt caatgtggat ttggatgact gcatctttga 1860
acaataa 1867

<210> SEQ ID NO 10
<211> LENGTH: 619
<212> TYPE: PRT
<213> ORGANISM: Artificial Sequence
<220> FEATURE:
<223> OTHER INFORMATION: Synthetic polypeptide

<400> SEQUENCE: 10

Met Pro Gly Phe Tyr Glu Ile Val Ile Val Pro Ser Asp Leu Asp Glu
1 5 10 15

His Leu Pro Gly Ile Ser Asp Ser Phe Val Asn Trp Val Ala Glu Lys
20 25 30

Glu Trp Glu Leu Pro Pro Asp Ser Asp Met Asp Leu Asn Leu Ile Glu
35 40 45

Gln Ala Pro Leu Thr Val Ala Glu Lys Leu Gln Arg Asp Phe Leu Thr
50 55 60

Glu Trp Arg Arg Val Ser Lys Ala Pro Glu Ala Leu Phe Phe Val Gln
65 70 75 80

Phe Glu Lys Gly Glu Ser Tyr Phe His Met His Val Leu Val Glu Thr
85 90 95

Thr Gly Val Lys Ser Met Val Leu Gly Arg Phe Leu Ser Gln Ile Arg
100 105 110

Glu Lys Leu Ile Gln Arg Ile Tyr Arg Gly Ile Glu Pro Thr Leu Pro
115 120 125

Asn Trp Phe Ala Val Thr Lys Thr Arg Asn Gly Ala Gly Gly Gly Asn
130 135 140

Lys Val Val Asp Glu Cys Tyr Ile Pro Asn Tyr Leu Leu Pro Lys Thr
145 150 155 160

Gln Pro Glu Leu Gln Trp Ala Trp Thr Asn Met Glu Gln Tyr Leu Ser
165 170 175

Ala Cys Leu Asn Leu Thr Glu Arg Lys Arg Leu Val Ala Gln His Leu
180 185 190

Thr His Val Ser Gln Thr Gln Glu Gln Asn Lys Glu Asn Gln Asn Pro
195 200 205

Asn Ser Asp Ala Pro Val Ile Arg Ser Lys Thr Ser Ala Arg Tyr Met
210 215 220

Glu Leu Val Gly Trp Leu Val Asp Lys Gly Ile Thr Ser Glu Gln Trp
225 230 235 240

Ile Gln Glu Asp Gln Ala Ser Tyr Ile Ser Phe Asn Ala Ala Ser Asn
245 250 255

Ser Arg Ser Gln Ile Lys Ala Ala Leu Asp Asn Ala Gly Lys Ile Met
260 265 270

Ser Leu Thr Lys Thr Ala Pro Asp Tyr Leu Val Gly Gln Gln Pro Val
275 280 285

Glu Asp Ile Ser Ser Asn Arg Ile Tyr Lys Ile Leu Glu Leu Asn Gly
290 295 300

Tyr Asp Pro Gln Tyr Ala Ala Ser Val Phe Leu Gly Trp Ala Thr Lys
305 310 315 320

Lys Phe Gly Lys Arg Asn Thr Ile Trp Leu Phe Gly Pro Ala Thr Thr
325 330 335

Gly Lys Thr Asn Ile Ala Glu Ala Ile Ala His Thr Val Pro Phe Tyr

```
            340                 345                 350

Gly Cys Val Asn Trp Thr Asn Glu Asn Phe Pro Phe Asn Asp Cys Val
        355                 360                 365

Asp Lys Met Val Ile Trp Trp Glu Glu Gly Lys Met Thr Ala Lys Val
    370                 375                 380

Val Glu Ser Ala Lys Ala Ile Leu Gly Gly Ser Lys Val Arg Val Asp
385                 390                 395                 400

Gln Lys Cys Lys Ser Ser Ala Gln Ile Asp Pro Thr Pro Val Ile Val
                405                 410                 415

Thr Ser Asn Thr Asn Met Cys Ala Val Ile Asp Gly Asn Ser Thr Thr
            420                 425                 430

Phe Glu His Gln Gln Pro Leu Gln Asp Arg Met Phe Lys Phe Glu Leu
        435                 440                 445

Thr Arg Arg Leu Asp His Asp Phe Gly Lys Val Thr Lys Gln Glu Val
    450                 455                 460

Lys Asp Phe Phe Arg Trp Ala Lys Asp His Val Val Glu Val Glu His
465                 470                 475                 480

Glu Phe Tyr Val Lys Lys Gly Gly Ala Lys Lys Arg Pro Ala Pro Ser
                485                 490                 495

Asp Ala Asp Ile Ser Glu Pro Lys Arg Val Arg Glu Ser Val Ala Gln
            500                 505                 510

Pro Ser Thr Ser Asp Ala Glu Ala Ser Ile Asn Tyr Ala Asp Arg Tyr
        515                 520                 525

Gln Asn Lys Cys Ser Arg His Val Gly Met Asn Leu Met Leu Phe Pro
    530                 535                 540

Cys Arg Gln Cys Glu Arg Met Asn Gln Asn Ser Asn Ile Cys Phe Thr
545                 550                 555                 560

His Gly Gln Lys Asp Cys Leu Glu Cys Phe Pro Val Ser Glu Ser Gln
                565                 570                 575

Pro Val Ser Val Val Lys Lys Ala Tyr Gln Lys Leu Cys Tyr Ile His
            580                 585                 590

His Ile Met Gly Lys Val Pro Asp Ala Cys Thr Ala Cys Asp Leu Val
        595                 600                 605

Asn Val Asp Leu Asp Asp Cys Ile Phe Glu Gln
    610                 615
```

<210> SEQ ID NO 11
<211> LENGTH: 1867
<212> TYPE: DNA
<213> ORGANISM: Artificial Sequence
<220> FEATURE:
<223> OTHER INFORMATION: Synthetic polynucleotide

<400> SEQUENCE: 11

```
atgccggggt tttacgagat tgtgattaag gtcccctagg accttgacga gcatctgccc      60

ggcatttctg acagctttgt gaactgggtg gccgagaagg aatgggagtt gccgccagat     120

tctgacatgg atctgaatct gattgagcag gcacccctga ccgtggccga gaagctgcag     180

cgcgactttc tgacggaatg gcgccgtgtg agtaaggccc cggaggctct tttctttgtg     240

caatttgaga agggagagag ctacttccac atgcacgtgc tcgtggaaac caccggggtg     300

aaatccatgg ttttgggacg tttcctgagt cagattcgcg aaaaactgat tcagagaatt     360

taccagcggg atcgagccga ctttgccaaa ctggttcgcg gtcacaaaga ccagaaatgg     420

cgccggaggc gggaacaagg tggtggatga gtgctacatc cccaattact tgctccccaa     480
```

```
aacccagcct gagctccagt gggcgtggac taatatggaa cagtatttaa gcgcctgttt    540

gaatctcacg gagcgtaaac ggttggtggc gcagcatctg acgcacgtgt cgcagacgca    600

ggagcagaac aaagagaatc agaatcccaa ttctgatgcg ccggtgatca gatcaaaaac    660

ttcagccagg tacatggagc tggtcgggtg gctcgtggac aaggggatta cctcggagta    720

gcagtggatc caggaggacc aggcctcata catctccttc aatgcggcct ccaactcgcg    780

gtcccaaatc aaggctgcct tggacaatgc gggaaagatt atgagcctga ctaaaaccgc    840

ccccgactac ctggtgggcc agcagcccgt ggaggacatt tccagcaatc ggatttataa    900

aattttggaa ctaaacgggt acgatcccca atatgcggct tccgtctttc tgggatgggc    960

cacgaaaaag ttcggcaaga ggaacaccat ctggctgttt gggcctgcaa ctaccgggaa   1020

gaccaacatc gcggaggcca tagcccacac tgtgcccttc tacgggtgcg taaactggac   1080

caatgagaac tttcccttca acgactgtgt cgacaagatg gtgatctggt gggaggaggg   1140

gaagatgacc gccaaggtcg tggagtcggc caaagccatt ctcggaggaa gcaaggtgcg   1200

cgtggaccag aaatgcaagt cctcggccca gatagacccg actcccgtga tcgtcacctc   1260

caacaccaac atgtgcgccg tgattgacgg gaactcaacg accttcgaac accagcagcc   1320

gttgcaagac cggatgttca aatttgaact cacccgccgt ctggatcatg actttgggaa   1380

ggtcaccaag caggaagtca aagacttttt ccggtgggca aaggatcacg tggttgaggt   1440

ggagcatgaa ttctacgtca aaaagggtgg agccaagaaa agacccgccc ccagtgacgc   1500

agatataagt gagcccaaac gggtgcgcga gtcagttgcg cagccatcga cgtcagacgc   1560

ggaagcttcg atcaactacg cagacaggta ccaaaacaaa tgttctcgtc acgtgggcat   1620

gaatctgatg ctgtttccct gcagacaatg cgagagaatg aatcagaatt caaatatctg   1680

cttcactcac ggacagaaag actgtttaga gtgctttccc gtgtcagaat ctcaacccgt   1740

ttctgtcgtc aaaaaggcgt atcagaaact gtgctacatt catcatatca tgggaaaggt   1800

gccagacgct tgcactgcct gcgatctggt caatgtggat ttggatgact gcatctttga   1860

acaataa                                                             1867


<210> SEQ ID NO 12
<211> LENGTH: 619
<212> TYPE: PRT
<213> ORGANISM: Artificial Sequence
<220> FEATURE:
<223> OTHER INFORMATION: Synthetic polypeptide

<400> SEQUENCE: 12

Met Pro Gly Phe Tyr Glu Ile Val Ile Lys Val Pro Asp Leu Asp Glu
1               5                   10                  15

His Leu Pro Gly Ile Ser Asp Ser Phe Val Asn Trp Val Ala Glu Lys
            20                  25                  30

Glu Trp Glu Leu Pro Pro Asp Ser Asp Met Asp Leu Asn Leu Ile Glu
        35                  40                  45

Gln Ala Pro Leu Thr Val Ala Glu Lys Leu Gln Arg Asp Phe Leu Thr
    50                  55                  60

Glu Trp Arg Arg Val Ser Lys Ala Pro Glu Ala Leu Phe Phe Val Gln
65                  70                  75                  80

Phe Glu Lys Gly Glu Ser Tyr Phe His Met His Val Leu Val Glu Thr
                85                  90                  95

Thr Gly Val Lys Ser Met Val Leu Gly Arg Phe Leu Ser Gln Ile Arg
            100                 105                 110
```

```
Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Gly Asn
    130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
            180                 185                 190

Thr His Val Ser Gln Thr Gln Glu Gln Asn Lys Glu Asn Gln Asn Pro
        195                 200                 205

Asn Ser Asp Ala Pro Val Ile Arg Ser Lys Thr Ser Ala Arg Tyr Met
    210                 215                 220

Glu Leu Val Gly Trp Leu Val Asp Lys Gly Ile Thr Ser Glu Gln Trp
225                 230                 235                 240

Ile Gln Glu Asp Gln Ala Ser Tyr Ile Ser Phe Asn Ala Ala Ser Asn
                245                 250                 255

Ser Arg Ser Gln Ile Lys Ala Ala Leu Asp Asn Ala Gly Lys Ile Met
            260                 265                 270

Ser Leu Thr Lys Thr Ala Pro Asp Tyr Leu Val Gly Gln Gln Pro Val
        275                 280                 285

Glu Asp Ile Ser Ser Asn Arg Ile Tyr Lys Ile Leu Glu Leu Asn Gly
    290                 295                 300

Tyr Asp Pro Gln Tyr Ala Ala Ser Val Phe Leu Gly Trp Ala Thr Lys
305                 310                 315                 320

Lys Phe Gly Lys Arg Asn Thr Ile Trp Leu Phe Gly Pro Ala Thr Thr
                325                 330                 335

Gly Lys Thr Asn Ile Ala Glu Ala Ile Ala His Thr Val Pro Phe Tyr
            340                 345                 350

Gly Cys Val Asn Trp Thr Asn Glu Asn Phe Pro Phe Asn Asp Cys Val
        355                 360                 365

Asp Lys Met Val Ile Trp Trp Glu Glu Gly Lys Met Thr Ala Lys Val
    370                 375                 380

Val Glu Ser Ala Lys Ala Ile Leu Gly Gly Ser Lys Val Arg Val Asp
385                 390                 395                 400

Gln Lys Cys Lys Ser Ser Ala Gln Ile Asp Pro Thr Pro Val Ile Val
                405                 410                 415

Thr Ser Asn Thr Asn Met Cys Ala Val Ile Asp Gly Asn Ser Thr Thr
            420                 425                 430

Phe Glu His Gln Gln Pro Leu Gln Asp Arg Met Phe Lys Phe Glu Leu
        435                 440                 445

Thr Arg Arg Leu Asp His Asp Phe Gly Lys Val Thr Lys Gln Glu Val
    450                 455                 460

Lys Asp Phe Phe Arg Trp Ala Lys Asp His Val Val Glu Val Glu His
465                 470                 475                 480

Glu Phe Tyr Val Lys Lys Gly Gly Ala Lys Lys Arg Pro Ala Pro Ser
                485                 490                 495

Asp Ala Asp Ile Ser Glu Pro Lys Arg Val Arg Glu Ser Val Ala Gln
            500                 505                 510

Pro Ser Thr Ser Asp Ala Glu Ala Ser Ile Asn Tyr Ala Asp Arg Tyr
        515                 520                 525

Gln Asn Lys Cys Ser Arg His Val Gly Met Asn Leu Met Leu Phe Pro
```

```
    530                 535                 540

Cys Arg Gln Cys Glu Arg Met Asn Gln Asn Ser Asn Ile Cys Phe Thr
545                 550                 555                 560

His Gly Gln Lys Asp Cys Leu Glu Cys Phe Pro Val Ser Glu Ser Gln
                565                 570                 575

Pro Val Ser Val Val Lys Lys Ala Tyr Gln Lys Leu Cys Tyr Ile His
            580                 585                 590

His Ile Met Gly Lys Val Pro Asp Ala Cys Thr Ala Cys Asp Leu Val
        595                 600                 605

Asn Val Asp Leu Asp Asp Cys Ile Phe Glu Gln
    610                 615


<210> SEQ ID NO 13
<211> LENGTH: 1867
<212> TYPE: DNA
<213> ORGANISM: Artificial Sequence
<220> FEATURE:
<223> OTHER INFORMATION: Synthetic polynucleotide

<400> SEQUENCE: 13

atgccggggt tttacgagat tgtgatttag gtccccagcg accttgacga gcatctgccc     60

ggcatttctg acagctttgt gaactgggtg gccgagaagg aatgggagtt gccgccagat    120

tctgacatgg atctgaatct gattgagcag gcaccccctga ccgtggccga gaagctgcag    180

cgcgactttc tgacggaatg gcgccgtgtg agtaaggccc cggaggctct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccagcggg atcgagccga ctttgccaaa ctggttcgcg gtcacaaaga ccagaaatgg    420

cgccggaggc gggaacaagg tggtggatga gtgctacatc cccaattact tgctccccaa    480

aacccagcct gagctccagt gggcgtggac taatatggaa cagtatttaa gcgcctgttt    540

gaatctcacg gagcgtaaac ggttggtggc gcagcatctg acgcacgtgt cgcagacgca    600

ggagcagaac aaagagaatc agaatcccaa ttctgatgcg ccggtgatca gatcaaaaac    660

ttcagccagg tacatggagc tggtcgggtg gctcgtggac aaggggatta cctaggagaa    720

gcagtggatc caggaggacc aggcctcata catctccttc aatgcggcct ccaactcgcg    780

gtcccaaatc aaggctgcct tggacaatgc gggaaagatt atgagcctga ctaaaaccgc    840

cccgactac ctggtgggcc agcagcccgt ggaggacatt tccagcaatc ggatttataa    900

aattttggaa ctaaacgggt acgatcccca atatgcggct tccgtctttc tgggatgggc    960

cacgaaaaag ttcggcaaga ggaacaccat ctggctgttt gggcctgcaa ctaccgggaa   1020

gaccaacatc gcggaggcca tagcccacac tgtgcccttc tacgggtgcg taaactggac   1080

caatgagaac tttcccttca acgactgtgt cgacaagatg gtgatctggt gggaggaggg   1140

gaagatgacc gccaaggtcg tggagtcggc caaagccatt ctcggaggaa gcaaggtgcg   1200

cgtggaccag aaatgcaagt cctcggccca gatagacccg actcccgtga tcgtcacctc   1260

caacaccaac atgtgcgccg tgattgacgg gaactcaacg accttcgaac accagcagcc   1320

gttgcaagac cggatgttca aatttgaact cacccgccgt ctggatcatg actttgggaa   1380

ggtcaccaag caggaagtca aagacttttt ccggtgggca aaggatcacg tggttgaggt   1440

ggagcatgaa ttctacgtca aaaagggtgg agccaagaaa agacccgccc ccagtgacgc   1500

agatataagt gagcccaaac gggtgcgcga gtcagttgcg cagccatcga cgtcagacgc   1560
```

```
ggaagcttcg atcaactacg cagacaggta ccaaaacaaa tgttctcgtc acgtgggcat   1620

gaatctgatg ctgtttccct gcagacaatg cgagagaatg aatcagaatt caaatatctg   1680

cttcactcac ggacagaaag actgtttaga gtgctttccc gtgtcagaat ctcaacccgt   1740

ttctgtcgtc aaaaaggcgt atcagaaact gtgctacatt catcatatca tgggaaaggt   1800

gccagacgct tgcactgcct gcgatctggt caatgtggat ttggatgact gcatctttga   1860

acaataa                                                             1867
```

```
<210> SEQ ID NO 14
<211> LENGTH: 619
<212> TYPE: PRT
<213> ORGANISM: Artificial Sequence
<220> FEATURE:
<223> OTHER INFORMATION: Synthetic polypeptide

<400> SEQUENCE: 14

Met Pro Gly Phe Tyr Glu Ile Val Ile Val Pro Ser Asp Leu Asp Glu
1               5                   10                  15

His Leu Pro Gly Ile Ser Asp Ser Phe Val Asn Trp Val Ala Glu Lys
            20                  25                  30

Glu Trp Glu Leu Pro Pro Asp Ser Asp Met Asp Leu Asn Leu Ile Glu
        35                  40                  45

Gln Ala Pro Leu Thr Val Ala Glu Lys Leu Gln Arg Asp Phe Leu Thr
    50                  55                  60

Glu Trp Arg Arg Val Ser Lys Ala Pro Glu Ala Leu Phe Phe Val Gln
65                  70                  75                  80

Phe Glu Lys Gly Glu Ser Tyr Phe His Met His Val Leu Val Glu Thr
                85                  90                  95

Thr Gly Val Lys Ser Met Val Leu Gly Arg Phe Leu Ser Gln Ile Arg
            100                 105                 110

Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Gly Asn
    130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
            180                 185                 190

Thr His Val Ser Gln Thr Gln Glu Gln Asn Lys Glu Asn Gln Asn Pro
        195                 200                 205

Asn Ser Asp Ala Pro Val Ile Arg Ser Lys Thr Ser Ala Arg Tyr Met
    210                 215                 220

Glu Leu Val Gly Trp Leu Val Asp Lys Gly Ile Thr Glu Lys Gln Trp
225                 230                 235                 240

Ile Gln Glu Asp Gln Ala Ser Tyr Ile Ser Phe Asn Ala Ala Ser Asn
                245                 250                 255

Ser Arg Ser Gln Ile Lys Ala Ala Leu Asp Asn Ala Gly Lys Ile Met
            260                 265                 270

Ser Leu Thr Lys Thr Ala Pro Asp Tyr Leu Val Gly Gln Gln Pro Val
        275                 280                 285

Glu Asp Ile Ser Ser Asn Arg Ile Tyr Lys Ile Leu Glu Leu Asn Gly
    290                 295                 300
```

```
Tyr Asp Pro Gln Tyr Ala Ala Ser Val Phe Leu Gly Trp Ala Thr Lys
305                 310                 315                 320

Lys Phe Gly Lys Arg Asn Thr Ile Trp Leu Phe Gly Pro Ala Thr Thr
                325                 330                 335

Gly Lys Thr Asn Ile Ala Glu Ala Ile Ala His Thr Val Pro Phe Tyr
            340                 345                 350

Gly Cys Val Asn Trp Thr Asn Glu Asn Phe Pro Phe Asn Asp Cys Val
        355                 360                 365

Asp Lys Met Val Ile Trp Trp Glu Glu Gly Lys Met Thr Ala Lys Val
    370                 375                 380

Val Glu Ser Ala Lys Ala Ile Leu Gly Gly Ser Lys Val Arg Val Asp
385                 390                 395                 400

Gln Lys Cys Lys Ser Ser Ala Gln Ile Asp Pro Thr Pro Val Ile Val
                405                 410                 415

Thr Ser Asn Thr Asn Met Cys Ala Val Ile Asp Gly Asn Ser Thr Thr
            420                 425                 430

Phe Glu His Gln Gln Pro Leu Gln Asp Arg Met Phe Lys Phe Glu Leu
        435                 440                 445

Thr Arg Arg Leu Asp His Asp Phe Gly Lys Val Thr Lys Gln Glu Val
    450                 455                 460

Lys Asp Phe Phe Arg Trp Ala Lys Asp His Val Val Glu Val Glu His
465                 470                 475                 480

Glu Phe Tyr Val Lys Lys Gly Gly Ala Lys Lys Arg Pro Ala Pro Ser
                485                 490                 495

Asp Ala Asp Ile Ser Glu Pro Lys Arg Val Arg Glu Ser Val Ala Gln
            500                 505                 510

Pro Ser Thr Ser Asp Ala Glu Ala Ser Ile Asn Tyr Ala Asp Arg Tyr
        515                 520                 525

Gln Asn Lys Cys Ser Arg His Val Gly Met Asn Leu Met Leu Phe Pro
    530                 535                 540

Cys Arg Gln Cys Glu Arg Met Asn Gln Asn Ser Asn Ile Cys Phe Thr
545                 550                 555                 560

His Gly Gln Lys Asp Cys Leu Glu Cys Phe Pro Val Ser Glu Ser Gln
                565                 570                 575

Pro Val Ser Val Val Lys Lys Ala Tyr Gln Lys Leu Cys Tyr Ile His
            580                 585                 590

His Ile Met Gly Lys Val Pro Asp Ala Cys Thr Ala Cys Asp Leu Val
        595                 600                 605

Asn Val Asp Leu Asp Asp Cys Ile Phe Glu Gln
    610                 615
```

<210> SEQ ID NO 15
<211> LENGTH: 8515
<212> TYPE: DNA
<213> ORGANISM: Artificial Sequence
<220> FEATURE:
<223> OTHER INFORMATION: Synthetic polynucleotide

<400> SEQUENCE: 15

```
ccctagaaag ataatcatat tgtgacgtac gttaaagata atcatgtgta aaattgacgc     60

atgtgtttta tcggtctgta tatcgaggtt tatttattaa tttgaataga tattaagttt    120

tattatattt acacttacat actaataata aattcaacaa acaatttatt tatgtttatt    180

tatttattaa aaaaaacaaa aactcaaaat ttcttctata aagtaacaaa acttttatga    240

gggacagccc ccccccaaag cccccaggga tgtaattacg tccctccccc gctagggggc    300
```

```
agcagcgagc cgcccggggc tccgctccgg tccggcgctc cccccgcatc cccgagccgg    360
cagcgtgcgg ggacagcccg ggcacgggga aggtggcacg ggatcgcttt cctctgaacg    420
cttctcgctg ctctttgagc ctgcagacac ctggggggat acggggaaaa ggctagaggt    480
cctgtattag aggtcacgtg agtgttttgc gacattttgc gacaccatgt ggtcacgctg    540
ggtatttaag cccgagtgag cacgcagggt ctccattttg aagcgggagg tttgaacgcg    600
cagccgccaa gccgaattct gcagatatcc ccgagtcctt caatgctatc attccctttg    660
atattggacc atatgcatag taccgagaaa ctagtgcgaa gtagtgatca ggtattgctg    720
ttagatatcc ccgagtcctt caatgctatc attctctttg atattggacc atatgcatag    780
taccgagaaa ctagtgcgaa gtagtgatca ggtattgctg ttagatatcc ccgagtcctt    840
caatgctatc attccctttg atattggacc atatgcatag taccgagaaa ctagtgcgaa    900
gtagtgatca ggtattgctg ttagatatcc ccgagtcctt caatgctatc attctctttg    960
atattggacc atatgcatag taccgagaaa ctagtgcgaa gtagtgatca ggtattgctg   1020
ttagatatcc ccgagtcctt caatgctatc attccctttg atattggacc atatgcatag   1080
taccgagaaa ctagtgcgaa gtagtgatca ggtattgctg ttagatatcc ccgagtcctt   1140
caatgctatc atttcctttg atattggatc atatgcatag taccgagaaa ctagtgcgaa   1200
gtagtgatca ggtattgctg ttaaggatcc atcacactgg cggccgctcg aggggagctc   1260
gcagggtctc cattttgaag cgggaggttt gaacgcgcag ccgccatgcc ggggttttac   1320
gagattgtga ttaaggtccc cagcgacctt gacgagcatc tgcccggcat ttctgacagc   1380
tttgtgaact gggtggccga gaaggaatgg gagttgccgc cagattctga catggatctg   1440
aatctgattg agcaggcacc cctgaccgtg gccgagaagc tgcagcgcga ctttctgacg   1500
gaatggcgcc gtgtgagtaa ggccccggag gctcttttct ttgtgcaatt tgagaaggga   1560
gagagctact tccacatgca cgtgctcgtg gaaaccaccg gggtgaaatc catggttttg   1620
ggacgtttcc tgagtcagat tcgcgaaaaa ctgattcaga gaatttacca gcgggatcga   1680
gccgactttg ccaaactggt tcgcggtcac aaagaccaga aatggcgccg gaggcgggaa   1740
caaggtggtg gatgagtgct acatccccaa ttacttgctc ccccaaaccc agcctgagct   1800
ccagtgggcg tggactaata tggaacagta tttaagcgcc tgtttgaatc tcacggagcg   1860
taaacggttg gtggcgcagc atctgacgca cgtgtcgcag acgcaggagc agaacaaaga   1920
gaatcagaat cccaattctg atgcgccggt gatcagatca aaaacttcag ccaggtacat   1980
ggagctggtc gggtggctcg tggacaaggg gattacctag gagaagcagt ggatccagga   2040
ggaccaggcc tcatacatct ccttcaatgc ggcctccaac tcgcggtccc aaatcaaggc   2100
tgccttggac aatgcgggaa agattatgag cctgactaaa accgcccccg actacctggt   2160
gggccagcag cccgtggagg acatttccag caatcggatt tataaaattt tggaactaaa   2220
cgggtacgat ccccaatatg cggcttccgt ctttctggga tgggccacga aaaagttcgg   2280
caagaggaac accatctggc tgtttgggcc tgcaactacc gggaagacca acatcgcgga   2340
ggccatagcc cacactgtgc ccttctacgg gtgcgtaaac tggaccaatg agaactttcc   2400
cttcaacgac tgtgtcgaca agatggtgat ctggtgggag gaggggaaga tgaccgccaa   2460
ggtcgtggag tcggccaaag ccattctcgg aggaagcaag gtgcgcgtgg accagaaatg   2520
caagtcctcg gcccagatag acccgactcc cgtgatcgtc acctccaaca ccaacatgtg   2580
cgccgtgatt gacgggaact caacgacctt cgaacaccag cagccgttgc aagaccggat   2640
```

```
gttcaaattt gaactcaccc gccgtctgga tcatgacttt gggaaggtca ccaagcagga   2700
agtcaaagac tttttccggt gggcaaagga tcacgtggtt gaggtggagc atgaattcta   2760
cgtcaaaaag ggtggagcca agaaaagacc cgcccccagt gacgcagata taagtgagcc   2820
caaacgggtg cgcgagtcag ttgcgcagcc atcgacgtca gacgcggaag cttcgatcaa   2880
ctacgcagac aggtaccaaa acaaatgttc tcgtcacgtg ggcatgaatc tgatgctgtt   2940
tccctgcaga caatgcgaga gaatgaatca gaattcaaat atctgcttca ctcacggaca   3000
gaaagactgt ttagagtgct ttcccgtgtc agaatctcaa cccgtttctg tcgtcaaaaa   3060
ggcgtatcag aaactgtgct acattcatca tatcatggga aaggtgccag acgcttgcac   3120
tgcctgcgat ctggtcaatg tggatttgga tgactgcatc tttgaacaat aaatgattta   3180
aatcaggtat ggctgccgat ggttatcttc cagattggct cgaggacact ctctctgaag   3240
gaataagaca gtggtggaag ctcaaacctg gcccaccacc accaaagccc gcagagcggc   3300
ataaggacga cagcaggggt cttgtgcttc ctgggtacaa gtacctcgga cccttcaacg   3360
gactcgacaa gggagagccg gtcaacgagg cagacgccgc ggccctcgag cacgacaaag   3420
cctacgaccg gcagctcgac agcggagaca acccgtacct caagtacaac cacgccgacg   3480
cggagtttca ggagcgcctt aaagaagata cgtcttttgg gggcaacctc ggacgagcag   3540
tcttccaggc gaaaaagagg gttcttgaac ctctgggcct ggttgaggaa cctgttaaga   3600
cggctccggg aaaaaagagg ccggtagagc actctcctgt ggagccagac tcctcctcgg   3660
gaaccggaaa ggcgggccag cagcctgcaa gaaaaagatt gaattttggt cagactggag   3720
acgcagactc agtacctgac ccccagcctc tcggacagcc accagcagcc ccctctggtc   3780
tgggaactaa tacgatggct acaggcagtg gcgcaccaat ggcagacaat aacgagggcg   3840
ccgacggagt gggtaattcc tcgggaaatt ggcattgcga ttccacatgg atgggcgaca   3900
gagtcatcac caccagcacc cgaacctggg ccctgcccac ctacaacaac cacctctaca   3960
aacaaatttc cagccaatca ggagcctcga acgacaatca ctactttggc tacagcaccc   4020
cttgggggta ttttgacttc aacagattcc actgccactt ttcaccacgt gactggcaaa   4080
gactcatcaa caacaactgg ggattccgac ccaagagact caacttcaag ctctttaaca   4140
ttcaagtcaa agaggtcacg cagaatgacg gtacgacgac gattgccaat aaccttacca   4200
gcacggttca ggtgtttact gactcggagt accagctccc gtacgtcctc ggctcggcgc   4260
atcaaggatg cctcccgccg ttcccagcag acgtcttcat ggtgccacag tatggatacc   4320
tcaccctgaa caacgggagt caggcagtag gacgctcttc attttactgc ctggagtact   4380
ttccttctca gatgctgcgt accggaaaca actttacctt cagctacact tttgaggacg   4440
ttcctttcca cagcagctac gctcacagcc agagtctgga ccgtctcatg aatcctctca   4500
tcgaccagta cctgtattac ttgagcagaa caaacactcc aagtggaacc accacgcagt   4560
caaggcttca gttttctcag gccggagcga gtgacattcg ggaccagtct aggaactggc   4620
ttcctggacc ctgttaccgc cagcagcgag tatcaaagac atctgcggat aacaacaaca   4680
gtgaatactc gtggactgga gctaccaagt accacctcaa tggcagagac tctctggtga   4740
atccgggccc ggccatggca agccacaagg acgatgaaga aaagtttttt cctcagagcg   4800
gggttctcat ctttgggaag caaggctcag agaaaacaaa tgtggacatt gaaaaggtca   4860
tgattacaga cgaagaggaa atcaggacaa ccaatcccgt ggctacggag cagtatggtt   4920
ctgtatctac caacctccag agaggcaaca gacaagcagc taccgcagat gtcaacacac   4980
aaggcgttct tccaggcatg gtctggcagg acagagatgt gtaccttcag ggcccatct    5040
```

```
gggcaaagat tccacacacg gacggacatt ttcacccctc tcccctcatg ggtggattcg   5100
gacttaaaca ccctcctcca cagattctca tcaagaacac cccggtacct gcgaatcctt   5160
cgaccacctt cagtgcggca aagtttgctt ccttcatcac acagtactcc acgggacagg   5220
tcagcgtgga gatcgagtgg gagctgcaga aggaaaacag caaacgctgg aatcccgaaa   5280
ttcagtacac ttccaactac aacaagtctg ttaatgtgga ctttactgtg gacactaatg   5340
gcgtgtattc agagcctcgc cccattggca ccagatacct gactcgtaat ctgtaattgc   5400
ttgttaatca ataaaccgtt taattcgttt cagttgaact ttggtctctg cgtatttctt   5460
tcttatctag tttccatgct cctccacggc caaggatctg cgatcgctcc ggtgcccgtc   5520
agtgggcaga gcgcacatcg cccacagtcc ccgagaagtt ggggggaggg gtcggcaatt   5580
gaacgggtgc ctagagaagg tggcgcgggg taaactggga aagtgatgtc gtgtactggc   5640
tccgcctttt tcccgagggt gggggagaac cgtatataag tgcagtagtc gccgtgaacg   5700
ttcttttttcg caacgggttt gccgccagaa cacagctgaa gcttcgaggg gctcgcatct   5760
ctccttcacg cgcccgccgc cctacctgag gccgccatcc acgccggttg agtcgcgttc   5820
tgccgcctcc cgcctgtggt gcctcctgaa ctgcgtccgc cgtctaggta agtttaaagc   5880
tcaggtcgag accgggcctt tgtccggcgc tcccttggag cctacctaga ctcagccggc   5940
tctccacgct ttgcctgacc ctgcttgctc aactctacgt ctttgtttcg ttttctgttc   6000
tgcgccgtta cagatccaag ctgtgaccgg cgcctactct agagctagcg aattcgaatt   6060
taaatcggat ccgcggccgc gcccctctcc ctcccccccc cctaacgtta ctggccgaag   6120
ccgcttggaa taaggccggt gtgcgtttgt ctatatgtta ttttccacca tattgccgtc   6180
ttttggcaat gtgagggccc ggaaacctgg ccctgtcttc ttgacgagca ttcctagggg   6240
tctttcccct ctcgccaaag gaatgcaagg tctgttgaat gtcgtgaagg aagcagttcc   6300
tctggaagct tcttgaagac aaacaacgtc tgtagcgacc ctttgcaggc agcggaaccc   6360
cccacctggc gacaggtgcc tctgcggcca aaagccacgt gtataagata cacctgcaaa   6420
ggcggcacaa ccccagtgcc acgttgtgag ttggatagtt gtggaaagag tcaaatggct   6480
ctcctcaagc gtattcaaca aggggctgaa ggatgcccag aaggtacccc attgtatggg   6540
atctgatctg gggcctcggt gcacatgctt tacatgtgtt tagtcgaggt taaaaaaacg   6600
tctaggcccc ccgaaccacg gggacgtggt tttcctttga aaaacacgat gataatatgg   6660
ccacaaccat ggcgtccgga atgattgaac aagatggatt gcacgcaggt tctccggccg   6720
cttgggtgga gaggctattc ggctatgact gggcacaaca gacaatcggc tgctctgatg   6780
ccgccgtgtt ccggctgtca gcgcaggggc gcccggttct ttttgtcaag accgacctgt   6840
ccggtgccct gaatgaactg caggacgagg cagcgcggct atcgtggctg gccgcgacgg   6900
gcgttccttg cgcagctgtg ctcgacgttg tcactgaagc gggaagggac tggctgctat   6960
tgggcgaagt gccggggcag gatctcctgt catctcacct tgctcctgcc gagaaagtat   7020
ccatcatggc tgatgcaatg cggcggctgc atacgcttga tccggctacc tgcccattcg   7080
accaccaagc gaaacatcgc atcgagcgag cacgtactcg gatggaagcc ggtcttgtcg   7140
atcaggatga tctggacgaa gagcatcagg ggctcgcgcc agccgaactg ttcgccaggc   7200
tcaaggcgcg catgcccgac ggcgaggatc tcgtcgtgac ccatggcgat gcctgcttgc   7260
cgaatatcat ggtggaaaat ggccgctttt ctggattcat cgactgtggc cggctgggtg   7320
tggcggaccg ctatcaggac atagcgttgg ctacccgtga tattgctgaa gagcttggcg   7380
```

```
gcgaatgggc tgaccgcttc ctcgtgcttt acggtatcgc cgctcccgat tcgcagcgca   7440

tcgccttcta tcgccttctt gacgagttct tctgagtcga caatcaacct ctggattaca   7500

aaatttgtga aagattgact ggtattctta actatgttgc tccttttacg ctatgtggat   7560

acgctgcttt aatgcctttg tatcatgcgt taactaaact tgtttattgc agcttataat   7620

ggttacaaat aaagcaatag catcacaaat ttcacaaata aagcattttt ttcactgcat   7680

tctagttgtg gtttgtccaa actcatcaat gtatcttatc atgtctggaa ttgactcaaa   7740

tgatgtcaat tagtctatca gaagctcatc tggtctccct tccgggggac aagacatccc   7800

tgtttaatat ttaaacagca gtgttcccaa actgggttct tatatccctt gctctggtca   7860

accaggttgc agggtttcct gtcctcacag gaacgaagtc cctaaagaaa cagtggcagc   7920

caggtttagc cccggaattg actggattcc tttttaggg cccattggta tggctttttc   7980

cccgtatccc cccaggtgtc tgcaggctca aagagcagcg agaagcgttc agaggaaagc   8040

gatcccgtgc caccttcccc gtgcccgggc tgtccccgca cgctgccggc tcggggatgc   8100

ggggggagcg ccggaccgga gcggagcccc gggcggctcg ctgctgcccc ctagcggggg   8160

agggacgtaa ttacatccct gggggctttg gggggggct gtccctgata tctataacaa   8220

gaaaatatat atataataag ttatcacgta agtagaacat gaaataacaa tataattatc   8280

gtatgagtta aatcttaaaa gtcacgtaaa agataatcat gcgtcatttt gactcacgcg   8340

gtcgttatag ttcaaaatca gtgacactta ccgcattgac aagcacgcct cacgggagct   8400

ccaagcggcg actgagatgt cctaaatgca cagcgacgga ttcgcgctat ttagaaagag   8460

agagcaatat ttcaagaatg catgcgtcaa ttttacgcag actatctttc taggg        8515
```

<210> SEQ ID NO 16
<211> LENGTH: 7877
<212> TYPE: DNA
<213> ORGANISM: Artificial Sequence
<220> FEATURE:
<223> OTHER INFORMATION: Synthetic polynucleotide

<400> SEQUENCE: 16

```
ccctagaaag ataatcatat tgtgacgtac gttaaagata atcatgtgta aaattgacgc     60

atgtgtttta tcggtctgta tatcgaggtt tatttattaa tttgaataga tattaagttt    120

tattatattt acacttacat actaataata aattcaacaa acaatttatt tatgtttatt    180

tatttattaa aaaaaacaaa aactcaaaat ttcttctata aagtaacaaa acttttatga    240

gggacagccc ccccccaaag cccccaggga tgtaattacg tccctccccc gctagggggc    300

agcagcgagc cgcccggggc tccgctccgg tccggcgctc cccccgcatc cccgagccgg    360

cagcgtgcgg ggacagcccg ggcacgggga aggtggcacg ggatcgcttt cctctgaacg    420

cttctcgctg ctctttgagc ctgcagacac ctggggggat acggggaaaa ggctagaggt    480

cctgtattag aggtcacgtg agtgttttgc gacattttgc gacaccatgt ggtcacgctg    540

ggtatttaag cccgagtgag cacgcagggt ctccattttg aagcgaggat ccatcacact    600

ggcggccgct cgaggggagc tcgcagggtc tccattttga agcgggaggt ttgaacgcgc    660

agccgccatg ccggggtttt acgagattgt gattaaggtc cccagcgacc ttgacgagca    720

tctgcccggc atttctgaca gctttgtgaa ctgggtggcc gagaaggaat gggagttgcc    780

gccagattct gacatggatc tgaatctgat tgagcaggca cccctgaccg tggccgagaa    840

gctgcagcgc gactttctga cggaatggcg ccgtgtgagt aaggccccgg aggctctttt    900

ctttgtgcaa tttgagaagg gagagagcta cttccacatg cacgtgctcg tggaaaccac    960
```

```
cggggtgaaa tccatggttt tgggacgttt cctgagtcag attcgcgaaa aactgattca   1020
gagaatttac cagcgggatc gagccgactt tgccaaactg gttcgcggtc acaaagacca   1080
gaaatggcgc cggaggcggg aacaaggtgg tggatgagtg ctacatcccc aattacttgc   1140
tccccaaaac ccagcctgag ctccagtggg cgtggactaa tatggaacag tatttaagcg   1200
cctgtttgaa tctcacggag cgtaaacggt tggtggcgca gcatctgacg cacgtgtcgc   1260
agacgcagga gcagaacaaa gagaatcaga atcccaattc tgatgcgccg gtgatcagat   1320
caaaaacttc agccaggtac atggagctgg tcgggtggct cgtggacaag gggattacct   1380
aggagaagca gtggatccag gaggaccagg cctcatacat ctccttcaat gcggcctcca   1440
actcgcggtc ccaaatcaag gctgccttgg acaatgcggg aaagattatg agcctgacta   1500
aaaccgcccc cgactacctg gtgggccagc agcccgtgga ggacatttcc agcaatcgga   1560
tttataaaat tttggaacta aacgggtacg atccccaata tgcggcttcc gtctttctgg   1620
gatgggccac gaaaaagttc ggcaagagga acaccatctg gctgtttggg cctgcaacta   1680
ccgggaagac caacatcgcg gaggccatag cccacactgt gcccttctac gggtgcgtaa   1740
actggaccaa tgagaacttt cccttcaacg actgtgtcga caagatggtg atctggtggg   1800
aggaggggaa gatgaccgcc aaggtcgtgg agtcggccaa agccattctc ggaggaagca   1860
aggtgcgcgt ggaccagaaa tgcaagtcct cggcccagat agacccgact cccgtgatcg   1920
tcacctccaa caccaacatg tgcgccgtga ttgacgggaa ctcaacgacc ttcgaacacc   1980
agcagccgtt gcaagaccgg atgttcaaat ttgaactcac ccgccgtctg gatcatgact   2040
ttgggaaggt caccaagcag gaagtcaaag actttttccg gtgggcaaag gatcacgtgg   2100
ttgaggtgga gcatgaattc tacgtcaaaa agggtggagc caagaaaaga cccgcccca    2160
gtgacgcaga tataagtgag cccaaacggg tgcgcgagtc agttgcgcag ccatcgacgt   2220
cagacgcgga agcttcgatc aactacgcag acaggtacca aaacaaatgt tctcgtcacg   2280
tgggcatgaa tctgatgctg tttccctgca gacaatgcga gagaatgaat cagaattcaa   2340
atatctgctt cactcacgga cagaaagact gtttagagtg ctttcccgtg tcagaatctc   2400
aacccgtttc tgtcgtcaaa aaggcgtatc agaaactgtg ctacattcat catatcatgg   2460
gaaaggtgcc agacgcttgc actgcctgcg atctggtcaa tgtggatttg gatgactgca   2520
tctttgaaca ataaatgatt taaatcaggt atggctgccg atggttatct tccagattgg   2580
ctcgaggaca ctctctctga aggaataaga cagtggtgga agctcaaacc tggcccacca   2640
ccaccaaagc ccgcagagcg gcataaggac gacagcaggg gtcttgtgct tcctgggtac   2700
aagtacctcg gacccttcaa cggactcgac aagggagagc cggtcaacga ggcagacgcc   2760
gcggccctcg agcacgacaa agcctacgac cggcagctcg acagcggaga caacccgtac   2820
ctcaagtaca accacgccga cgcggagttt caggagcgcc ttaaagaaga tacgtctttt   2880
gggggcaacc tcggacgagc agtcttccag gcgaaaaaga gggttcttga acctctgggc   2940
ctggttgagg aacctgttaa gacggctccg ggaaaaaaga ggccggtaga gcactctcct   3000
gtggagccag actcctcctc gggaaccgga aaggcgggcc agcagcctgc aagaaaaaga   3060
ttgaattttg gtcagactgg agacgcagac tcagtacctg acccccagcc tctcggacag   3120
ccaccagcag ccccctctgg tctgggaact aatacgatgg ctacaggcag tggcgcacca   3180
atggcagaca ataacgaggg cgccgacgga gtgggtaatt cctcgggaaa ttggcattgc   3240
gattccacat ggatgggcga cagagtcatc accaccagca cccgaacctg ggccctgccc   3300
```

```
acctacaaca accacctcta caaacaaatt tccagccaat caggagcctc gaacgacaat   3360
cactactttg gctacagcac cccttggggg tattttgact tcaacagatt ccactgccac   3420
ttttcaccac gtgactggca aagactcatc aacaacaact ggggattccg acccaagaga   3480
ctcaacttca agctctttaa cattcaagtc aaagaggtca cgcagaatga cggtacgacg   3540
acgattgcca ataaccttac cagcacggtt caggtgttta ctgactcgga gtaccagctc   3600
ccgtacgtcc tcggctcggc gcatcaagga tgcctcccgc cgttcccagc agacgtcttc   3660
atggtgccac agtatggata cctcaccctg aacaacggga gtcaggcagt aggacgctct   3720
tcattttact gcctggagta ctttccttct cagatgctgc gtaccggaaa caactttacc   3780
ttcagctaca cttttgagga cgttcctttc cacagcagct acgctcacag ccagagtctg   3840
gaccgtctca tgaatcctct catcgaccag tacctgtatt acttgagcag aacaaacact   3900
ccaagtggaa ccaccacgca gtcaaggctt cagttttctc aggccggagc gagtgacatt   3960
cgggaccagt ctaggaactg gcttcctgga ccctgttacc gccagcagcg agtatcaaag   4020
acatctgcgg ataacaacaa cagtgaatac tcgtggactg gagctaccaa gtaccacctc   4080
aatggcagag actctctggt gaatccgggc ccggccatgg caagccacaa ggacgatgaa   4140
gaaaagtttt ttcctcagag cggggttctc atctttggga agcaaggctc agagaaaaca   4200
aatgtggaca ttgaaaaggt catgattaca gacgaagagg aaatcaggac aaccaatccc   4260
gtggctacgg agcagtatgg ttctgtatct accaacctcc agagaggcaa cagacaagca   4320
gctaccgcag atgtcaacac acaaggcgtt cttccaggca tggtctggca ggacagagat   4380
gtgtaccttc aggggcccat ctgggcaaag attccacaca cggacggaca ttttcacccc   4440
tctcccctca tgggtggatt cggacttaaa caccctcctc cacagattct catcaagaac   4500
accccggtac ctgcgaatcc ttcgaccacc ttcagtgcgg caaagtttgc ttccttcatc   4560
acacagtact ccacgggaca ggtcagcgtg gagatcgagt gggagctgca gaaggaaaac   4620
agcaaacgct ggaatcccga aattcagtac acttccaact acaacaagtc tgttaatgtg   4680
gactttactg tggacactaa tggcgtgtat tcagagcctc gccccattgg caccagatac   4740
ctgactcgta atctgtaatt gcttgttaat caataaaccg tttaattcgt ttcagttgaa   4800
ctttggtctc tgcgtatttc tttcttatct agtttccatg ctcctccacg gccaaggatc   4860
tgcgatcgct ccggtgcccg tcagtgggca gagcgcacat cgcccacagt ccccgagaag   4920
ttgggggggag gggtcggcaa ttgaacgggt gcctagagaa ggtggcgcgg ggtaaactgg   4980
gaaagtgatg tcgtgtactg gctccgcctt tttcccgagg gtgggggaga accgtatata   5040
agtgcagtag tcgccgtgaa cgttcttttt cgcaacgggt ttgccgccag aacacagctg   5100
aagcttcgag gggctcgcat ctctccttca cgcgcccgcc gccctacctg aggccgccat   5160
ccacgccggt tgagtcgcgt tctgccgcct cccgcctgtg gtgcctcctg aactgcgtcc   5220
gccgtctagg taagtttaaa gctcaggtcg agaccgggcc tttgtccggc gctcccttgg   5280
agcctaccta gactcagccg gctctccacg ctttgcctga ccctgcttgc tcaactctac   5340
gtctttgttt cgttttctgt tctgcgccgt tacagatcca agctgtgacc ggcgcctact   5400
ctagagctag cgaattcgaa tttaaatcgg atccgcggcc gcgcccctct ccctcccccc   5460
cccctaacgt tactggccga agccgcttgg aataaggccg gtgtgcgttt gtctatatgt   5520
tattttccac catattgccg tcttttggca atgtgagggc ccggaaacct ggccctgtct   5580
tcttgacgag cattcctagg ggtctttccc ctctcgccaa aggaatgcaa ggtctgttga   5640
atgtcgtgaa ggaagcagtt cctctggaag cttcttgaag acaaacaacg tctgtagcga   5700
```

```
ccctttgcag gcagcggaac cccccacctg gcgacaggtg cctctgcggc caaaagccac   5760
gtgtataaga tacacctgca aaggcggcac aaccccagtg ccacgttgtg agttggatag   5820
ttgtggaaag agtcaaatgg ctctcctcaa gcgtattcaa caaggggctg aaggatgccc   5880
agaaggtacc ccattgtatg ggatctgatc tggggcctcg gtgcacatgc tttacatgtg   5940
tttagtcgag gttaaaaaaa cgtctaggcc ccccgaacca cggggacgtg gttttccttt   6000
gaaaaacacg atgataatat ggccacaacc atggcgtccg gaatgattga acaagatgga   6060
ttgcacgcag gttctccggc cgcttgggtg gagaggctat tcggctatga ctgggcacaa   6120
cagacaatcg gctgctctga tgccgccgtg ttccggctgt cagcgcaggg gcgcccggtt   6180
ctttttgtca agaccgacct gtccggtgcc ctgaatgaac tgcaggacga ggcagcgcgg   6240
ctatcgtggc tggccgcgac gggcgttcct tgcgcagctg tgctcgacgt tgtcactgaa   6300
gcgggaaggg actggctgct attgggcgaa gtgccggggc aggatctcct gtcatctcac   6360
cttgctcctg ccgagaaagt atccatcatg gctgatgcaa tgcggcggct gcatacgctt   6420
gatccggcta cctgcccatt cgaccaccaa gcgaaacatc gcatcgagcg agcacgtact   6480
cggatggaag ccggtcttgt cgatcaggat gatctggacg aagagcatca ggggctcgcg   6540
ccagccgaac tgttcgccag gctcaaggcg cgcatgcccg acggcgagga tctcgtcgtg   6600
acccatggcg atgcctgctt gccgaatatc atggtggaaa atggccgctt ttctggattc   6660
atcgactgtg gccggctggg tgtggcggac cgctatcagg acatagcgtt ggctacccgt   6720
gatattgctg aagagcttgg cggcgaatgg gctgaccgct tcctcgtgct ttacggtatc   6780
gccgctcccg attcgcagcg catcgccttc tatcgccttc ttgacgagtt cttctgagtc   6840
gacaatcaac ctctggatta caaaatttgt gaaagattga ctggtattct taactatgtt   6900
gctcctttta cgctatgtgg atacgctgct ttaatgcctt tgtatcatgc gttaactaaa   6960
cttgtttatt gcagcttata atggttacaa ataaagcaat agcatcacaa atttcacaaa   7020
taaagcattt ttttcactgc attctagttg tggtttgtcc aaactcatca atgtatctta   7080
tcatgtctgg aattgactca aatgatgtca attagtctat cagaagctca tctggtctcc   7140
cttccggggg acaagacatc cctgtttaat atttaaacag cagtgttccc aaactgggtt   7200
cttatatccc ttgctctggt caaccaggtt gcagggtttc ctgtcctcac aggaacgaag   7260
tccctaaaga aacagtggca gccaggttta gccccggaat tgactggatt cctttttttag  7320
ggcccattgg tatggctttt tccccgtatc cccccaggtg tctgcaggct caaagagcag   7380
cgagaagcgt tcagaggaaa gcgatcccgt gccaccttcc ccgtgcccgg gctgtccccg   7440
cacgctgccg gctcggggat gcggggggag cgccggaccg gagcggagcc ccgggcggct   7500
cgctgctgcc ccctagcggg ggagggacgt aattacatcc ctgggggctt tggggggggg   7560
ctgtccctga tatctataac aagaaaatat atatataata agttatcacg taagtagaac   7620
atgaaataac aatataatta tcgtatgagt taaatcttaa aagtcacgta aaagataatc   7680
atgcgtcatt ttgactcacg cggtcgttat agttcaaaat cagtgacact taccgcattg   7740
acaagcacgc ctcacgggag ctccaagcgg cgactgagat gtcctaaatg cacagcgacg   7800
gattcgcgct atttagaaag agagagcaat atttcaagaa tgcatgcgtc aattttacgc   7860
agactatctt tctaggg                                                  7877
```

<210> SEQ ID NO 17
<211> LENGTH: 8025
<212> TYPE: DNA

<213> ORGANISM: Artificial Sequence
<220> FEATURE:
<223> OTHER INFORMATION: Synthetic polynucleotide

<400> SEQUENCE: 17
ccctagaaag ataatcatat tgtgacgtac gttaaagata atcatgtgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaacaaa aactcaaaat ttcttctata aagtaacaaa tcctgtatta 240
gaggtcacgt gagtgttttg cgacattttg cgacaccatg tggtcacgct gggtatttaa 300
gcccgagtga gcacgcaggg tctccatttt gaagcgggag gtttgaacgc gcagccgcca 360
agccgaattc tgcagatatc cccgagtcct tcaatgctat cattcccttt gatattggac 420
catatgcata gtaccgagaa actagtgcga agtagtgatc aggtattgct gttagatatc 480
cccgagtcct tcaatgctat cattctcttt gatattggac catatgcata gtaccgagaa 540
actagtgcga agtagtgatc aggtattgct gttagatatc cccgagtcct tcaatgctat 600
cattcccttt gatattggac catatgcata gtaccgagaa actagtgcga agtagtgatc 660
aggtattgct gttagatatc cccgagtcct tcaatgctat cattctcttt gatattggac 720
catatgcata gtaccgagaa actagtgcga agtagtgatc aggtattgct gttagatatc 780
cccgagtcct tcaatgctat cattcccttt gatattggac catatgcata gtaccgagaa 840
actagtgcga agtagtgatc aggtattgct gttagatatc cccgagtcct tcaatgctat 900
catttccttt gatattggat catatgcata gtaccgagaa actagtgcga agtagtgatc 960
aggtattgct gttaaggatc catcacactg gcggccgctc gaggggagct cgcagggtct 1020
ccattttgaa gcgggaggtt tgaacgcgca gccgccatgc cggggtttta cgagattgtg 1080
attaaggtcc ccagcgacct tgacgagcat ctgcccggca tttctgacag ctttgtgaac 1140
tgggtggccg agaaggaatg ggagttgccg ccagattctg acatggatct gaatctgatt 1200
gagcaggcac ccctgaccgt ggccgagaag ctgcagcgcg actttctgac ggaatggcgc 1260
cgtgtgagta aggccccgga ggctcttttc tttgtgcaat ttgagaaggg agagagctac 1320
ttccacatgc acgtgctcgt ggaaaccacc ggggtgaaat ccatggtttt gggacgtttc 1380
ctgagtcaga ttcgcgaaaa actgattcag agaatttacc agcgggatcg agccgacttt 1440
gccaaactgg ttcgcggtca caaagaccag aaatggcgcc ggaggcggga acaaggtggt 1500
ggatgagtgc tacatcccca attacttgct ccccaaaacc cagcctgagc tccagtgggc 1560
gtggactaat atggaacagt atttaagcgc ctgtttgaat ctcacggagc gtaaacggtt 1620
ggtggcgcag catctgacgc acgtgtcgca gacgcaggag cagaacaaag agaatcagaa 1680
tcccaattct gatgcgccgg tgatcagatc aaaaacttca gccaggtaca tggagctggt 1740
cgggtggctc gtggacaagg ggattaccta ggagaagcag tggatccagg aggaccaggc 1800
ctcatacatc tccttcaatg cggcctccaa ctcgcggtcc caaatcaagg ctgccttgga 1860
caatgcggga aagattatga gcctgactaa aaccgccccc gactacctgg tgggccagca 1920
gcccgtggag gacatttcca gcaatcggat ttataaaatt ttggaactaa acgggtacga 1980
tccccaatat gcggcttccg tctttctggg atgggccacg aaaaagttcg gcaagaggaa 2040
caccatctgg ctgtttgggc ctgcaactac cgggaagacc aacatcgcgg aggccatagc 2100
ccacactgtg cccttctacg ggtgcgtaaa ctggaccaat gagaactttc ccttcaacga 2160
ctgtgtcgac aagatggtga tctggtggga ggaggggaag atgaccgcca aggtcgtgga 2220

```
gtcggccaaa gccattctcg gaggaagcaa ggtgcgcgtg gaccagaaat gcaagtcctc   2280
ggcccagata gacccgactc ccgtgatcgt cacctccaac accaacatgt gcgccgtgat   2340
tgacgggaac tcaacgacct tcgaacacca gcagccgttg caagaccgga tgttcaaatt   2400
tgaactcacc cgccgtctgg atcatgactt tgggaaggtc accaagcagg aagtcaaaga   2460
ctttttccgg tgggcaaagg atcacgtggt tgaggtggag catgaattct acgtcaaaaa   2520
gggtggagcc aagaaaagac ccgcccccag tgacgcagat ataagtgagc ccaaacgggt   2580
gcgcgagtca gttgcgcagc catcgacgtc agacgcggaa gcttcgatca actacgcaga   2640
caggtaccaa aacaaatgtt ctcgtcacgt gggcatgaat ctgatgctgt ttccctgcag   2700
acaatgcgag agaatgaatc agaattcaaa tatctgcttc actcacggac agaaagactg   2760
tttagagtgc tttcccgtgt cagaatctca acccgtttct gtcgtcaaaa aggcgtatca   2820
gaaactgtgc tacattcatc atatcatggg aaaggtgcca gacgcttgca ctgcctgcga   2880
tctggtcaat gtggatttgg atgactgcat ctttgaacaa taaatgattt aaatcaggta   2940
tggctgccga tggttatctt ccagattggc tcgaggacac tctctctgaa ggaataagac   3000
agtggtggaa gctcaaacct ggcccaccac caccaaagcc cgcagagcgg cataaggacg   3060
acagcagggg tcttgtgctt cctgggtaca agtacctcgg acccttcaac ggactcgaca   3120
agggagagcc ggtcaacgag gcagacgccg cggccctcga gcacgacaaa gcctacgacc   3180
ggcagctcga cagcggagac aacccgtacc tcaagtacaa ccacgccgac gcggagtttc   3240
aggagcgcct taaagaagat acgtcttttg ggggcaacct cggacgagca gtcttccagg   3300
cgaaaaagag ggttcttgaa cctctgggcc tggttgagga acctgttaag acggctccgg   3360
gaaaaaagag gccggtagag cactctcctg tggagccaga ctcctcctcg ggaaccggaa   3420
aggcgggcca gcagcctgca agaaaaagat tgaattttgg tcagactgga gacgcagact   3480
cagtacctga cccccagcct ctcggacagc caccagcagc cccctctggt ctgggaacta   3540
atacgatggc tacaggcagt ggcgcaccaa tggcagacaa taacgagggc gccgacggag   3600
tgggtaattc ctcgggaaat tggcattgcg attccacatg gatgggcgac agagtcatca   3660
ccaccagcac ccgaacctgg gccctgccca cctacaacaa ccacctctac aaacaaattt   3720
ccagccaatc aggagcctcg aacgacaatc actactttgg ctacagcacc ccttgggggt   3780
attttgactt caacagattc cactgccact tttcaccacg tgactggcaa agactcatca   3840
acaacaactg gggattccga cccaagagac tcaacttcaa gctctttaac attcaagtca   3900
aagaggtcac gcagaatgac ggtacgacga cgattgccaa taaccttacc agcacggttc   3960
aggtgtttac tgactcggag taccagctcc cgtacgtcct cggctcggcg catcaaggat   4020
gcctcccgcc gttcccagca gacgtcttca tggtgccaca gtatggatac ctcaccctga   4080
acaacgggag tcaggcagta ggacgctctt cattttactg cctggagtac tttccttctc   4140
agatgctgcg taccggaaac aactttacct tcagctacac ttttgaggac gttcctttcc   4200
acagcagcta cgctcacagc cagagtctgg accgtctcat gaatcctctc atcgaccagt   4260
acctgtatta cttgagcaga acaaacactc caagtggaac caccacgcag tcaaggcttc   4320
agttttctca ggccggagcg agtgacattc gggaccagtc taggaactgg cttcctggac   4380
cctgttaccg ccagcagcga gtatcaaaga catctgcgga taacaacaac agtgaatact   4440
cgtggactgg agctaccaag taccacctca atggcagaga ctctctggtg aatccgggcc   4500
cggccatggc aagccacaag gacgatgaag aaaagttttt tcctcagagc ggggttctca   4560
```

```
tctttgggaa gcaaggctca gagaaaacaa atgtggacat tgaaaaggtc atgattacag   4620
acgaagagga aatcaggaca accaatcccg tggctacgga gcagtatggt tctgtatcta   4680
ccaacctcca gagaggcaac agacaagcag ctaccgcaga tgtcaacaca caaggcgttc   4740
ttccaggcat ggtctggcag gacagagatg tgtaccttca ggggcccatc tgggcaaaga   4800
ttccacacac ggacggacat tttcacccct ctcccctcat gggtggattc ggacttaaac   4860
accctcctcc acagattctc atcaagaaca ccccggtacc tgcgaatcct tcgaccacct   4920
tcagtgcggc aaagtttgct tccttcatca cacagtactc cacgggacag gtcagcgtgg   4980
agatcgagtg ggagctgcag aaggaaaaca gcaaacgctg gaatcccgaa attcagtaca   5040
cttccaacta caacaagtct gttaatgtgg actttactgt ggacactaat ggcgtgtatt   5100
cagagcctcg ccccattggc accagatacc tgactcgtaa tctgtaattg cttgttaatc   5160
aataaaccgt ttaattcgtt tcagttgaac tttggtctct gcgtatttct ttcttatcta   5220
gtttccatgc tcctccacgg ccaaggatct gcgatcgctc cggtgcccgt cagtgggcag   5280
agcgcacatc gcccacagtc cccgagaagt tggggggagg ggtcggcaat tgaacgggtg   5340
cctagagaag gtggcgcggg gtaaactggg aaagtgatgt cgtgtactgg ctccgccttt   5400
ttcccgaggg tgggggagaa ccgtatataa gtgcagtagt cgccgtgaac gttctttttc   5460
gcaacgggtt tgccgccaga acacagctga agcttcgagg ggctcgcatc tctccttcac   5520
gcgcccgccg ccctacctga ggccgccatc cacgccggtt gagtcgcgtt ctgccgcctc   5580
ccgcctgtgg tgcctcctga actgcgtccg ccgtctaggt aagtttaaag ctcaggtcga   5640
gaccgggcct ttgtccggcg ctcccttgga gcctacctag actcagccgg ctctccacgc   5700
tttgcctgac cctgcttgct caactctacg tctttgtttc gttttctgtt ctgcgccgtt   5760
acagatccaa gctgtgaccg gcgcctactc tagagctagc gaattcgaat ttaaatcgga   5820
tccgcggccg cgcccctctc cctccccccc ccctaacgtt actggccgaa gccgcttgga   5880
ataaggccgg tgtgcgtttg tctatatgtt attttccacc atattgccgt cttttggcaa   5940
tgtgagggcc cggaaacctg gccctgtctt cttgacgagc attcctaggg gtctttcccc   6000
tctcgccaaa ggaatgcaag gtctgttgaa tgtcgtgaag gaagcagttc ctctggaagc   6060
ttcttgaaga caaacaacgt ctgtagcgac cctttgcagg cagcggaacc ccccacctgg   6120
cgacaggtgc ctctgcggcc aaaagccacg tgtataagat acacctgcaa aggcggcaca   6180
accccagtgc cacgttgtga gttggatagt tgtggaaaga gtcaaatggc tctcctcaag   6240
cgtattcaac aaggggctga aggatgccca gaaggtaccc cattgtatgg gatctgatct   6300
ggggcctcgg tgcacatgct ttacatgtgt ttagtcgagg ttaaaaaaac gtctaggccc   6360
cccgaaccac ggggacgtgg ttttcctttg aaaaacacga tgataatatg gccacaacca   6420
tggcgtccgg aatgattgaa caagatggat tgcacgcagg ttctccggcc gcttgggtgg   6480
agaggctatt cggctatgac tgggcacaac agacaatcgg ctgctctgat gccgccgtgt   6540
tccggctgtc agcgcagggg cgcccggttc tttttgtcaa gaccgacctg tccggtgccc   6600
tgaatgaact gcaggacgag gcagcgcggc tatcgtggct ggccgcgacg ggcgttcctt   6660
gcgcagctgt gctcgacgtt gtcactgaag cgggaaggga ctggctgcta ttgggcgaag   6720
tgccggggca ggatctcctg tcatctcacc ttgctcctgc cgagaaagta tccatcatgg   6780
ctgatgcaat gcggcggctg catacgcttg atccggctac ctgcccattc gaccaccaag   6840
cgaaacatcg catcgagcga gcacgtactc ggatggaagc cggtcttgtc gatcaggatg   6900
atctggacga agagcatcag gggctcgcgc cagccgaact gttcgccagg ctcaaggcgc   6960
```

```
gcatgcccga cggcgaggat ctcgtcgtga cccatggcga tgcctgcttg ccgaatatca   7020

tggtggaaaa tggccgcttt tctggattca tcgactgtgg ccggctgggt gtggcggacc   7080

gctatcagga catagcgttg gctacccgtg atattgctga agagcttggc ggcgaatggg   7140

ctgaccgctt cctcgtgctt tacggtatcg ccgctcccga ttcgcagcgc atcgccttct   7200

atcgccttct tgacgagttc ttctgagtcg acaatcaacc tctggattac aaaatttgtg   7260

aaagattgac tggtattctt aactatgttg ctccttttac gctatgtgga tacgctgctt   7320

taatgccttt gtatcatgcg ttaactaaac ttgtttattg cagcttataa tggttacaaa   7380

taaagcaata gcatcacaaa tttcacaaat aaagcatttt tttcactgca ttctagttgt   7440

ggtttgtcca aactcatcaa tgtatcttat catgtctgga attgactcaa atgatgtcaa   7500

ttagtctatc agaagctcat ctggtctccc ttccgggggga caagacatcc ctgtttaata   7560

tttaaacagc agtgttccca aactgggttc ttatatccct tgctctggtc aaccaggttg   7620

cagggtttcc tgtcctcaca ggaacgaagt ccctaaagaa acagtggcag ccaggtttag   7680

ccccggaatt gactggattc ctttttagg gcccattggt attataacaa gaaaatatat   7740

atataataag ttatcacgta agtagaacat gaaataacaa tataattatc gtatgagtta   7800

aatcttaaaa gtcacgtaaa agataatcat gcgtcatttt gactcacgcg gtcgttatag   7860

ttcaaaatca gtgacactta ccgcattgac aagcacgcct cacgggagct ccaagcggcg   7920

actgagatgt cctaaatgca cagcgacgga ttcgcgctat ttagaaagag agagcaatat   7980

ttcaagaatg catgcgtcaa ttttacgcag actatctttc taggg                   8025
```

```
<210> SEQ ID NO 18
<211> LENGTH: 7387
<212> TYPE: DNA
<213> ORGANISM: Artificial Sequence
<220> FEATURE:
<223> OTHER INFORMATION: Synthetic polynucleotide

<400> SEQUENCE: 18
```

```
ccctagaaag ataatcatat tgtgacgtac gttaaagata atcatgtgta aaattgacgc     60

atgtgtttta tcggtctgta tatcgaggtt tatttattaa tttgaataga tattaagttt    120

tattatattt acacttacat actaataata aattcaacaa acaatttatt tatgtttatt    180

tatttattaa aaaaaacaaa aactcaaaat ttcttctata aagtaacaaa tcctgtatta    240

gaggtcacgt gagtgttttg cgacattttg cgacaccatg tggtcacgct gggtatttaa    300

gcccgagtga gcacgcaggg tctccatttt gaagcgagga tccatcacac tggcggccgc    360

tcgaggggag ctcgcagggt ctccattttg aagcgggagg tttgaacgcg cagccgccat    420

gccggggttt tacgagattg tgattaaggt ccccagcgac cttgacgagc atctgcccgg    480

catttctgac agctttgtga actgggtggc cgagaaggaa tgggagttgc cgccagattc    540

tgacatggat ctgaatctga ttgagcaggc acccctgacc gtggccgaga agctgcagcg    600

cgactttctg acggaatggc gccgtgtgag taaggccccg gaggctcttt tctttgtgca    660

atttgagaag ggagagagct acttccacat gcacgtgctc gtggaaacca ccggggtgaa    720

atccatggtt ttgggacgtt tcctgagtca gattcgcgaa aaactgattc agagaattta    780

ccagcgggat cgagccgact ttgccaaact ggttcgcggt cacaaagacc agaaatggcg    840

ccggaggcgg gaacaaggtg gtggatgagt gctacatccc caattacttg ctccccaaaa    900

cccagcctga gctccagtgg gcgtggacta atatggaaca gtatttaagc gcctgtttga    960
```

```
atctcacgga gcgtaaacgg ttggtggcgc agcatctgac gcacgtgtcg cagacgcagg   1020
agcagaacaa agagaatcag aatcccaatt ctgatgcgcc ggtgatcaga tcaaaaactt   1080
cagccaggta catggagctg gtcgggtggc tcgtggacaa ggggattacc taggagaagc   1140
agtggatcca ggaggaccag gcctcataca tctccttcaa tgcggcctcc aactcgcggt   1200
cccaaatcaa ggctgccttg gacaatgcgg gaaagattat gagcctgact aaaaccgccc   1260
ccgactacct ggtgggccag cagcccgtgg aggacatttc cagcaatcgg atttataaaa   1320
ttttggaact aaacgggtac gatccccaat atgcggcttc cgtctttctg ggatgggcca   1380
cgaaaaagtt cggcaagagg aacaccatct ggctgtttgg gcctgcaact accgggaaga   1440
ccaacatcgc ggaggccata gcccacactg tgcccttcta cgggtgcgta aactggacca   1500
atgagaactt tcccttcaac gactgtgtcg acaagatggt gatctggtgg gaggagggga   1560
agatgaccgc caaggtcgtg gagtcggcca aagccattct cggaggaagc aaggtgcgcg   1620
tggaccagaa atgcaagtcc tcggcccaga tagacccgac tcccgtgatc gtcacctcca   1680
acaccaacat gtgcgccgtg attgacggga actcaacgac cttcgaacac cagcagccgt   1740
tgcaagaccg gatgttcaaa tttgaactca cccgccgtct ggatcatgac tttgggaagg   1800
tcaccaagca ggaagtcaaa gactttttcc ggtgggcaaa ggatcacgtg gttgaggtgg   1860
agcatgaatt ctacgtcaaa aagggtggag ccaagaaaag acccgccccc agtgacgcag   1920
atataagtga gcccaaacgg gtgcgcgagt cagttgcgca gccatcgacg tcagacgcgg   1980
aagcttcgat caactacgca gacaggtacc aaaacaaatg ttctcgtcac gtgggcatga   2040
atctgatgct gtttccctgc agacaatgcg agagaatgaa tcagaattca aatatctgct   2100
tcactcacgg acagaaagac tgtttagagt gctttcccgt gtcagaatct caacccgttt   2160
ctgtcgtcaa aaaggcgtat cagaaactgt gctacattca tcatatcatg ggaaaggtgc   2220
cagacgcttg cactgcctgc gatctggtca atgtggattt ggatgactgc atctttgaac   2280
aataaatgat ttaaatcagg tatggctgcc gatggttatc ttccagattg gctcgaggac   2340
actctctctg aaggaataag acagtggtgg aagctcaaac ctggcccacc accaccaaag   2400
cccgcagagc ggcataagga cgacagcagg ggtcttgtgc ttcctgggta caagtacctc   2460
ggacccttca acggactcga caagggagag ccggtcaacg aggcagacgc cgcggccctc   2520
gagcacgaca aagcctacga ccggcagctc gacagcggag acaacccgta cctcaagtac   2580
aaccacgccg acgcggagtt tcaggagcgc cttaaagaag atacgtcttt tgggggcaac   2640
ctcggacgag cagtcttcca ggcgaaaaag agggttcttg aacctctggg cctggttgag   2700
gaacctgtta agacggctcc gggaaaaaag aggccggtag agcactctcc tgtggagcca   2760
gactcctcct cgggaaccgg aaaggcgggc cagcagcctg caagaaaaag attgaatttt   2820
ggtcagactg gagacgcaga ctcagtacct gacccccagc ctctcggaca gccaccagca   2880
gccccctctg gtctgggaac taatacgatg gctacaggca gtggcgcacc aatggcagac   2940
aataacgagg gcgccgacgg agtgggtaat tcctcgggaa attggcattg cgattccaca   3000
tggatgggcg acagagtcat caccaccagc acccgaacct gggccctgcc cacctacaac   3060
aaccacctct acaaacaaat ttccagccaa tcaggagcct cgaacgacaa tcactacttt   3120
ggctacagca ccccttgggg gtattttgac ttcaacagat tccactgcca cttttcacca   3180
cgtgactggc aaagactcat caacaacaac tggggattcc gacccaagag actcaacttc   3240
aagctcttta acattcaagt caaagaggtc acgcagaatg acggtacgac gacgattgcc   3300
aataacctta ccagcacggt tcaggtgttt actgactcgg agtaccagct cccgtacgtc   3360
```

```
ctcggctcgg cgcatcaagg atgcctcccg ccgttcccag cagacgtctt catggtgcca   3420
cagtatggat acctcaccct gaacaacggg agtcaggcag taggacgctc ttcattttac   3480
tgcctggagt actttccttc tcagatgctg cgtaccggaa acaactttac cttcagctac   3540
acttttgagg acgttccttt ccacagcagc tacgctcaca gccagagtct ggaccgtctc   3600
atgaatcctc tcatcgacca gtacctgtat tacttgagca gaacaaacac tccaagtgga   3660
accaccacgc agtcaaggct tcagttttct caggccggag cgagtgacat tcgggaccag   3720
tctaggaact ggcttcctgg accctgttac cgccagcagc gagtatcaaa gacatctgcg   3780
gataacaaca acagtgaata ctcgtggact ggagctacca agtaccacct caatggcaga   3840
gactctctgg tgaatccggg cccggccatg gcaagccaca aggacgatga agaaaagttt   3900
tttcctcaga gcggggttct catctttggg aagcaaggct cagagaaaac aaatgtggac   3960
attgaaaagg tcatgattac agacgaagag gaaatcagga caaccaatcc cgtggctacg   4020
gagcagtatg gttctgtatc taccaacctc cagagaggca acagacaagc agctaccgca   4080
gatgtcaaca cacaaggcgt tcttccaggc atggtctggc aggacagaga tgtgtacctt   4140
caggggccca tctgggcaaa gattccacac acggacggac attttcaccc ctctcccctc   4200
atgggtggat tcggacttaa acaccctcct ccacagattc tcatcaagaa caccccggta   4260
cctgcgaatc cttcgaccac cttcagtgcg gcaaagtttg cttccttcat cacacagtac   4320
tccacgggac aggtcagcgt ggagatcgag tgggagctgc agaaggaaaa cagcaaacgc   4380
tggaatcccg aaattcagta cacttccaac tacaacaagt ctgttaatgt ggactttact   4440
gtggacacta atggcgtgta ttcagagcct cgccccattg gcaccagata cctgactcgt   4500
aatctgtaat tgcttgttaa tcaataaacc gtttaattcg tttcagttga actttggtct   4560
ctgcgtattt ctttcttatc tagtttccat gctcctccac ggccaaggat ctgcgatcgc   4620
tccggtgccc gtcagtgggc agagcgcaca tcgcccacag tccccgagaa gttgggggga   4680
ggggtcggca attgaacggg tgcctagaga aggtggcgcg gggtaaactg ggaaagtgat   4740
gtcgtgtact ggctccgcct ttttcccgag ggtgggggag aaccgtatat aagtgcagta   4800
gtcgccgtga acgttctttt tcgcaacggg tttgccgcca gaacacagct gaagcttcga   4860
ggggctcgca tctctccttc acgcgcccgc cgccctacct gaggccgcca tccacgccgg   4920
ttgagtcgcg ttctgccgcc tcccgcctgt ggtgcctcct gaactgcgtc cgccgtctag   4980
gtaagtttaa agctcaggtc gagaccgggc ctttgtccgg cgctcccttg gagcctacct   5040
agactcagcc ggctctccac gctttgcctg accctgcttg ctcaactcta cgtctttgtt   5100
tcgttttctg ttctgcgccg ttacagatcc aagctgtgac cggcgcctac tctagagcta   5160
gcgaattcga atttaaatcg gatccgcggc cgcgcccctc tccctccccc ccccctaacg   5220
ttactggccg aagccgcttg gaataaggcc ggtgtgcgtt tgtctatatg ttattttcca   5280
ccatattgcc gtcttttggc aatgtgaggg cccggaaacc tggccctgtc ttcttgacga   5340
gcattcctag gggtctttcc cctctcgcca aaggaatgca aggtctgttg aatgtcgtga   5400
aggaagcagt tcctctggaa gcttcttgaa gacaaacaac gtctgtagcg accctttgca   5460
ggcagcggaa ccccccacct ggcgacaggt gcctctgcgg ccaaaagcca cgtgtataag   5520
atacacctgc aaaggcggca caaccccagt gccacgttgt gagttggata gttgtggaaa   5580
gagtcaaatg gctctcctca agcgtattca acaaggggct gaaggatgcc cagaaggtac   5640
cccattgtat gggatctgat ctggggcctc ggtgcacatg ctttacatgt gtttagtcga   5700
```

-continued

```
ggttaaaaaa acgtctaggc cccccgaacc acggggacgt ggttttcctt tgaaaaacac   5760

gatgataata tggccacaac catggcgtcc ggaatgattg aacaagatgg attgcacgca   5820

ggttctccgg ccgcttgggt ggagaggcta ttcggctatg actgggcaca acagacaatc   5880

ggctgctctg atgccgccgt gttccggctg tcagcgcagg ggcgcccggt tctttttgtc   5940

aagaccgacc tgtccggtgc cctgaatgaa ctgcaggacg aggcagcgcg gctatcgtgg   6000

ctggccgcga cgggcgttcc ttgcgcagct gtgctcgacg ttgtcactga agcgggaagg   6060

gactggctgc tattgggcga agtgccgggg caggatctcc tgtcatctca ccttgctcct   6120

gccgagaaag tatccatcat ggctgatgca atgcggcggc tgcatacgct tgatccggct   6180

acctgcccat tcgaccacca agcgaaacat cgcatcgagc gagcacgtac tcggatggaa   6240

gccggtcttg tcgatcagga tgatctggac gaagagcatc aggggctcgc gccagccgaa   6300

ctgttcgcca ggctcaaggc gcgcatgccc gacggcgagg atctcgtcgt gacccatggc   6360

gatgcctgct tgccgaatat catggtggaa aatggccgct tttctggatt catcgactgt   6420

ggccggctgg gtgtggcgga ccgctatcag gacatagcgt tggctacccg tgatattgct   6480

gaagagcttg gcggcgaatg ggctgaccgc ttcctcgtgc tttacggtat cgccgctccc   6540

gattcgcagc gcatcgcctt ctatcgcctt cttgacgagt tcttctgagt cgacaatcaa   6600

cctctggatt acaaaatttg tgaaagattg actggtattc ttaactatgt tgctcctttt   6660

acgctatgtg gatacgctgc tttaatgcct ttgtatcatg cgttaactaa acttgtttat   6720

tgcagcttat aatggttaca aataaagcaa tagcatcaca aatttcacaa ataaagcatt   6780

tttttcactg cattctagtt gtggtttgtc caaactcatc aatgtatctt atcatgtctg   6840

gaattgactc aaatgatgtc aattagtcta tcagaagctc atctggtctc ccttccgggg   6900

gacaagacat ccctgtttaa tatttaaaca gcagtgttcc caaactgggt tcttatatcc   6960

cttgctctgg tcaaccaggt tgcagggttt cctgtcctca caggaacgaa gtccctaaag   7020

aaacagtggc agccaggttt agccccggaa ttgactggat tccttttttta gggcccattg   7080

gtattataac aagaaaatat atatataata agttatcacg taagtagaac atgaaataac   7140

aatataatta tcgtatgagt taaatcttaa aagtcacgta aaagataatc atgcgtcatt   7200

ttgactcacg cggtcgttat agttcaaaat cagtgacact taccgcattg acaagcacgc   7260

ctcacgggag ctccaagcgg cgactgagat gtcctaaatg cacagcgacg gattcgcgct   7320

atttagaaag agagagcaat atttcaagaa tgcatgcgtc aattttacgc agactatctt   7380

tctaggg                                                            7387
```